(12) United States Patent  
Qi

(10) Patent No.: US 8,492,110 B2
(45) Date of Patent: Jul. 23, 2013

(54) ANTI AGING AGENTS AND METHODS TO IDENTIFY THEM

(76) Inventor: Haiyan Qi, Dayton, NJ (US)

( * ) Notice: Subject to any disclaimer, the term of this patent is extended or adjusted under 35 U.S.C. 154(b) by 0 days.

(21) Appl. No.: 12/758,384

(22) Filed: Apr. 12, 2010

(65) Prior Publication Data

US 2010/0260733 A1    Oct. 14, 2010

Related U.S. Application Data

(60) Provisional application No. 61/168,311, filed on Apr. 10, 2009, provisional application No. 61/168,335, filed on Apr. 10, 2009.

(51) Int. Cl.
*C12Q 1/02* (2006.01)
*C12N 5/00* (2006.01)

(52) U.S. Cl.
USPC ............................................. 435/29; 435/325

(58) Field of Classification Search
USPC .................................................. 435/29, 325
See application file for complete search history.

(56) References Cited

U.S. PATENT DOCUMENTS

| | | | |
|---|---|---|---|
| 3,993,749 A | 11/1976 | Sehgal | |
| 4,401,653 A | 8/1983 | Eng | |
| 4,650,803 A | 3/1987 | Stella | |
| 4,885,171 A | 12/1989 | Suremdra | |
| 5,078,999 A | 1/1992 | Warner | |
| 5,080,899 A | 1/1992 | Sturm | |
| 5,151,413 A | 9/1992 | Caufield | |
| 5,206,018 A | 4/1993 | Sehgal | |
| 5,286,730 A | 2/1994 | Caufield | |
| 5,286,731 A | 2/1994 | Caufield | |
| 5,288,711 A | 2/1994 | Mitchell | |
| 5,321,009 A | 6/1994 | Baeder | |
| 5,387,589 A | 2/1995 | Kulkarni | |
| 5,496,832 A | 3/1996 | Armstrong | |
| 5,516,781 A | 5/1996 | Morris | |
| 5,561,138 A | 10/1996 | Armstrong | |
| 5,686,245 A | 11/1997 | West et al. | |
| 6,187,756 B1 | 2/2001 | Lee | |
| 6,585,764 B2 | 7/2003 | Wright | |
| 7,026,330 B2 | 4/2006 | Gruppo | |
| 7,083,802 B2 | 8/2006 | Peyman | |
| 7,192,612 B2 | 3/2007 | Morre | |
| 7,384,655 B2 | 6/2008 | Myhill | |
| 2004/0047921 A1 | 3/2004 | Simmons | |
| 2004/0142048 A1 | 7/2004 | Morre | |
| 2004/0176339 A1 | 9/2004 | Sherman | |
| 2005/0013880 A1 | 1/2005 | Magnuson | |
| 2005/0070567 A1 | 3/2005 | Guan | |
| 2005/0187241 A1 | 8/2005 | Wen | |
| 2006/0035904 A1 | 2/2006 | Frisch | |
| 2006/0035907 A1 | 2/2006 | Christensen | |
| 2006/0078533 A1* | 4/2006 | Omoigui ................... 424/78.14 |
| 2006/0094674 A1* | 5/2006 | Neel et al. ...................... 514/44 |
| 2006/0135549 A1 | 6/2006 | Graziani | |
| 2006/0173033 A1 | 8/2006 | Kneissel | |
| 2006/0182771 A1 | 8/2006 | Dor et al. | |
| 2006/0247265 A1 | 11/2006 | Clackson | |
| 2006/0263409 A1 | 11/2006 | Peyman | |
| 2006/0264453 A1 | 11/2006 | Mudumba | |
| 2007/0015720 A1* | 1/2007 | Bulock et al. ................... 514/43 |
| 2007/0037827 A1 | 2/2007 | Nunes et al. | |
| 2007/0059336 A1 | 3/2007 | Hughes | |
| 2007/0099844 A1 | 5/2007 | Prendergast | |
| 2007/0104721 A1 | 5/2007 | Moore | |
| 2007/0105761 A1 | 5/2007 | Chappell | |
| 2007/0155771 A1 | 7/2007 | Rubinsztein | |
| 2008/0146655 A1 | 6/2008 | Yoo et al. | |
| 2008/0194019 A1* | 8/2008 | Cantley et al. ................ 435/375 |
| 2009/0029904 A1 | 1/2009 | Oldham | |
| 2010/0081681 A1* | 4/2010 | Blagosklonny ............... 514/291 |
| 2010/0166869 A1* | 7/2010 | Desai et al. ................... 424/489 |

FOREIGN PATENT DOCUMENTS

| | | |
|---|---|---|
| EP | 0525 960 A1 | 3/1993 |
| KR | 10-2011-7026720 | 6/2012 |
| WO | 02/090588 A1 | 11/2002 |
| WO | 2005026344 A1 | 3/2005 |
| WO | 2009/000213 A1 | 12/2008 |
| WO | 2010/118419 A2 | 10/2010 |

OTHER PUBLICATIONS

Zwerschke et al. Metabolic analysis of senescent human fibroblasts reveals a role for AMP in cellular senescence. 2003. Biochem. J. 376: 403-411.*

Zwerschke et al. Metabolic analysis of senescent human fibroblasts reveals a role for AMP in cellular senescence. 2003. Biochem. J. 376: 403-411.www.grapeseedextract.com. Grape Seed Extract Benefits OPC. Copyright 2007.* www.grapeseedextract.com. Grape Seed Extract Benefits OPC. Copyright 2007.*

NutritionalSupplementsCenter.com. Billberry Extract. Copyright 2005.*

Science Daily. Green Tea Ingredient, EGCG, Significantly Inhibits Breast Cancer growth in Female Mice. Apr. 8, 2008.*

Maswood, N., et al., Caloric restriction increases neurotrophic factor levels and attenuates neurochemical and behavioral deficits in a primate model of Parkinson's diesease. Proc. Natl. Acad. Sci. USA, 101:18171-6 (2004).

(Continued)

*Primary Examiner* — Karen Cochrane Carlson
*Assistant Examiner* — Natalie Moss
(74) *Attorney, Agent, or Firm* — Fox Rothschild LLP; Wansheng Jerry Liu

(57) ABSTRACT

The present invention discloses novel mechanisms in the aging process and describes novel methods for high-throughput screening to identify, detect, and purify agents to be used for improving mitochondrial function, maintaining the cell cycle-arrested state in senescent and post mitotic cells, and thus preventing or treating age-related diseases or disorders associated with accelerated mitochondrial function loss, telomere dysfunction, and/or deterioration of the growth-arrested state. The present invention also discloses a number of compounds or compositions identified from this method. The present invention further provides the use of low doses of rapamycin or its analogs as a mimic of caloric restriction in preventing age-related diseases or disorders.

18 Claims, 23 Drawing Sheets

OTHER PUBLICATIONS

Qin, W., et al., Calorie restriction attenuates Alzheimer's disease type brain amyloidosis in Squirrel monkeys (*Saimiri sciureus*). J. Alzheimer's Dis., 10:417-422 (2006).
Seymour, E.M., et al.,Moderate calorie restriction improves cardiac remodeling and diastolic dysfunction in the Dahl-SS rat. J. Mol. Cell Cardiol., 41:661-668 (2006).
Castello, L., et al., Calorie restriction protects against age-related rat aorta Sclerosis. FASEB J., 19:1863-1865 (2005).
Yu, B.P., et al., Life span study of SPF Fischer 344 male rats fed ad libitum or restricted diet: Longevity, growth, lean body mass and disease. J. Gerontol., 37:130-141 (1982).
Platz, E.A., Energy imbalance and prostate cancer. J. Nutr., 132:3471S-81S (2002).
Steinbach, G., et al., Effect of Caloric Restriction on Colonie Proliferation in Obese Persons: Implications for Colon Cancer Prevention. Cancer Res., 54:1194-1197 (1994).
Michels, K.B., et al., Caloric Restriction and Incidence of Breast Cancer. JAMA, 291:1226-30 (2004).
Fingar, D.C., et al., Target of rapamycin (TOR): an integrator of nutrient and growth factor signals and coordinator of cell growth and cell cycle progression. Oncogene, 23:3151-3171 (2004).
Kaeberlein, M., et al., Regulation of Yeast Replicative Life Span by TOR and Sch9 in Response to Nutrients. Science, 310:1193-1196 (2005).
Powers, R.W., et al., Extension of chronological life span in yeast by decreased TOR pathway signaling. Genes Dev., 20:174-84 (2006).
Vellai, T., et al., Influence of TOR kinase on lifespan in *C. elegans*. Nature, 426:620 (2003) 13.Kapahi, P., et al., Regulation of Lifespan in *Drosophila* by Modulation of Genes in the TOR Signaling Pathway. Curr. Biol., 14:885-890 (2004).
Kapahi, P., et al., Regulation of Lifespan in *Drosophila* by Modulation of Genes in the TOR Signaling Pathway. Curr. Biol., 14:885-890 (2004).
Jia, K., et al., The TOR pathway interacts with the insulin signaling pathway to regulate *C. elegans* larval development, metabolism and life span. Development, 131:3897-3906 (2004).
Balaban, R.S., et al., Mitochondria, Oxidants, and Aging. Cell, 120:483-495 (2005) 16.Chance, B., et al., Hydroperoxide metabolism in mammalian organs. *Physiol. Rev.*, 59:527-605 (1979).
Chance, B., et al., Hydroperoxide metabolism in mammalian organs. Physiol. Rev., 59:527-605 (1979).
Kovacic, P., et al., Mechanisms of Carcinogenesis: Focus on Oxidative Stress and Electron Transfer. Curr. Med. Chem., 8:773-796 (2001).
Aviram, M., et al., Pomegranate juice consumption reduces oxidative stress, atherogenic modifications to LDL, and platelet aggregation: studies in humans and in atherosclerotic apolipoprotein E-deficient mice. Am. J. Clin. Nutr., 71:1062-1076 (2000).
Mates, J.M., Effects of antioxidant enzymes in the molecular control of reactive oxygen species toxicology. Toxicology, 153:83-104 (2000).
Orr, W.C., et al., *Extension of Life-Span by Overexpression of Superoxide Dismutase and Catalase in Drosophila melanogaster*. Science, 263:1128-1130 (1994).
Hagen, T.M., et al., Mitochondrial decay in hepatocytes from old rats: Membrane potential declines, heterogeneity and oxidants increase. Proc. Natl. Acad. Sci. USA, 94:3064-3069, 1997.
Greco, M., et al., Marked aging-related decline in efficiency of oxidative phosphorylation in human skin fibroblasts. *FASEB J.*, 17:1706-1708 (2003).
Trifunovic, A., et al., Premature ageing in mice expressing defective mitochondrial DNA polymerase. Nature, 429:417-423 (2004).
Bonawitz, N.D., et al., Reduced TOR Signaling Extends Chronological Life Span via Increased Respiration and Upregulation of Mitochondrial Gene Expression. Cell Metab., 5:233-235 (2007).
Schulz, T.J., et al., Glucose Restriction Extends *Caenorhabditis elegans* Life Span by Inducing Mitochondrial Respiration and Increasing Oxidative Stress. Cell Metab., 6:280-293 (2007).
Kaeberlein, M., et al., Increased Life Span due to Calorie Restriction in Respiratory-Deficient Yeast. PloS Genet., 1, e69 (2005).

Di Micco, R., et al., Oncogene-induced senescence is a DNA damage response triggered by DNA hyper-replication. Nature, 444:638-642 (2006).
Bartkova, J., Oncogene-induced senescence is part of the tumorigenesis barrier imposed by DNA damage Checkpoints. et al., Nature, 444:633-637 (2006).
Karlseder, J., et al., p53- and ATM-Dependent Apoptosis Induced by Telomeres Lacking TRF2. Science, 283:1321-1325 (1999).
Denchi, E.L., et al., Protection of telomeres through independent control of ATM and ATR by TRF2 and POT1. Nature, 448:1068-1071 (2007).
Guo, X., et al., Dysfunctional telomeres activate an ATM-ATR-dependent DNA damage response to suppress tumorigenesis. EMBO J., 26:4709-4719 (2007).
Braig, M., et al., Oncogene-induced senescence as an initial barrier in lymphoma development. Nature, 436:660-665 (2005).
Collado, M., et al., Senescence in premalignant tumours. Nature 436:642 (2005) 34.Michaloglou, C., et al., BRAFE600-associated senescence-like cell cycle arrest of human naevi. Nature, 436:720-724 (2005).
Michaloglou, C., et al., BRAFE600-associated senescence-like cell cycle arrest of human naevi. Nature, 436:720-724 (2005).
Shay, J.W., et al., The frequency of immortalized human fibroblasts and mammary epithelial cells transfected with SV40 large T-antigen. Exp. Cell. Res., 209:45-52 (1993).
Shay, J.W., et al., A survey of telomerase activity in human cancer. Eur. J. Cancer, 33:787-791 (1997).
Bryan, T.M., et al., Evidence for an alternative mechanism for maintaining telomere length in human tumors and tumor-derived cell lines Nat. Med., 3:271-274 (1997).
Chen, Z., et al., Crucial role of p53-dependent cellular senescence in suppression of Pten-deficient tumorigenesis. Nature, 436:725-730 (2005).
Cosme-Blanco, W., et al., Telomere dysfunction suppresses spontaneous tumorigenesis in vivo by initiating p53-dependent cellular senescence. EMBO Rep. 8:497-503 (2007).
Campisi, J., Cancer and aging: rival and demons. Nat. Rev. Cancer., 3:339-49, 2003.
Faragher, R.G., Aging and the immune system. Biochem. Soc. Trans., 28:221-226 (2000).
Campisi, J., Senescent Cells, Tumor Suppression, Review and Organismal Aging: Good Citizens, Bad Neighbors. Cell, 120:513-522(2005).
Price, J.S., et al., BlacThe role of chondrocyte senescence in osteoarthritis. Aging Cell, 1:57-65 (2002).
Vasile E., et al., Differential expression of thymosin b-10 by early passage and senescent vascular endothelium is modulated by VPF/VEGF: evidence for senescent endothelial cells in vivo at sites of atherosclerosis. FASEB J., 15:458-466 (2001).
Matthews, C., et al., Vascular Smooth Muscle Cells Undergo Telomere-Based Senescence in Human Atherosclerosis Effects of Telomerase and Oxidative Stress. Cir. Res., 99:156-164 (2006).
Maier, B., et al., Modulation of mammalian life span by the short isoform of p53. Genes Dev., 18: 306-319 (2004).
Tyner, S.D., et al., p53 mutant mice that display early ageing-associated phenotypes. Nature, 415:45-53 (2002).
Coppe, J.P., et al., Senescence-Associated Secretory Phenotypes Reveal Cell-Nonautonomous Functions of Oncogenic RAS and the p53 Tumor Suppressor. PloS Biology, 6:2853-2868 (2008).
Blagosklonny, M.V., Aging and Immortality. Cell Cycle, 5:2087-2102 (2006).
Qi, H., et al, Inactivation of Cdc13p Triggers MEC1-dependent Apoptotic Signals in Yeast. J. Biol. Chem., 278: 15136-15141 (2003).
Qi, H., et al., TOR Regulates Cell Death Induced by Telomere Dysfunction in Budding Yeast. PLoS ONE, 3, e3520 (2008).
Shay, J.W., et al, Senescence and immortalization: role of telomeres and telomerase. Carcinogenesis, 26:867-74 (2005).
Shimizu, M., et al., Green Tea Extracts for the Prevention of Metachronous Colorectal Adenomas: A Pilot Study. Cancer Epidemiol. Biomarkers Prev., 17:3020-3025 (2008).
Nakachi, K., et al., Influence of Drinking Green Tea on Breast Cancer Malignancy among Japanese Patients. Jpn. J. Cancer Res., 89:254-261 (1998).

Abbas, S. and Wink, M., Epigallocatechin Gallate from Green Tea (*Camellia sinensis*) Increases Lifespan and Stress Resistance in *Caenorhabditis elegans*. Planta. Med., 75:216-221 (2009).

Rezai-Zadeh, K., et al., Green Tea Epigallocatechin-3-Gallate (EGCG) Modulates Amyloid Precursor Protein Cleavage and Reduces Cerebral Amyloidosis in Alzheimer Transgenic Mice. J. Neurosci., 25(38):8807-8814 (2005).

Choi, Y.B., et al, Protective effect of epigallocatechin gallate on brain damage after transient middle cerebral artery occlusion in rats. Brain Res., 1019:47-54 (2004).

Townsend, P.A., et al., Epigallocatechin-3-gallate inhibits STAT-1 activation and protects cardiac myocytes from ischemia/reperfusion-induced Apoptosis. FASEB J., 18:1621-1623 (2004).

Song, D.K., et al, Polyphenol (−)-Epigallocatechin Gallate during Ischemia Limits Infarct Size Via Mitochondrial KATP Channel Activation in Isolated Rat Hearts. J. Korean Med. Sci., 25(3):380-386 (2010).

Song, E.K,, et al, Epigallocatechin gallate prevents autoimmune diabetes induced by mutiple low doses of streptozotocin in mice. Arch. Pharm. Res., 26:559-563 (2003).

Hsu, S.D., et al., Green tea polyphenols reduce autoimmune symptoms in a murine model for human Sjogren's syndrome and protect human salivary acinar cells from TNF-a-induced cytotoxicity. Autoimmunity, 40:138-147 (2007).

Huang, C.H., et al., EGCG inhibits protein synthesis, lipogenesis, and cell cycle progression through activation of AMPK in p53 positive and negative human hepatoma cells. Mol. Nutr. Food Res., 53(9):1156-1165 (2009).

Raina, K., et al., Oral Grape Seed Extract Inhibits Prostate Tumor Growth and Progression in TRAMP Mice. Cancer Res., 67:5976-5982 (2007).

Siriwardhana, N, et al., Precancerous model of human breast epithelial cells induced by NNK for prevention. Breast Cancer Res. Treat., 109:427-441 (2008).

Carlson, S., et al., The effects of botanical dietary supplements on cardiovascular, cognitive and metabolic function in males and females. Gend. Med., 5 Suppl. A, S76-90 (2008).

Tomaino, A., et al., In vitro protective eVect of a Jacquez grapes wine extract on UVB-induced skin damage. Toxicol. In Vitro., 20:1395-1402 (2006).

Wang, J., et al, Grape-Derived Polyphenolics Prevent A Oligomerization and Attenuate Cognitive Deterioration in a Mouse Model of Alzheimer's Disease. J. Neurosci., 28:6388-6392 (2008).

Park, S.H., et al, Grape seed extract (*Vitis vinifera*) partially reverses high fat diet-induced obesity in C57BL/6J mice. Nutr. Res. Pract., 2:227-233 (2008).

Décordé, K., et al, Chardonnay grape seed procyanidin extract supplementation prevents high-fat diet-induced obesity in hamsters by improving adipokine imbalance and oxidative stress markers. Mol. Nutr. Food Res., 53:659-666 (2008).

Balu, M., et al., Modulatory role of grape seed extract on age-related oxidative DNA damage in central nervous system of rats. Brain Res. Bull., 68:469-473 (2005).

Sangeetha, P., et al., Age associated changes in erythrocyte membrane surface charge: Modulatory role of grape seed proanthocyanidins. Exp. Gerontol., 40:820-828 (2005).

Oh, H., et al., Telomere attrition and Chk2 activation in human heart failure. Proc. Natl. Acad. Sci. USA, 100:5378-5383 (2003).

Led, A., et al., Ablation of telomerase and telomere loss leads to cardiac dilatation and heart failure associated with p53 upregulation. EMBO J., 22:131-139 (2003).

Ogami, M., et al., Telomere Shortening in Human Coronary Artery Diseases. Arterioscler. Thromb. Vasc. Biol., 24:546-550 (2004).

Minamino, T., et al., Endothelial Cell Senescence in Human Atherosclerosis Role of Telomere in Endothelial Dysfunction. Circulation, 105:1541-1544 (2002).

Calvert, J.W., Acute Metformin Therapy Confers Cardioprotection Against Myocardial Infarction Via AMPK-eNOS-Mediated Signaling. Diabetes, 57:696-705 (2008).

Matsunaga, H., /3-Galactosidase Histochemistry and Telomere Loss in Senescent Retinal Pigment Epithelial Cells. Invest. Ophthalmol. Vis. Sci., 40:197-202 (1999).

Liang, F.Q., et al., Oxidative stress-induced mitochondrial DNA damage in human retinal pigment epithelial cells: a possible mechanism for RPE aging and age-related macular degeneration. Exp. Eye Res., 76:397-403 (2003).

Martin, J.A., et al., The Role of Chondrocyte Senescence in the Pathogenesis of Osteoarthritis and in Limiting Cartilage Repair. J. Bone Joint Surg. Am., 85-A Suppl. 2:106-110 (2003).

Ruiz-Romero, C., et al., Mitochondrial Dysregulation of Osteoarthritic Human Articular Chondrocytes Analyzed by Proteomics. Mol. Cell Proteomics., 8:172-189 (2009).

Dave, M., et al., The Antioxidant Resveratrol Protects Against Chondrocyte Apoptosis Via Effects on Mitochondrial Polarization and ATP Production. Arthritis Rheum., 58:2786-2797 (2008).

Tsakiri, K.D., et al., Adult-onset pulmonary fibrosis caused by mutations in telomerase. Proc. Natl. Acad. Sci. USA, 104:7552-7557 (2007).

Alder, J.K., et al., Short telomeres are a risk factor for idiopathic pulmonary fibrosis. Proc. Natl. Acad. Sci. USA, 105:13051-13056 (2008).

Armanios, M.Y., et al., Telomerase Mutations in Families with Idiopathic Pulmonary Fibrosis. N. Engl. J. Med., 356:1317-1326 (2007).

Kuwano, K., Involvement of Epithelial Cell Apoptosis in Interstitial Lung Diseases. Intern. Med., 47:345-353 (2008).

Mine, S., et al., Aging Alters Functionally Human Dermal Papillary Fibroblasts but Not Reticular Fibroblasts: A New View of Skin Morphogenesis and Aging. PLoS ONE, 3(12):e4066 (2008).

Hayflick, L., The Cell Biology of Aging, J. Invest. Dermatol., 73:8-14 (1979).

Varani, J., et al., Decreased Collagen Production in Chronologically Aged Skin. Am. J. Pathol., 168:1861-1868 (2006).

West, M.D., et al., Replicative senescence of human skin fibroblasts correlates with a loss of regulation and overexpression of collagenase activity. Exp. Cell Res., 184:138-147 (1989).

Colmegna, I., et al., Defective Proliferative Capacity and Accelerated Telomeric Loss of Hematopoietic Progenitor Cells in Rheumatoid Arthritis. Arthritis Rheum., 58:990-1000 (2008).

Schönland, S.O. , et al., Premature telomeric loss in rheumatoid arthritis is genetically determined and involves both myeloid and lymphoid cell lineages. Proc. Natl. Acad. Sci. USA, 100:13471-13476 (2003).

Korb, A., et al., Cell death in rheumatoid arthritis. Apoptosis, 14:447-454 (2009).

Da Sylva, T.R., et al., Somatic mutations in the mitochondria of rheumatoid arthritis Synoviocytes. Arthritis Res. Ther., 7:R844-851 (2005).

Ballinger, S.W., et al., Mitochondrial diabetes revisited. Nat. Genet., 7:458-459 (1994).

Ballinger, S.W., et al., Maternally transmitted diabetes and deafness associated with a 10.4 kb mitochondrial DNA deletion. Nat. Genet., 1:11-15 (1992).

Koster, J.C., et al., Targeted Overactivity of b Cell KATP Channels Induces Profound Neonatal Diabetes. Cell, 100:645-654 (2000).

Caccamo, A., et al., Molecular Interplay between Mammalian Target of Rapamycin (mTOR), Amyloid-, and Tau. J. Biol. Chem. 285:13107-20 (2010).

Harrison, D.E., et al., Rapamycin fed late in life extends lifespan in genetically heterogeneous mice. Nature, 460 (7253):392-395 (2009).

Bejdov, I., et al., Mechanisms of Life Span Extension by Rapamycin in the Fruit Fly *Drosophila melanogaster*. Cell Metab., 11(1):35-46 (2010).

Fu X, et al, Etoposide Induces ATM-Dependent Mitochondrial Biogenesis through AMPK Activation. PLoS ONE, 3(4): e2009, 2008.

Vezina, C., et al., Rapamycin (AY-22,989), A new antifungal antibiotics I. Taxonomy of the producing strecptomycete and isolation of the active principle. J. Antibiot., 28:721 (1975).

Sehgal, S.N., et al., Rapamycin (AY-22,989), a new antifungal antibiotic II, Fermentation, isolation and characterization. J. Antibiot., 28:727(1975).

Baker, H.A., et al., Rapamycin (AY-22,989), a new antifungal antibiotic III. In vitro and in vivo evaluation. J. Antibiot., 31:539 (1978).

Santos, E. and Nebreda, A.R., The structural and functional properties of ras protein. FASEB, 3:2151-2163 (1989).

Carlson, et al., Rapamycin, a potential disease-modifying antiarthritic drug. J. Pharmacol. Exp. Ther., 266:1125-1138 (1993).

McGill, J.K., et al., Impaired Functional Recovery After Stroke in the Stroke-Prone Spontaneously Hypertensive Rat. Stroke, 36:135-141 (2005).

Sharkey, J.J. and Butcher, S.P., Immunophilins mediate the neuronprotective effects of FK506 in focal. Nature, 371:336-339 (1994).

Lin, L.L., et al, Protective Effects of Scutellarin and Breviscapine on Brain and Heart Ischemia in Rats. J. Cardiovasc. Pharmaco., 50:327-332 (2007).

Maassen, J.A., et al, Mitochondrial Diabetes Mellitus. J. Endocrinol. Invest. 25:447-484 (2002).

Hara, Y., et al., Green tea Polyphenol (-)-epigallocatechin-3-gallate provides resistance to apoptosis in isoleted islets. J. Hepatobiliary Pancreat Surg. 14:493-497 (2007).

Gupta, S.K., et al., Green tea (*Camellia sinensis*) protects against selenite-induced oxidative stress in experimental cataractogenesis. Ophthalmic Res. 34:258-263 (2002).

Kastrinaki, M-C., et al., Functional, molecular and proteomic characterisation of bone marrow mesenchymal stem cells in rheumatiod arthritis. Ann Rheum Dis. 67:741-749 (2007).

van den Ouweland, J.M.W., et al., Maternally inherited diabetes and deafness is a distinct subtype of diabetes and associates with a single point mutation in the mitochondrial tRNAleu(UUR) gene. Diabetes, 43:746-751 (1994).

Foroncewicz, B., et al., Efficacy of rapamycin in patient with juvenile rheumatoid arthritis. Transplant International 18:366-368 (2005).

Tamura, A., et al., Focal cerebral ischaemia in the rat: 1. Description of technique and early neuronpathological consequences following middle cerebral artery occlusion. J Cerebral Blood Flow and Metabolism., 1:53-60 (1981).

Wallace, D.C., Mouse models for mitochondrial disease. Am. J. Med. Genet., 106:71-93 (2001).

Halvorsen, T.L., Targeted Overactivity of b Cell KATP Channels Induces Profound Neonatal Diabetes. J. Endocrinol., 166:103-109 (2000).

Malagelada, C., et al., Rapamycin Protects against Neuron Death in In Vitro and In Vivo Models of Parkinson's Disease. J. Neurosci., 30(3):1166-1175 (2010).

Tsang et al., "Targeting Mammalian Target of Repamycin (mTOR) for Health and Disease", Drug Discovery Today, 2007, vol. 12, No. 3/4, p. 120; col. 2, para 4,p. 121, col. 1, para 3.

Scarpulla, "Transcriptionaly Paradigms in mammalian Mitochondrial Biogenesis and Function", Physiol Rev, 2008, vol. 88, pp. 611-638; p. 613, col. 2, para 2.

Thaler et al., "RASSF1A Mediates p21Cip1/Wa1-Dependent Cell Cycle Arrest and Senescence through Modulation of the Raf-MED-ERK Pathway and Inhibition of Akt." Cancer Res, Mar. 1, 2009, vol. 69, No. 5; abstract.

Collado et al., "Inhibition of the Phosphoinositide 3-Kinase Pathway Induces a Senescence-like arrest mediated by p27 Kip1", Journal of Biological Chemistry, 2000, vol. 275, No. 29, pp. 21960-21968, abstract.

Hock et al., "Transcriptional Control of Mitochondrial Biogenesis and Function", Annual Review of Physiology, Mar. 2009, vol. 71, pp. 177-203, p. 190, col. 1, para 1, figure 1.

Lizcano et al., "LKB1 is a master kinase that activates 13 kinases of the SMPK subfamily, including MARK/PAR-1", The EMBO Journal, 2004, No. 23, pp. 833-843, abstract.

Telomerase Inhibitors Identified by a Forward Chemical Genetics Apporach Using a Yeast Strain with Shortened Telomere Length-Nakai et al. Chemistry & Biology 13, 183-190 Feb. 2006.

Telomere dysfunction in aging and cancer; Gilley et al.; International Journal of Biochemistry and Cell Biology. vol. 37, No. 5; May 1, 2005.

Yeast cell death during DNA damage arrest is independent of caspase or reactive oxygen species; Wysocki et al.; The Journal of Cell Biology, vol. 166 No. 3, Aug. 2, 2004 311-316.

Testing Geroprotectors in Experiments on Cellular Cultures: Pros and Cons; A.H. Xoxjiob; Probl. aging and longevity, 2009, 18 No. 1-C32-36.

Bernhard et al. (Resveratrol causes arrest in S-phase prior to Fas-independent apoptosis in CEM-C7H2 acute leukemia cells. Cell Death and Differentiation (2000) 7:834-842).

Wu et al. (Cell cycle arrest-in G0/G1 phase by contact inhibition and TGF-B1 in mink Mv1Lu lung epithelial cells. Am J Physiol Lung Cell Mol Physiol (1996) 270: L879-888).

Hahm et al. (Honokial causes G0-G1 phases cell cycle arrest in human prostate cancer cells in association with suppression of retinoblast protein level/phosphorylation and inhibition of E2F1 transcriptional activity. Mol Cancer Ther (2007) 6:2686-2695).

\* cited by examiner

ANTI AGING AGENTS AND METHODS TO IDENTIFY THEM

CROSS REFERENCE TO RELATED APPLICATIONS

This application claims the benefit under 35 U.S.C. §119(e) of U.S. Provisional Application No. 61/168,311, filed on Apr. 10, 2009, and U.S. Provisional Application No. 61/168,335, filed on Apr. 10, 2009, both of which are incorporated herein by reference in their entirety.

FIELD OF THE INVENTION

This invention is related to novel anti-aging agents, novel methods to detect or identify these agents, and use of the anti-aging agents so identified for the prevention and/or treatment of age-related diseases or disorders. The invention is also related to a novel method for measuring the anti-aging biological concentration of anti-aging agents in biological samples. In particular, the invention introduces the use of low doses of rapamycin or its analogs, among other target-of-rapamycin (TOR) inhibitors, as anti-aging agents mimicking calorie restriction for preventing or treating various age-related diseases or disorders.

BACKGROUND OF THE INVENTION

Study of human aging processes is important, in part because many diseases or conditions become more prominent among aged people, for example, cancers, Alzheimer's disease, Parkinson's disease, stroke, heart failure, and heart attack, just to name a few, among which many still lack effective preventive or treatment methods. Therefore, the search for more effective prevention or treatment methods for the age-related diseases or disorders through studies of animal aging processes has become one of the most important endeavors embarked by the scientific community in the last decade. Although abundant literature has contributed to the understanding of aging processes, full understanding of the processes remains to be a major scientific challenge faced by mankind. Given the increasing population of aged people around the world and the rising health care burden and cost associated therewith, systematic studies of the aging processes leading to effective discovery of anti-aging agents for the prevention or treatment of age-related diseases or disorders are becoming increasingly important. This invention represents such a systematic approach aiming to provide effective methods for the discovery of anti-aging agents that can be developed into effective prevention and/or treatment of age-related diseases or disorders.

Among various theories concerning the aging processes and the methods derived from the theories that could be useful for the treatment of age-related diseases, the nutrient signaling pathway (caloric restriction), the mitochondria pathway (reactive oxygen species, or ROS), and the telomere dysfunction theory are prominent.

Nutrient Signaling Pathway (Caloric Restriction) and Aging. Caloric restriction (CR) has been recognized as the most practicable method to retard the rate of aging from yeast to mammals. CR has also been shown to reduce the incidence or delay the onset of age-related diseases such as Parkinson's disease in a primate model (Maswood, N., et al., *Proc. Natl. Acad. Sci. USA*, 101:18171-6 (2004)), Alzheimer's disease (Qin, W., et al., *J. Alzheimer's Dis.*, 10:417-422 (2006)), hypertension and heart problems in the Dahl-SS rat model (Seymour, E. M., et al., *J. Mol. Cell Cardiol.*, 41:661-668 (2006)), fibrosis (Castello, L., et al., *FASEB J.*, 19:1863-1865 (2005)), and kidney disease (Yu, B. P., et al., *J. Gerontol.*, 37:130-141 (1982)). CR also inhibits a variety of spontaneous neoplasias and decreases the incident of human breast, colon and prostate cancers (reviewed in Platz, E. A., *J. Nutr.*, 132: 3471S-81S (2002); Steinbach, G., et al., *Cancer Res.*, 54:1194-1197 (1994); Michels, K. B., et al., *JAMA*, 291: 1226-30 (2004)).

The well-conserved kinase TOR (Target of rapamycin) integrates signals from nutrients, mitogenic growth factors, energy, and stress to regulate catabolic and anabolic processes (Fingar, D. C., et al., *Oncogene*, 23:3151-3171 (2004)). In response to optimal growth factors and nutrients, mammalian TOR (mTOR) stimulates the cell's synthetic capabilities (such as ribosome biogenesis and protein translation initiation), leading to increases in cell mass and size and accelerates proliferation (Kim, E., et al., *Hum. Gene Ther.*, 14:1415-1428 (2003)). Conversely, inhibition of TOR by growth factor withdrawal, nutrient starvation, or stress leads to the down-regulation of high energy-consuming processes and inhibition of proliferation.

TOR pathway may play an important role in the life span extension induced by CR in budding yeast, *Ceanorhabditis elegans* and *Drosophila* (Kaeberlein, M., et al., *Science*, 310: 1193-1196 (2005); Powers, R. W., et al., *Genes Dev.*, 20:174-84 (2006); Vellai, T., et al., *Nature*, 426:620 (2003); Kapahi, P., et al., *Curr. Biol.*, 14:885-890 (2004); Jia, K., et al., *Development*, 131:3897-3906 (2004)). As the function of TOR is well conserved, its role in aging may also apply to humans.

The Mitochondrion/ROS and Aging. Mitochondria are cellular organelles responsible for converting metabolic fuels (e.g., glucose and fatty acids) into a usable form of energy, adenosine 5'-triphosphate (ATP), through the process of oxidative phosphorylation. Mitochondria are also involved in other processes that are important for proper cellular function, including calcium homeostasis, intracellular signal transduction, and the regulation of apoptosis.

The process of oxidative phosphorylation for ATP generation in mitochondria is also the main source of reactive oxygen species (ROS) within the cell (about 90% of total ROS in cells) (Balaban, R. S., et al., *Cell*, 120:483-495 (2005)). Under normal physiological conditions, ROS leaked during oxidative phosphorylation is estimated to represent 1-5% of the oxygen consumed during this process (Chance, B., et al., *Physiol. Rev.*, 59:527-605 (1979)). Due to the limited repair capacity of mitochondrial DNA (mtDNA) and the proximity to the oxidants, mitochondria are particularly vulnerable to accumulation of damages. Mutations in mtDNA then result in impaired function of oxidative phosphorylation, leading to increased ROS production and the subsequent accumulation of more mutations. As ROS are highly reactive molecules and can generate diverse damages in the cells, the ROS vicious cycle is believed to account for an exponential increase in oxidative damage during aging, which results in a gradually functional decline that characterizes the aging process.

ROS may be associated with many age-related diseases, for example, diabetes, cardiovascular disease, cancer and Parkinson's disease (Kovacic, P., et al., *Curr. Med. Chem.*, 8:773-796 (2001); Aviram, M., et al., *Am. J. Clin. Nutr.*, 71:1062-1076 (2000); Maassen, J. A., et al., *J. Endocrinol. Invest.*, 25:477-484 (2002)). The fact that eukaryotes develop a host anti-oxidant defense system also supports the important role of endogenous ROS production (Mates, J. M., *Toxicology*, 153:83-104 (2000)) and overexpression of superoxide dismutase and catalase extends life span in *Drosophila melanogaster* (Orr, W. C., et al., *Science*, 263:1128-1130 (1994)).

Previous studies indicate that mitochondrial integrity declines as a function of age as monitored by decreases in mitochondrial membrane potential, mitochondrial number, and ATP generation/$O_2$ consumption (Hagen, T. M., et al., *Proc. Natl. Acad. Sci. USA,* 94:3064-3069, 1997; Greco, M., et al., *FASEB J.,* 17:1706-1708 (2003)). Mutations in mitochondrial function cause a number of human genetic diseases with clinical manifestations including blindness, deafness, movement disorders, dementias, cardiovascular disease, muscle weakness, renal dysfunction, and endocrine disorders. Furthermore, it has been reported that mice with a dramatic increase in mitochondrial DNA mutations (due to a proof-reading-deficient mutation in mtDNA polymerase PolgA) exhibited a shorter life span, accompanied with certain premature aging phenotypes (Trifunovic, A., et al., *Nature,* 429:417-423 (2004)). Moreover, life span extension in yeast (Chronological life span) by deletion of TOR1 and in *C. Elegans* by glucose restriction has been reported to be via mitochondrial respiration (Bonawitz, N. D., et al., *Cell Metab.,* 5:233-235 (2007); Schulz, T. J., et al., *Cell Metab.,* 6:280-293 (2007)). These results suggest the important role of mitochondrial function in aging and age-related diseases in mammals. However, contradictory results have also been reported. For example, CR-induced life span extension in budding yeast was reported to be independent of mitochondrial function (Kaeberlein, M., et al., *PloS Genet.,* 1, e69 (2005)). Therefore, the role of mitochondria in the aging process remains to be unclear.

Telomeres, Senescence, Aging and Cancer. Telomeres are ends of chromosomes consisting of G-rich repeated DNA sequences on one strand. The telomeres are bound by telomere binding proteins to protect them from being recognized as the naturally occurring double-stranded DNA breaks (DSBs).

Dysfunctional telomeres can be caused by progressive shortening of telomeres due to the internal problem of DNA replication by DNA polymerase and the lack of telomerase activity in most somatic cells in humans. Eventually, the critically shortened telomeres cannot be bound by telomere proteins and are thus exposed as natural DSBs, which activate DNA damage responses and induce RB- and p53-dependent cell cycle arrest. This process is termed replicative senescence. In addition, senescence can be induced by oncogenes activation via the same DNA damage responses, resulting in tumor suppression (Di Micco, R., et al., *Nature,* 444:638-642 (2006); Bartkova, J., et al., *Nature,* 444:633-637 (2006)). Furthermore, DNA damage agents have also been reported to trigger senescence as well.

Telomere dysfunction also occurs when there is a telomere binding protein defect. For example, expression of a dominant-negative TTAGGG repeat binding factor 2 (TRF2), as well as knockdown of protection of telomeres 1 (POT1), results in telomere dysfunction and DNA damage signals (Karlseder, J., et al., *Science,* 283:1321-1325 (1999); Denchi, E. L., et al., *Nature,* 448:1068-1071 (2007); Guo, X., et al., *EMBO J.,* 26:4709-4719 (2007)).

Long telomeres have been associated with longevity in humans, while short telomeres have been associated with cancers, idiopathic pulmonary fibrosis and a variety of proliferative tissue disorders. For example, the telomerase mutation in human causes Dyskeratosis congenita and patients typically die early of bone marrow failure.

Replication senescence has been shown to be a barrier for tumor progression, since cancer cells require unlimited replication potential. Indeed, senescent markers are prominent in pre-malignant lesions but undetectable in advanced cancers in mouse models and in human cancers (Braig, M., et al., *Nature,* 436:660-665 (2005); Collado, M., et al., *Nature* 436: 642 (2005); Michaloglou, C., et al., *Nature,* 436:720-724 (2005)). All cancers bypass senescence by activating telomerase or alternative telomere lengthening by recombination (Shay, J. W., et al., *Exp. Cell. Res.,* 209:45-52 (1993); Shay, J. W., et al., *Eur. J. Cancer,* 33:787-791 (1997); Kim, N. W., et al., *Science,* 266:2011-2015 (1994); Bryan, T. M., et al., *Nat. Med.,* 3:271-274 (1997)). The progression of early stage prostate cancer to malignance is blocked by senescence (Chen, Z., et al., *Nature,* 436:725-730 (2005)). Furthermore, the spontaneous tumorigenesis induced by telomere dysfunction in telomerase mutant mice Terc$^{-/-}$ was shown to be inhibited by p53-mediated senescence (Cosme-Blanco, W., et al., *EMBO Rep.* 8:497-503 (2007)). Senescence is assumed to stop the cell cycle and facilitate repair, thus blocking further development of the initial lesions.

Senescence is also viewed as a major contributor to aging (Campisi, J., *Nat. Rev. Cancer,* 3:339-49; Faragher, R. G., *Biochem. Soc. Trans.,* 28:221-226 (2000)). For example, senescent cells increase with age in mammalian tissues (Campisi, J., *Cell,* 120:1-10 (2005)). Senescent cells have been found at sites of age-related pathologies such as osteoarthritis and atherosclerosis (Price, J. S., et al., *Aging Cell,* 1:57-65 (2002); Vasile E., et al., *FASEB J.,* 15:458-466 (2001); Matthews, C., et al., *Cir. Res.,* 99:156-164 (2006)). Moreover, chronically active p53 both promotes cellular senescence and accelerates aging phenotypes in mice (Maier, B., et al., *Genes Dev.,* 18: 306-319 (2004); Tyner et al., *Nature,* 415:45-53 (2002)). Furthermore, it has been shown that senescent cells secret proteins that facilitate tumor progression and inflammation response (Coppe, J. P., et al., *Plos-Biology,* 6:2853-2868 (2008)). It has been proposed that the programmed senescence leads to age-related diseases and limited our life span (Blagosklonny, M. V., *Cell Cycle,* 5:2087-2102 (2006)). Therefore, anti-aging research from the telomere angle is currently focused on preventing senescence.

Despite all the studies, the role of telomeres in aging process remains unclear. For example, it cannot explain why a mouse has longer telomeres but a shorter life span than a human. It is not clear if or how telomeres work in the aging process of post-mitotic cells.

Other aging theories have also been proposed, for example, the protein damage accumulation theory, the DNA mutation accumulation theory, and the stem cell exhausting theory. Among the above, which theories represent the true nature of the aging processes and whether and/or how they are related to each other are still unclear. Therefore, at least to some degree, human aging processes remain to be a mystery.

Age-related diseases or disorders, such as cancers, cardiovascular diseases, and neuronal degeneration diseases, are leading causes of death in humans. Pharmaceutical agents for the treatment of these age-related diseases or disorders are being searched according to the current understanding of the specific diseases, due to the limited understanding about the aging processes. As a result, to date, these diseases have been studied independently of each other and disconnected from the aging processes. Therefore, there is a need to develop a systemic approach based on the aging processes to the discovery of novel anti-aging agents for the prevention and treatment of age-related diseases or disorders.

SUMMARY OF THE INVENTION

The present invention provides the forgoing need by disclosing novel mechanisms in the aging processes and novel methods based the novel mechanisms to identify or detect anti-aging agents useful for the prevention and/or treatment of age-related diseases or disorders. The novel methods disclosed herein can be used to identify novel anti-aging agents rapidly by high-throughput screening using various well-understood yeast mutant models. In particular, the present invention describes the use of low doses of rapamycin or its analogs, among a number of other anti-aging agents identified by using the methods disclosed, for effective prevention and/or treatment of various age-related diseases or disorders.

In one aspect, the present invention provides a method of identifying or detecting an agent for preventing or treating an age-related disease or disorder, the method comprising screening one or more compounds or compositions against a senescence model system and monitoring their anti-aging activity.

In another aspect, the present invention provides a method of identifying or detecting an agent for preventing or treating an age-related disease or disorder, the method comprising screening one or more compounds or compositions and measuring their activity against at least one of components of the TOR/AMPK/Mitochondria/Senescence pathway.

In another aspect, the present invention provides a method of identifying or detecting an agent for preventing or treating an age-related disease or disorder, the method comprising screening one or more compounds or compositions and detecting their activity against at least one of components of the mitochondrial biogenesis pathway.

In another aspect, the present invention provides a method of identifying or detecting an agent for preventing or treating aging or an age-related disease or disorder, the method comprising screening one or more compounds or compositions and detecting their activity against at least one of components of the AMPK pathway.

In another aspect, the present invention provides a method of identifying or detecting an agent for preventing or treating an age-related disease or disorder, the method comprising screening one or more compounds or compositions and detecting their activity against at least one of components of the senescence pathway, wherein the agent maintains senescence or cell cycle-arrested state in post-mitotic cells or prevents deterioration of mitochondria or cell death following senescence deterioration.

In another aspect, the present invention provides a method of preventing or treating an age-related disease or disorder, the method comprising administering to a subject in need thereof a composition comprising an agent identified according to any of the embodiments described in any of other aspects of the present invention, or a pharmaceutically acceptable salt, solvate, or prodrug thereof.

In another aspect, the present invention provides a method of preventing or treating an age-related disease or disorder associated with deterioration of telomeres and/or mitochondria, the method comprising administering to a subject in need thereof a composition comprising a 5'-adenosine monophosphate-activated protein kinase (AMPK) activator, or a pharmaceutically acceptable salt, solvate, or prodrug thereof, which directly or indirectly activates AMPK, increases mitochondrial biogenesis, and maintains a cell cycle-arrested state in the senescent or post-mitotic cells of the subject.

In another aspect, the present invention provides a method of preventing or treating an age-related disease or disorder, the method comprising administering to a subject in need thereof a composition comprising a target-of-rapamycin (TOR) inhibitor, or a pharmaceutically acceptable salt, solvate, or prodrug thereof, wherein the TOR inhibitor (a) extends replication potential, (b) maintains senescence or cell cycle-arrested state in post-mitotic cells, or (c) prevents deterioration of mitochondria or cell death following senescence deterioration. In a preferred embodiment of this aspect, said TOR inhibitor is a low dose of rapamycin or an analog thereof.

In another aspect, the present invention provides a method for detecting an anti-aging agent in a biological sample, the method comprising using a yeast senescence model.

In another aspect, the present invention provides a method for determining biological concentration of an anti-aging agent in a biological sample, the method comprising using a yeast senescence model and a pre-established standard equation or curve of the anti-aging agent.

In another aspect, the present invention discloses that mitochondrial function plays an important role in maintaining senescence induced by telomere dysfunction, and caloric restriction (CR) prevents deterioration of the senescent state through the TOR/AMPK/mitochondrial pathway. This mechanism is conserved in both yeast and human models of telomere dysfunction. The conserved mechanism thus allows the use of telomere dysfunction models in yeast and in humans to search for pharmaceuticals that can promote mitochondrial function and thus prevent or treat deterioration of senescence. Since many age-related diseases are linked to mitochondrial dysfunction and/or telomere dysfunction, agents identified by this method can potentially be used to prevent age-related diseases or disorders. Thus, in contrast to the currently prevalent anti-aging strategies, which are mainly focused on inhibiting senescence by taking senescence as the major contributor to the aging process, the present invention introduces a novel strategy for preventing or treating age-related diseases or disorders through maintaining senescence.

Other aspects and specific preferred embodiments of the present invention are described in more details in the following embodiments and claims.

DETAILED DESCRIPTION OF THE INVENTION

Figure 1A:
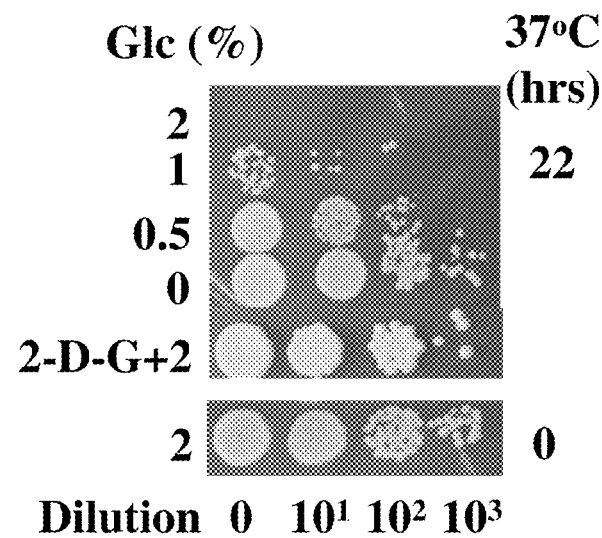
FIG. 1 shows that limiting nutrient signaling inhibits cell death induced by cdc13-1p inactivation. (A) Glucose restriction and 2-deoxy-glucose treatment inhibit cell loss induced by Cdc13p inactivation as assayed by colony formation assay. To induce telomere dysfunction, fresh overnight cultures of cdc13-1 were diluted into YEPD medium with the indicated concentrations of glucose or 2-deoxyglucose and incubated at 37° C. for 24 hrs. For colony formation assay, treated cells were then serially diluted 10-fold in $H_2O$ and 5 μL was spotted onto regular YEPD plates. The plates were incubated at 24° C. for survived cells to form colonies. The starting number of live-cells was also counted by this colony formation assay. (B) Nitrogen restriction inhibits cell death induced by cdc13-1p inactivation as monitored by a colony formation assay. Cells were incubated in synthetic medium (SC) or SC-N (SC without amino acids and $(NH_4)_2SO_4$ as nitrogen sources) at 37° C. for 24 hrs. The number of survived cells was counted using colony formation assay as described in 1A. (C-D) Inhibition of TOR by low doses of rapamycin (labeled as Rapa) (below growth inhibition concentration) can prevent cell death induced by cdc13-1p inactivation. Cells were incubated with the indicated concentrations of rapamycin in YEPD medium at 37° C. for 24 hrs. The number of survived cells was measured by the colony formation assay as in 1A. For growth curve, fresh overnight culture was diluted into YEPD medium and incubated at 24° C. in the presence of the indicated concentrations of rapamycin. Cell Density ($OD_{595}$) was measured at the indicated time points and plotted against the time. (E) Deterioration of growth arrested cdc13-1 cells can be delayed by low dose of rapamycin (1 nM) and glucose restriction (0.5%) as measured by counting surviving cells using the colony formation assay. The data represent an average of three experiments.

The present invention describes novel methods for identifying, detecting, and purifying anti-aging agents and use of the agents for the prevention and treatment of age-related diseases or disorders. The invention is based on, inter alia, the following discoveries: (1) that inhibition of nutrient signals prolongs the cell cycle-arrested state induced by telomere dysfunction in yeast via the AMPK and subsequent mitochondrial pathway; (2) that low doses of rapamycin, glucose restriction, and AMPK activators stimulate mitochondrial function and prolong senescence in primary human fibroblasts; (3) that several anti-aging and cancer chemopreventive agents stimulate mitochondrial function and inhibit loss of senescent cells in both yeast and human cells; (4) that many age-related diseases or disorders are associated with dysfunction of mitochondria and/or telomeres; and (5) that low doses of rapamycin prevent cerebellar and myocardial ischemic infarction, reduce ROS triggered by MPP+, increase life span of cultured primary neuron cells and inhibit tumor cell transformation.

In a first aspect, the present invention provides a method of identifying or detecting an agent for preventing or treating an age-related disease or disorder, the method comprising screening one or more compounds or compositions against a senescence model system and monitoring their anti-aging activity.

In one embodiment of the first aspect, the present invention provides a method of identifying or detecting an agent for preventing or treating an age-related disease or disorder, wherein the anti-aging activity is preventing deterioration of a cell cycle-arrested state in senescent or post-mitotic cells.

In another embodiment of the first aspect, the present invention provides a method of identifying or detecting an agent for preventing or treating an age-related disease or disorder, wherein the anti-aging activity is stimulating, improving, or maintaining mitochondrial function.

In another embodiment of the first aspect, the present invention provides a method of identifying or detecting an agent for preventing or treating an age-related disease or disorder, wherein the anti-aging activity is preventing an age-related disease or disorder that is associated with loss of mitochondrial or telomere function.

In another embodiment of the first aspect, the present invention provides a method of identifying or detecting an agent for preventing or treating an age-related disease or disorder, wherein the anti-aging activity is preventing increase of reactive oxygen species (ROS) or apoptotic death induced by telomere dysfunction.

In another embodiment of the first aspect, the present invention provides a method of identifying or detecting an agent for preventing or treating an age-related disease or disorder, wherein the senescence model system is a mutant yeast comprising a dysfunctional telomere.

In another embodiment of the first aspect, the present invention provides a method of identifying or detecting an agent for preventing or treating an age-related disease or disorder, wherein the senescence model system is a primary human cell line that exhibits insufficient telomerase activity.

In another embodiment of the first aspect, the present invention provides a method of identifying or detecting an agent for preventing or treating an age-related disease or disorder, wherein the senescence model system is a human cell line that exhibits telomere dysfunction caused by a mutation or defect in a telomere binding protein or telomerase.

In another embodiment of the first aspect, the present invention provides a method of identifying or detecting an agent for preventing or treating an age-related disease or disorder, wherein the senescence model system is a telomere dysfunction model caused by a chemical agent.

In another embodiment of the first aspect, the present invention provides a method of identifying or detecting an agent for preventing or treating an age-related disease or disorder, wherein the senescence model system is a model created by oncogene activation and/or activation of DNA damage response.

In another embodiment of the first aspect, the present invention provides a method of identifying or detecting an agent for preventing or treating an age-related disease or disorder, wherein the senescence model system is a cell line of mouse, rat or *S. Pombe* which exhibits telomere dysfunction.

In another embodiment of the first aspect, the present invention provides a method of identifying or detecting an agent for preventing or treating an age-related disease or disorder, the method comprising the steps of:
  (i) incubating a compound or composition with yeast cells under conditions where a cell cycle is arrested by telomere dysfunction or DNA damage;
  (ii) measuring the population of dead yeast cells using an apoptotic assay, or alternatively;
  (iii) removing the conditions under which the cell cycle is arrested and measuring the number of survived cells; and
  (iv) comparing the population of dead cells obtained in step (ii) or the number of survived cells obtained in step (iii) with the population of dead cells or the number of survived cells, respectively, obtained in a control experiment under the same conditions as in step (i) but in the absence of said compound or composition,
  wherein a decreased population of the dead yeast cells obtained in step (ii) or an increased number of the survived cells obtained in step (iii) as compared with those of the control experiment would indicate that the compound or composition incubated is a candidate of anti-aging agent.

In another embodiment of the first aspect, the present invention provides a method of identifying or detecting an agent for preventing or treating an age-related disease or disorder, the method comprising the steps of:
  (i) incubating a compound or composition with mammalian senescent cells for a period of time;
  (ii) measuring the population of survived senescent cells; and
  (iii) comparing the population of the survived mammalian senescent cells of step (vi) with population of survived senescent cells obtained in a control experiment,
  wherein an increased population of the survived senescent cells as compared to the control experiment would indicate that the compound or composition incubated with the cells is a candidate of anti-aging agent.

In another embodiment of the first aspect, the present invention provides a method of identifying or detecting an agent for preventing or treating an age-related disease or disorder, the method comprising the steps of:
(i) incubating a compound or composition with normal growing human cells for a period of time;
(ii) measuring mitochondrial biogenesis of the human cells by measuring mitochondrial mass, mitochondrial DNA content, or expression of mitochondrial transcription factors; and
(iii) comparing the result of step (ix) with that of a control experiment,
wherein an enhanced mitochondrial biogenesis obtained in step (ix) as compared to the control experiment would indicate that the identified compound or composition is a candidate of anti-aging agent.

In another embodiment of the first aspect, the present invention provides a method of identifying or detecting an agent for preventing or treating an age-related disease or disorder, the method comprising any combination of the steps described in the above three embodiments.

In another embodiment of the first aspect, the present invention provides a method of identifying or detecting an agent for preventing or treating an age-related disease or disorder, wherein the senescence model system is a mutant yeast comprising a dysfunctional telomere selected from cdc13-1, cdc13-2, stn1-1, cdc17-1, cdc17-2, hdf1, hdf2, est1, est2, and est3.

In another embodiment of the first aspect, the present invention provides a method of identifying or detecting an agent for preventing or treating an age-related disease or disorder, wherein the senescence model system is a primary human cell line comprising at least one of fibroblasts, endothelial cells, and epithelial cells, which exhibits insufficient telomerase activity.

In another embodiment of the first aspect, the present invention provides a method of identifying or detecting an agent for preventing or treating an age-related disease or disorder, wherein the senescence model system is a human cell line comprising a mutation in TRF2, POT1, TERT, TERC, or WRN, which exhibits telomere dysfunction.

In another embodiment of the first aspect, the present invention provides a method of identifying or detecting an agent for preventing or treating an age-related disease or disorder, wherein the senescence model system is a telomere dysfunction model caused by a chemical agent selected from the group consisting of bleomycin, adriamycin, and G-quadruplex ligands.

In another embodiment of the first aspect, the present invention provides a method of identifying or detecting an agent for preventing or treating an age-related disease or disorder, wherein the age-related disease or disorder is an abnormal proliferative disease, a degenerative disease, or a function-decreasing disorder.

In another embodiment of the first aspect, the present invention provides a method of identifying or detecting an agent for preventing or treating an age-related disease or disorder, wherein said one or more compounds or compositions each belong to a library of compounds and/or compositions. Thus, a preferred embodiment of this invention encompasses a high throughput screening of a plurality of compounds or compositions.

In a second aspect, the present invention provides a method of identifying or detecting an agent for preventing or treating an age-related disease or disorder, the method comprising screening one or more compounds or compositions and measuring their activity against at least one of components of the TOR/AMPK/Mitochondria/Senescence pathway, wherein the agent (a) extends replication potential, (b) maintains senescence or cell cycle-arrested state in post-mitotic cells, or (c) prevents deterioration of mitochondria or cell death following deterioration of senescence or cell cycle arrested-state. This aspect is related to the first aspect of the present invention in that said anti-aging activity is on any of the components of the TOR/AMPK/Mitochondria/Senescence pathway with an effect of maintaining senescence.

In one embodiment of the second aspect, the present invention provides a method of identifying or detecting an agent for preventing or treating an age-related disease or disorder, wherein the age-related disease or disorder is associated with senescence deterioration, cell death following deterioration of a cell cycle-arrested state in senescent and post-mitotic cells, accelerated mitochondrial deterioration and increased oxidative stress, or telomere dysfunction.

In another embodiment of the second aspect, the present invention provides a method of identifying or detecting an agent for preventing or treating an age-related disease or disorder, wherein said components of the TOR/AMPK/Mitochondria/Senescence pathway comprise Insulin/IGF, Insulin/IGF receptors, PI3K, PDK1, PTEN, TSC1, TSC2, AKT, Rheb, raptor, GβL, S6K, TOR, AMPK, STRAD, MO25, LKB1, glucose uptake, amino acid uptake, CaMKKβ, PGC-1α, PGC-1β, NRF-1, NRF-2, TFAM, TFB1M, TFB2M, ERRs (e.g., ERRα, ERRβ and ERRγ), PPARs (e.g., PPARα, PPARδ and PPARγ), SIRT1, RIP140, PRC, POLRMT, ATM, p53, p21, $p19^{ARF}$, WAF1, $P16^{INK4a}$, pRB, E2F, PTEN, and $p27^{KIP1}$.

In another embodiment of the second aspect, the present invention provides a method of identifying or detecting an agent for preventing or treating an age-related disease or disorder, wherein the age-related disease or disorder is an abnormal proliferative disease, a degenerative disease, or a function-decreasing disorder.

In another embodiment of the second aspect, the present invention provides a method of identifying or detecting an agent for preventing or treating an age-related disease or disorder, wherein said one or more compounds or compositions each belong to a library of compounds and/or compositions.

In a third aspect, the present invention provides a method of identifying or detecting an agent for preventing or treating an age-related disease or disorder, the method comprising screening one or more compounds or compositions and detecting their activity against at least one of components of the mitochondrial biogenesis pathway, wherein the agent (a) extends replication potential, (b) maintains senescence or cell cycle-arrested state in post-mitotic cells, or (c) prevents deterioration of mitochondria or cell death following senescence deterioration. This aspect is related to the first aspect of the present invention in that said anti-aging activity is against any of the components of the mitochondrial biogenesis pathway with an effect of maintaining senescence.

In one embodiment of the third aspect, the present invention provides a method of identifying or detecting an agent for preventing or treating an age-related disease or disorder, wherein the age-related disease or disorder is associated with cell death following deterioration of a cell cycle-arrested state in senescent and post-mitotic cells, senescence deterioration, accelerated mitochondrial deterioration and increased oxidative stress, or telomere dysfunction, and.

In another embodiment of the third aspect, the present invention provides a method of identifying or detecting an agent for preventing or treating an age-related disease or disorder, wherein the components of the mitochondrial biogenesis pathway comprise AMPK, STRAD, MO25, LKB1, CaMKKβ, PGC-1α, PGC-1β, NRF-1, NRF-2, TFAM, TFB1M, TFB2M, ERRs (e.g., ERRα, ERRβ and ERRγ), PPARs (e.g., PPARα, PPARδ and PPARγ), SIRT1, RIP140, PRC, and POLRMT.

In another embodiment of the third aspect, the present invention provides a method of identifying or detecting an agent for preventing or treating an age-related disease or disorder, wherein the age-related disease or disorder is an abnormal proliferative disease, a degenerative disease, or a function-decreasing disorder.

In another embodiment of the third aspect, the present invention provides a method of identifying or detecting an agent for preventing or treating an age-related disease or disorder, wherein said one or more compounds or compositions each belong to a library of compounds and/or compositions.

In a fourth aspect, the present invention provides a method of identifying or detecting an agent for preventing or treating aging or an age-related disease or disorder, the method comprising screening one or more compounds or compositions and detecting their activity against at least one of components of the AMPK pathway, wherein the agent (a) extends replication potential, (b) maintains senescence or cell cycle-arrested state in post-mitotic cells, or (c) prevents deterioration of mitochondria or cell death following senescence deterioration. This aspect is related to the first aspect of the present invention in that said anti-aging activity is against any of the components of the AMPK pathway with an effect of maintaining senescence.

In one embodiment of the fourth aspect, the present invention provides a method of identifying or detecting an agent for preventing or treating an age-related disease or disorder, wherein the age-related disease or disorder is associated with senescence deterioration, age-related cell loss, or tumorigenesis and malignant progression of cancers.

In another embodiment of the fourth aspect, the present invention provides a method of identifying or detecting an agent for preventing or treating an age-related disease or disorder, wherein the components of the AMPK pathway comprise AMPK, ATM, LKB1, STRAD, MO25, and CaMKKβ.

In another embodiment of the fourth aspect, the present invention provides a method of identifying or detecting an agent for preventing or treating an age-related disease or disorder, wherein the age-related disease or disorder is an abnormal proliferative disease, a degenerative disease, or a function-decreasing disorder.

In another embodiment of the fourth aspect, the present invention provides a method of identifying or detecting an agent for preventing or treating an age-related disease or disorder, wherein said one or more compounds or compositions each belong to a library of compounds and/or compositions.

In a fifth aspect, the present invention provides a method of identifying or detecting an agent for preventing or treating an age-related disease or disorder, the method comprising screening one or more compounds or compositions and detecting their activity against at least one of components of the senescence pathway, wherein the agent maintains senescence or cell cycle-arrested state in post-mitotic cells or prevents deterioration of mitochondria or cell death following senescence deterioration. This aspect is related to the first aspect of the present invention in that said anti-aging activity is against any of the components of the senescence pathway with an effect of maintaining senescence.

In one embodiment of the fifth aspect, the present invention provides a method of identifying or detecting an agent for preventing or treating an age-related disease or disorder, wherein the age-related disease or disorder is associated with senescence deterioration, cell death following deterioration of a cell cycle-arrested state in senescent and post-mitotic cells, accelerated mitochondrial deterioration and increased oxidative stress, or telomere dysfunction.

In another embodiment of the fifth aspect, the present invention provides a method of identifying or detecting an agent for preventing or treating an age-related disease or disorder, wherein the components of the senescence pathway comprise ATM, p53, p21, p19$^{ARF}$, WAF1, p16$^{INK4a}$, pRB, E2F, PTEN, and p27$^{KIP1}$.

In another embodiment of the fifth aspect, the present invention provides a method of identifying or detecting an agent for preventing or treating an age-related disease or disorder, wherein the age-related disease or disorder is an abnormal proliferative disease, a degenerative disease, or a function-decreasing disorder.

In another embodiment of the fifth aspect, the present invention provides a method of identifying or detecting an agent for preventing or treating an age-related disease or disorder, wherein said one or more compounds or compositions each belong to a library of compounds and/or compositions.

In a sixth aspect, the present invention provides a method of preventing or treating an age-related disease or disorder, the method comprising administering to a subject in need thereof a composition comprising an agent identified according to any embodiments in the first to fifth aspects of the present invention as described above, or a pharmaceutically acceptable salt, solvate, or prodrug thereof. This aspect thus encompasses the use of any of the anti-aging compounds or compositions identified by the methods described herein for preparation or manufacture of a medicament for the prevention or treatment of an age-related disease or disorder as encompassed by this disclosure.

In one embodiment of the sixth aspect, the present invention provides a method of preventing or treating an age-related disease or disorder, wherein the age-related disease or disorder is associated with deterioration of a cell cycle-arrested state in senescent or post-mitotic cells, mitochondrial dysfunction, or telomere dysfunction.

In another embodiment of the sixth aspect, the present invention provides a method of preventing or treating an age-related disease or disorder, wherein the agent is selected from organic molecules, inorganic molecules, natural products, peptides, proteins, DNAs, RNAs, and metabolic intermediates thereof.

In another embodiment of the sixth aspect, the present invention provides a method of preventing or treating an age-related disease or disorder, wherein the agent is selected from AICAR, low dose of rapamycin or analogs thereof, EGCG, grape seed extract, bilberry extract, selenite, genistein, diallyl trisulfide, benzyl isothiocyanate, phenyl isothiocyanate, phenethyl isothiocyanate, resveratrol, lycopene, and allyl isothiocyanate.

In another embodiment of the sixth aspect, the present invention provides a method of preventing or treating an age-related disease or disorder, wherein the composition further comprises a second agent selected from an antioxidant, an antihypertensive agent, a lipid-lowering agent, an anti-stroke agent, an anti-cancer agent, and a different anti-aging agent.

In another embodiment of the sixth aspect, the present invention provides a method of preventing or treating an age-related disease or disorder, wherein the composition further comprises an antioxidant selected from vitamin C, vitamin E, beta carotene and other carotenoids, selenium, lipoic acid, lycopine, lutein, zeaxanthin, coenzyme Q10, glutathione, N-acetyl cysteine, melatonin, genistein, estrodiol, tea extract, and grape seed extract.

In another embodiment of the sixth aspect, the present invention provides a method of preventing or treating an age-related disease or disorder, wherein the composition further comprises a pharmaceutically acceptable carrier.

In another embodiment of the sixth aspect, the present invention provides a method of preventing or treating an age-related disease or disorder, wherein the composition is administered orally, parenterally, topically, transdermally, or in a suppository or aerosol form.

In another embodiment of the sixth aspect, the present invention provides a method of preventing or treating an age-related disease or disorder, wherein the age-related disease or disorder is an abnormal proliferative disease, a degenerative disease, or a function-decreasing disorder.

In another embodiment of the sixth aspect, the present invention provides a method of preventing or treating an age-related disease or disorder, wherein the age-related disease or disorder is selected from tumorigenesis and malignant cancer development, neurodegenerating disease, myocardial infarction (heart attack), heart failure, atherosclerosis, hypertension, osteoarthritis, osteoporosis, sarcopenia, loss of bone marrow, cataract, multiple sclerosis, Sjogren, Rheumatoid arthritis, degraded immune function, diabetes, Idiopathic pulmonary fibrosis, and age-related macular degeneration, cerebellar infarction, stroke, Alzheimer's disease, Parkinson's disease, Huntington's disease, and disorders caused by the decline in testosterone, estrogen, growth hormone, IGF-I, or energy production.

In another embodiment of the sixth aspect, the present invention provides a method of preventing or treating an age-related disease or disorder, wherein said subject is a mammal.

In another embodiment of the sixth aspect, the present invention provides a method of preventing or treating an age-related disease or disorder, wherein said subject is a human.

In a seventh aspect, the present invention provides a method of preventing or treating an age-related disease or disorder, the method comprising administering to a subject in need thereof a composition comprising an AMPK activator, or a pharmaceutically acceptable salt, solvate, or prodrug thereof, which directly or indirectly activates AMPK, increases mitochondrial biogenesis, and maintains a cell cycle-arrested state in the senescent or post-mitotic cells of the subject. This aspect of the invention thus encompasses the use of an AMPK activator for preparation or manufacture of a medicament for the prevention or treatment of an age-related disease or disorder encompassed by this disclosure. This aspect is related to the sixth aspect of the present invention in that said agent is an AMPK activator.

In one embodiment of the seventh aspect, the present invention provides a method of preventing or treating an age-related disease or disorder, wherein the age-related disease or disorder is associated with mitochondrial function loss, telomere dysfunction, senescence deterioration and age-dependent cell loss, or mitochondrial deterioration or cell cycle-arrested state in post-mitotic cells.

In one embodiment of the seventh aspect, the present invention provides a method of preventing or treating an age-related disease or disorder, wherein said AMPK activator is selected from AICAR, metformin, 2-deoxyglucose, 3-O-methylglucose, LY294002, berberine, phenformin, A-769662, thiazolidinediones, dexamethasone, statins, leptin, adiponectin, cilostazol, EGCG, senelite, allyl isothiocyanate, and phenethyl isothiocyanate.

In another embodiment of the seventh aspect, the present invention provides a method of preventing or treating an age-related disease or disorder, wherein the composition further comprises a second agent selected from an antioxidant, an antihypertensive agent, a lipid-lowering agent, an anti-stroke agent, an anti-cancer agent, and a different anti-aging agent.

In another embodiment of the seventh aspect, the present invention provides a method of preventing or treating an age-related disease or disorder, wherein the composition further comprises a pharmaceutically acceptable carrier.

In another embodiment of the seventh aspect, the present invention provides a method of preventing or treating an age-related disease or disorder, wherein the composition is administered orally, parenterally, topically, transdermally, or in a suppository or aerosol form.

In another embodiment of the seventh aspect, the present invention provides a method of preventing or treating an age-related disease or disorder, wherein the age-related disease or disorder is an abnormal proliferative disease, a degenerative disease, or a function-decreasing disorder.

In another embodiment of the seventh aspect, the present invention provides a method of preventing or treating an age-related disease or disorder, wherein the age-related disease or disorder is selected from tumorigenesis and malignant cancer development, neurodegenerating disease, myocardial infarction (heart attack), heart failure, atherosclerosis, hypertension, osteoarthritis, osteoporosis, sarcopenia, loss of bone marrow, cataract, multiple sclerosis, Sjogren, Rheumatoid arthritis, degraded immune function, diabetes, Idiopathic pulmonary fibrosis, and age-related macular degeneration, cerebellar infarction, stroke, Alzheimer's disease, Parkinson's disease, Huntington's disease, and disorders caused by the decline in testosterone, estrogen, growth hormone, IGF-I, or energy production.

In another embodiment of the seventh aspect, the present invention provides a method of preventing or treating an age-related disease or disorder, wherein said subject is a mammalian animal.

In another embodiment of the seventh aspect, the present invention provides a method of preventing or treating an age-related disease or disorder, wherein said subject is a human.

In an eighth aspect, the present invention provides a method of preventing or treating an age-related disease or disorder, the method comprising administering to a subject in need thereof a composition comprising a target-of-rapamycin (TOR) inhibitor, or a pharmaceutically acceptable salt, solvate, or prodrug thereof, wherein the TOR inhibitor (a) extends replication potential, (b) maintains senescence or cell cycle-arrested state in post-mitotic cells, or (c) prevents deterioration of mitochondria or cell death following senescence deterioration. This aspect of the invention thus encompasses the use of a TOR inhibitor, or a pharmaceutically acceptable salt, solvate, or prodrug thereof, for preparation or manufacture of a medicament for the prevention or treatment of an age-related disease or disorder encompassed by this disclosure. This aspect is related to the sixth aspect of the present invention in that said agent is a TOR inhibitor.

In one embodiment of the eighth aspect, the present invention provides a method of preventing or treating an age-related disease or disorder, wherein the age-related disease or disorder is associated with mitochondrial function loss, telomere dysfunction, senescence deterioration and age-dependent cell loss, or mitochondrial deterioration or cell cycle-arrested state in post-mitotic cells.

In another embodiment of the eighth aspect, the present invention provides a method of preventing or treating an age-related disease or disorder, wherein said TOR inhibitor is a low dose of rapamycin or an analog thereof.

In another embodiment of the eighth aspect, the present invention provides a method of preventing or treating an age-related disease or disorder, wherein said TOR inhibitor is a low dose of rapamycin or an analog selected from Deforolimus, AP-23675, AP-23841, Zotarolimus, CCI779/Temsirolimus, RAD-001/Everolimus, 7-epi-rapamycin, 7-thiomethyl-rapamycin, 7-epi-trimethoxy-rapamycin, 2-desmethyl-rapamycin, and 42-O-(2-hydroxy)ethyl-rapamycin, or a pharmaceutically acceptable salt, solvate, or prodrug thereof.

In another embodiment of the eighth aspect, the present invention provides a method of preventing or treating an age-related disease or disorder, wherein said TOR inhibitor is a low dose of rapamycin, or a pharmaceutically acceptable salt, solvate, or prodrug thereof.

In another embodiment of the eighth aspect, the TOR inhibitor rapamycin is used at low doses from about 0.1 to about 10000 pM in serum medium, or from 0.1 to about 10000 ng/kg/day in animal. It is a surprising discovery that rapamycin at these low doses exhibits novel function rather than inhibits protein cell growth, although it is traditionally known that rapamycin is an immunosuppressant at therapeutic doses (1 mg/day to 5 mg/day) which inhibit cell growth at G1 phase of cell cycle and may also target other functional protein complexes. As a result, the therapeutic doses of rapamycin thus show various side effects, including increases in serum cholesterol and triglycerides, renal function deficiency, anemia, impaired wound healing, diarrhea, asthenia, hypotension, pain, malignant neoplasm progression, hepatic neoplasm malignant, ascites, failure to thrive, mental status changes, splenic infarction, and colitis, etc. These side effects can be avoided when low doses of rapamycin are used according to the present invention.

The effective dosage of rapamycin or its analogs may vary depending upon the particular compound utilized, the mode of administration, the specific disorders being treated, as well as various physical factors related to the individual being treated. As used in accordance with this invention, satisfactory results may be obtained when rapamycin is administered at a daily oral dosage of about 0.01 to about 50 µg/day depending on the specific tissue disease or disorder treated, which is estimated to be about 0.001% to about 5% of the therapeutic doses (1 mg/day to 5 mg/day). As used in accordance with this invention, the administration schedule of two to four days with rapamycin followed by two to five days of rapamycin-free may yield best results with the least adverse effects.

In another embodiment of the eighth aspect, the present invention provides a method of preventing or treating an age-related disease or disorder, wherein said low doses of rapamycin, or an analog thereof, are below about 10%, below about 8%, below about 6%, below about 4%, below about 2%, below about 1%, below about 0.1%, below about 0.01%, or below about 0.001% of an approved therapeutic dose.

In one preferred embodiment of the eighth aspect, the present invention provides a method of preventing or treating an age-related disease or disorder, wherein rapamycin, or an analog thereof, is administered at a dose in the range of about 8% to about 10% of an approved therapeutic dose.

In another preferred embodiment of the eighth aspect, the present invention provides a method of preventing or treating an age-related disease or disorder, wherein rapamycin, or an analog thereof, is administered at a dose in the range of about 6% to about 8% of an approved therapeutic dose.

In another preferred embodiment of the eighth aspect, the present invention provides a method of preventing or treating an age-related disease or disorder, wherein rapamycin, or an analog thereof, is administered at a dose in the range of about 4% to about 6% of an approved therapeutic dose.

In another preferred embodiment of the eighth aspect, the present invention provides a method of preventing or treating an age-related disease or disorder, wherein rapamycin, or an analog thereof, is administered at a dose in the range of about 2% to about 4% of an approved therapeutic dose.

In another preferred embodiment of the eighth aspect, the present invention provides a method of preventing or treating an age-related disease or disorder, wherein rapamycin, or an analog thereof, is administered at a dose in the range of about 1% to about 2% of an approved therapeutic dose.

In another preferred embodiment of the eighth aspect, the present invention provides a method of preventing or treating an age-related disease or disorder, wherein rapamycin, or an analog thereof, is administered at a dose in the range of about 0.1% to about 1% of an approved therapeutic dose.

In another preferred embodiment of the eighth aspect, the present invention provides a method of preventing or treating an age-related disease or disorder, wherein rapamycin, or an analog thereof, is administered at a dose in the range of about 0.01% to about 0.1% of an approved therapeutic dose.

In another preferred embodiment of the eighth aspect, the present invention provides a method of preventing or treating an age-related disease or disorder, wherein rapamycin, or an analog thereof, is administered at a dose in the range of about 0.01% to about 0.1% of an approved therapeutic dose.

In another preferred embodiment of the eighth aspect, the present invention provides a method of preventing or treating an age-related disease or disorder, wherein rapamycin, or an analog thereof, is administered at a dose in the range of about 0.001% to about 0.01% of an approved therapeutic dose.

In another preferred embodiment of the eighth aspect, the present invention provides a method of preventing or treating an age-related disease or disorder, wherein rapamycin, or an analog thereof, is administered at a dose in the range of about 0.0001% to about 0.001% of an approved therapeutic dose.

In another embodiment of the eighth aspect, the present invention provides a method of preventing or treating an age-related disease or disorder, wherein the low dose of rapamycin is administered as an isolated compound.

In another embodiment of the eighth aspect, the present invention provides a method of preventing or treating an age-related disease or disorder, wherein the low dose of rapamycin is administered as a crude extract.

In another embodiment of the eighth aspect, the present invention provides a method of preventing or treating an age-related disease or disorder, wherein the low dose of rapamycin is administered as an unpurified microorganism comprising rapamycin.

In another embodiment of the eighth aspect, the present invention provides a method of preventing or treating an age-related disease or disorder, wherein the low dose of rapamycin is administered as an unpurified microorganism Streptomyces hygroscopicus, which comprises rapamycin.

In another embodiment of the eighth aspect, the present invention provides a method of preventing or treating an age-related disease or disorder, wherein the composition further comprises a second agent selected from an antioxidant, an antihypertensive agent, a lipid-lowering agent, an anti-stroke agent, an anti-cancer agent, and a different anti-aging agent.

In another embodiment of the eighth aspect, the present invention provides a method of preventing or treating an age-related disease or disorder, wherein the composition further comprises an antioxidant to control ROS from both cellular and mitochondrial levels.

In another embodiment of the eighth aspect, the present invention provides a method of preventing or treating an age-related disease or disorder, wherein the composition further comprises an antioxidant selected from vitamin C, vitamin E, beta carotene and other carotenoids, selenium, lipoic acid, lycopine, lutein, zeaxanthin, coenzyme Q10, glutathione, N-acetyl cysteine, melatonin, genistein, estrodiol, tea extract, and grape seed extract.

In another embodiment of the eighth aspect, the present invention provides a method of preventing or treating an age-related disease or disorder, wherein the composition is administered orally, parenterally, topically, transdermally, or in a suppository or aerosol form.

In another embodiment of the eighth aspect, the present invention provides a method of preventing or treating an age-related disease or disorder, wherein the age-related disease or disorder is an abnormal proliferative disease, a degenerative disease, or a function-decreasing disorder.

In another embodiment of the eighth aspect, the present invention provides a method of preventing or treating an age-related disease or disorder, wherein the age-related disease or disorder is selected from tumorigenesis and malignant cancer development, neurodegenerating disease, myocardial infarction (heart attack), heart failure, atherosclerosis, hypertension, osteoarthritis, osteoporosis, sarcopenia, loss of bone marrow, cataract, multiple sclerosis, Sjogren, Rheumatoid arthritis, degraded immune function, diabetes, Idiopathic pulmonary fibrosis, and age-related macular degeneration, cerebellar infarction, stroke, Alzheimer's disease, Parkinson's disease, Huntington's disease, and disorders caused by the decline in testosterone, estrogen, growth hormone, IGF-I, or energy production.

In one preferred embodiment of the eighth aspect, the present invention provides a method of preventing or treating an age-related disease or disorder, wherein said agent is a lose dose of rapamycin or an analog thereof, and wherein the age-related disease or disorder is selected from tumorigenesis and malignant cancer development, neurodegenerating disease, myocardial infarction (heart attack), heart failure, atherosclerosis, hypertension, osteoarthritis, osteoporosis, sarcopenia, loss of bone marrow, cataract, multiple sclerosis, Sjogren, Rheumatoid arthritis, degraded immune function, diabetes, Idiopathic pulmonary fibrosis, and age-related macular degeneration, cerebellar infarction, stroke, Alzheimer's disease, Parkinson's disease, Huntington's disease, and disorders caused by the decline in testosterone, estrogen, growth hormone, IGF-I, or energy production.

In another preferred embodiment of the eighth aspect, the present invention provides a method of preventing or treating an age-related disease or disorder, wherein said agent is a low dose of rapamycin or an analog thereof, and wherein the age-related disease or disorder is selected from tumorigenesis or malignant progression of a cancer, Parkinson's disease, stroke, cerebellar infarction, and myocardial infarction.

In another preferred embodiment of the eighth aspect, the present invention provides the use of rapamycin at low concentrations in prolonging senescence induced by age-dependent telomere dysfunction, oncogene activation, or DNA damaging agents (e.g., ROS, anticancer drugs, UV or ionizing irradiation), since the same senescence mechanism is involved in these processes, via the DNA damage response. Thus, the methods of the present invention may be used to treat various benign tumors and prevent them from malignancy progression. The methods of the present invention may thus be used in populations that have high risk of cancers, such as aged populations, and people who are often in contact with mutagens, or subject to UV, or ionizing irradiations. The methods of the present invention may also be used in patients who take drugs with high risks of inducing cancers, such as women who are taking hormone replacements. Furthermore, the methods of the present invention may also be used in cancer patients who are undergoing a chemotherapy that could induce secondary cancers.

In another preferred embodiment of the eighth aspect, the present invention provides the use of rapamycin at low concentrations in preventing brain damage induced by stroke. Thus, a low dose of rapamycin can be used as the emergency drug to treat stroke, including both ischemic and hemorrhagic stroke. To yield the best result, the present invention also provides the use of a low dose of rapamycin in combination of the emergency medicine to treat ischemic stroke such as tissue plasminogen activator (t-PA), a clot-dissolving medicine.

In another preferred embodiment of the eighth aspect, the present invention provides the use of rapamycin at low concentrations in preventing stroke and reoccurring strokes. In order to have the best prevention results, in another embodiment of the method, the present invention also provides the use of low doses of rapamycin in combination with medicines of different mechanisms that reduce the risk of stroke. These medicines include, but are not limited to, antiplatelet medicines (e.g., clopidogrel, Agrrenox), anticoagulants (e.g., warfarin, heparin), lipid lowering drugs (e.g., statins) and blood pressure medicines (e.g., Angiotensin-converting enzyme (ACE) inhibitors, Angiotensin II receptor blockers (ARBs), Beta-blockers, Diuretics, and Calcium channel blockers).

In another preferred embodiment of the eighth aspect, the present invention provides the use of rapamycin at low concentrations in preventing neuron degenerative diseases, including, but not limited to, Alzheimer's, Parkinson's, Huntington's diseases.

In another preferred embodiment of the eighth aspect, the present invention provides the use of rapamycin at low concentrations in preventing damages at heart induced by myocardial infarction. Thus, the invention provides the use of rapamycin at a low dose in preventing myocardial infarction or heart attack. In order to have best result, the rapamycin can also be used in combination with medicines of different mechanisms for preventing the risk of heart attack. These medicines include, but are not limited to, antiplatelet medicines (e.g., clopidogrel, Agrrenox), anticoagulants (e.g., warfarin, heparin), lipid lowering drugs (e.g., statins), blood pressure medicines (e.g., Angiotensin-converting enzyme (ACE) inhibitors, Angiotensin II receptor blockers (ARBs), Beta-blockers, Diuretics, and Calcium channel blockers), and blood sugar control medicines (e.g., Metformin and Pioglitazone).

A person of skill in the art would understand that the distribution of rapamycin is uniform in different tissue or cell type, and each compound or composition identified from the anti-aging screen may have a specific distribution pattern in different tissues or cell types. In one aspect of the method, the invention provides the use of rapamycin at a low dose in combination with at least one other anti-aging agent, including, but not limited to AICAR, 2-deoxyglucose, LY294002, metformin, EGCG, GSE, senelite, genistein, silibinin, allyl isothiocyanate, phenethyl isothiocyanate, bilberry extracts, diallyl trisulfide, benzyl isothiocyanate, resveratrol, and lycopene.

In another embodiment of the eighth aspect, rapamycin at a low dose may be administered in any useful manner, including oral, via implants, parenteral (including intravenous, intraperitoneal and subcutaneous injections), topical, rectal, intranasal, vaginally, inhaled, aerosol, and transdermal forms. The transdermal administrations include all administrations across the surface of the body and the inner linings of bodily passages including the epithelial and mucosal tissues. Such administrations may be carried out using the present compounds or pharmaceutically acceptable salts thereof in lotions, creams, foams, patches, suspensions, solutions, and suppositories (rectal and vaginal).

In another embodiment of the eighth aspect, the present invention provides the use of rapamycin at a low dose in the form of an ingredient of solid food, beverages or liquid foods, including alcoholic or non-alcoholic ones, for example, water, wine, and juices, etc.

In a ninth aspect, the present invention provides a method for detecting an anti-aging agent in a biological sample, the method comprising the steps of:
 (i) optionally diluting the biological sample with a solvent;
 (ii) incubating the diluted sample with mutant yeast cells under conditions where the cell cycle of the yeast cells is arrested by telomere dysfunction or DNA damage;
 (iii) removing the conditions under which the cell cycle is arrested and measuring the number of survived yeast cells; and
 (iv) comparing the number of survived cells obtained in step (iii) to the number of survived cells in a control experiment under the same conditions as those of the incubating step (ii) except for the absence of the subject biological sample,
 wherein the increased number of survived cells obtained in step (iii) compared to the number of survived cells in the control experiment indicates that the biological sample comprises an anti-aging agent.

In a tenth aspect, the present invention provides a method for determining biological concentration of an anti-aging agent in a biological sample, the method comprising the steps of:
 (i) optionally diluting a subject biological sample with a solvent;
 (ii) incubating the diluted biological sample with mutant yeast cells under conditions where the cell cycle of the yeast cells is arrested by telomere dysfunction or DNA damage;
 (iii) removing the conditions under which the cell cycle is arrested and measuring the number of survived yeast cells;
 (iv) optionally comparing the number of survived cells obtained in step (iii) to the number of survived cells in a control experiment under the same conditions as those of the incubating step (ii) except for the absence of the subject biological sample; and
 (v) calculating the biological concentration of the anti-aging agent by applying the number of survived yeast cells to a pre-established standard equation or curve between the concentration of anti-aging agent and the number of survived yeast cells.

In one embodiment of the tenth aspect, the present invention provides a method to prepare a standard equation or curve to be used for calculation of biological concentration of an anti-aging agent in a biological sample, the method comprising the steps of:
 (vi) preparing a plurality of standard solutions having different known concentrations of a purified anti-aging agent using a solvent to be used for incubating the subject biological sample;
 (vii) incubating the standard solutions with the mutant yeast cells under conditions where the cell cycle is arrested by telomere dysfunction or DNA damage;
 (viii) removing the conditions under which the cell cycle is arrested and measuring the number of survived yeast cells in each incubated standard solution; and
 (ix) plotting the numbers of survived cells obtained in step (viii) against the corresponding concentrations of the anti-aging agent to obtain a standard curve and/or to obtain a standard equation.

This aspect is related to the ninth aspect of the present invention in that a quantitative analysis is involved by calculating the biological concentration of an anti-aging agent using a pre-established equation or curve described above. Thus, the present invention encompasses methods comprising any reasonable combinations of the steps described in the two aspects.

In another embodiment of the tenth aspect, the present invention provides a method for determining biological concentration of an anti-aging agent in a biological sample, wherein the anti-aging agent is a compound or composition identified or used according to any of the embodiments in any aspects of the present invention as described above.

In another embodiment of the tenth aspect, the present invention provides a method for determining biological concentration of an anti-aging agent in a biological sample, wherein the anti-aging agent is rapamycin or an analog thereof. In a preferred embodiment, the rapamycin or analog is at a low dose.

In another embodiment of the tenth aspect, the present invention provides a method for determining biological concentration of an anti-aging agent in a biological sample, wherein the mutant yeast is selected from cdc13-1, cdc13-2, stn1-1, cdc17-1, cdc17-2, hdf1, hdf2, est1, est2, and est3.

Other aspects or preferred embodiments of the present invention may include any suitable combinations of the embodiments disclosed herein. Yet other aspects and embodiments may be found in other parts of the description provided herein.

Definitions

As used herein, the singular forms "a", "an", and "the" include plural reference unless the context clearly dictates otherwise.

As used herein, the term "optional" or "optionally" means that the subsequently described event or circumstance can occur or otherwise, and that the description includes instances where the event or circumstance occurs and instances where it does not.

As used herein, the term "age-related disorder" or "age-related disease" refers to disorders or diseases in which aging is a major risk factor. Based on the type of diseases, age-related diseases or disorders include three main types: (1) abnormal poliferative diseases, such as cancer; (2) degenerative diseases, including neuron degenerating disease (Alzheimer's, Parkinson's, stroke), myocardial infarction, heart failure, atherosclerosis, hypertension, osteoarthritis, osteoporosis, sarcopenia, loss of bone marrow, Rheumatoid arthritis, degraded immune function, diabetes, Idiopathic pulmonary fibrosis, age-related macular degeneration; and (3) function decreasing disorders, including declines in testosterone, estrogen, growth hormone, IGF-I, reduced energy production and so on. Based on the type of cells involved, age-related diseases or disorders can also be classified as two main classes: (1) in postmitotic cells: neuron degeneration (Alzheimer's, Parkinson's, stroke), sarcopenia (loss of muscle), cardiovascular diseases (heart failure, myocardial infarction); and (2) in mitotic cells: loss of bone marrow, degraded immune function, diabetes, idiopathic pulmonary fibrosis, age-related macular degeneration, rheumatoid arthritis, osteoarthritis, osteoporosis, atherosclerosis, and hypertension. More specifically, Age-related diseases or disorders associated with mitochondrial dysfunction or/and telomere dysfunction include, but are not limited to, cancer, osteoarthritis, age-related macular degeneration, idiopathic pulmonary fibrosis, Parkinson's disease, Alzheimer's disease, Huntington's disease, skin aging, cataract, multiple sclerosis, Sjogren, Rheumatoid arthritis, atherosclerosis, myocardial infarction, heart failure, hypertension, stroke, diabetes mellitus, osteoporosis, obesity, grey hair, hearing loss, and so on. All of the above-mentioned diseases or disorders are encompassed by the present invention.

In some preferred embodiments, the term "age-related disease or disorder" refers to a disease or disorder selected from tumorigenesis and malignant cancer development, myocardial infarction (heart attack), cerebellar infarction, stroke, Parkinson's disease, heart failure, atherosclerosis, hypertension, cataract, age-related macular degeneration, sarcopenia, osteoarthritis, osteoporosis, loss of bone marrow, multiple sclerosis, Sjogren, Rheumatoid arthritis, degraded immune function, diabetes, Idiopathic pulmonary fibrosis, and neurodegenerating disease, Alzheimer's disease, Huntington's disease, and disorders caused by the decline in testosterone, estrogen, growth hormone, IGF-I, or energy production.

As used herein, the term "anti-aging effect" refers to phenotypes comprising increased mitochondrial biogenesis and function, reduced ROS levels, extended life span of senescent cells and post-mitotic cells such as neuron cells, prevented age-related disorders, such as tumorigenesis, malignant progression of cancers, cerebellar infarction and myocardial infarction.

As used herein, the term "prevent age-related disease or disorder" means reducing the incidences, delaying or reversing the diseases related to aging.

As used herein, the term "senescence" refers to a cell cycle-arrested state in mitotic cells, which can be induced by telomere dysfunction, DNA damage, or oncogene activation. In budding yeast, senescent cells caused by telomere dysfunction are arrested at the G2/M phase of the cell cycle. In mammalian cells, senescent cells are arrested at the G0 phase, which is a non-dividing phase outside of the cell cycle. Senescence in WI-38 fibroblasts means that cells show no increase in number under the microscope for 10 days after passage and exhibit β-galactosidase positive staining.

As used herein, the term "post-mitotic cells" refers to a group of cells that are in arrested state at G0, which is a non-dividing phase outside of the cell cycle, but continue to perform their main functions for the rest of the organism's life. Post-mitotic cells include neuronal cells, heart muscle cells, and muscle cells. Some cell types in mature organisms, such as parenchymal cells of the liver and kidney, enter the G0 phase semi-permanently and can only be induced to begin dividing again under very specific circumstances. These types of cells can also be considered as post-mitotic cells when they are in G0 phase.

As used herein, the term "cdc13-1" refers to yeast mutant cells that contain a point mutation in the gene CDC13. The term "cdc13-1" also refers to the point mutant gene, while cdc13-1p refers to the protein produced by the point mutant gene cdc13-1, and Cdc13p refers to the wild type protein.

As used herein, the terms "cdc13-2", "stn-1", "cdc17-1", and "cdc17-2" refer to yeast mutant cells, or the corresponding mutant genes. The terms "est1", "est2", "est3", "hdf1", and "hdf2" refer to yeast mutant cells containing a deletion of the gene EST1, EST2, EST3, HDF1 or HDF2, respectively, or refer to the corresponding gene deletions respectively. A person of ordinary skill in the art would readily understand the usage of these terms within the context.

As used herein, the term "TOR inhibitor" refers a class of immunosuppressive compounds which contain the basic rapamycin nucleus, including rapamycin and chemically or biologically modified derivatives thereof, which retain the ability to maintain senescence. Accordingly, the term "TOR inhibitor" may be in the form of ester, ether, hydrazone, hydroxylamine, or oxime derivatives of rapamycin. The term may also include analogs of rapamycin through modification of the functional groups on the rapamycin nucleus, for example, through reduction or oxidation reactions. Thus, the term "TOR inhibitor" includes, but is not limited to rapamycin and analogs such as AP23573 (Deforolimus), AP-23675, AP-23841, ABT-578 (Zotarolimus), CCI779 (Temsirolimus), RAD-001 (Everolimus), 7-epi-rapamycin, 7-thiomethyl-rapamycin, 7-epi-trimethoxyphenyl-rapamycin, 7-epi-thiomethyl-rapamycin, and 7-demethoxy-rapamycin, 32-demethoxy-rapamycin, 2-desmethyl-rapamycin, and 42-O-(2-hydroxy)ethyl rapamycin.

As used herein, the term "therapeutic doses of rapamycin" means the dose range of rapamycin from about 1 mg/day to about 5 mg/day, which can be expanded to from about 0.1 mg/day to about 15 mg/day, but does not exceed 40 mg/day in clinic. Under these doses, rapamycin inhibits protein translation and cell cycle progress at G1 phase, as well as induces autophagy. In animal and tissue cultures, the therapeutic doses mean above 0.1 mg/kg/day in marine models, above 10 ng/mL for human cells and above 100 ng/mL for marine cells, respectively. It is understandable to a person of ordinary skill in the art that the exact therapeutic dose may vary for a specific cell line or animal.

As used herein, the term "low doses of rapamycin" means doses below "the therapeutic doses". For example, the low dose can be 0.1 to 1000 pM in serum medium for cells, 0.01 to 100 μg/kg/day in marine models, or 0.01 to 100 μg/day in humans. The specific concentration is dependent on the specific type of cells or diseases to be treated and the path of administration. These low doses can also be presented as about 0.001% to about 10% of therapeutic doses of rapamycin.

As used herein, the term "anti-aging biological concentration" of a compound or composition means the concentration of an anti-aging biologically active compound or composition, in contrast to concentration of a compound or composition. The anti-aging biological activity can be measured by senescence prolongation in cdc13-1 cells.

As used herein, the term "cancer" describes a diseased state in which a normal cell first becomes an abnormal cell with initial lesions such as DNA damages, oncogene activation, telomere dysfunction, and then becomes invasive to adjacent tissues, to regional lymph nodes and to distant sites. Cancer can be age-related cancers, mutagen-induced cancers, secondary cancers induced by anticancer therapies or therapies against an independent disorder or disease such as hormone replacement, or induced by environments such as UV, ironing irradiation, and smoking.

As used herein, the term "preventing tumorigenesis" means to inhibit the transformation of a normal cell into an abnormal cell, or to inhibit the formation of benign tumors. The term "preventing malignant progression" means to inhibit the development of benign tumors into malignant tumors or cancers. The term "preventing cancer" or "cancer prevention" means to prevent tumorigenesis and/or to inhibit malignant progression.

As used herein, the term "cancer chemopreventive agent" refers a natural or laboratory-made substance that can be used to inhibit tumor growth.

As used herein, the term "pharmaceutically acceptable carrier" refers to a carrier medium generally accepted in the art for the delivery of biologically active agents to animals, in particular, mammals, including, e.g., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents, and dispensing agents, depending on the nature of the mode of administration and dosage forms. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., as well known to those of ordinary skill in the art.

As used herein, the term "pharmaceutically acceptable salt" refers to a salt or zwitterionic form of a compound, which is water or oil-soluble or dispersible and, within the scope of sound medical judgment, suitable for use in contact with the tissues of a patient without excessive toxicity, irritation, allergic response, or other problem or complication commensurate with a reasonable benefit/risk ratio, and is effective for its intended use. Representative acid addition salts include acetate, adipate, alginate, citrate, aspartate, benzoate, benzenesulfonate, bisulfate, butyrate, camphorsulfonate; hemisulfate, heptanoate, hexanoate, formate, fumarate, hydrochloride, hydrobromide, hydroiodide, lactate, maleate, mesitylenesulfonate, methanesulfonate, naphthalenesulfonate, nicotinate, 2-naphthalenesulfonate, oxalate, palmate, pectinate, persulfate, pivalate, propionate, succinate, tartrate, trichloroacetate, trifluoroacetate, phosphate, glutamate, bicarbonate, p-toluenesulfonate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

The cations of pharmaceutically acceptable salts include lithium, sodium, potassium, calcium, magnesium, and aluminum, as well as nontoxic quaternary amine cations such as ammonium, tetramethylammonium, tetraethylammonium, tetrabutylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine. Other representative organic amines useful for the formation of base addition salts include ethylenediamine, ethanolamine, diethanolamine, piperidine, and piperazine.

As used herein, the term "solvate" means a physical association of a compound identified according to this invention with one or more, preferably one to three, solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

In addition, compounds encompassed by the present invention may have prodrug forms. Any compound that will be converted in vivo to provide the bioactive agent is a prodrug within the scope of the invention. Various forms of prodrugs are well known in the art. For examples of such prodrug derivatives, see *Design of Prodrugs*, edited by H. Bundgaard (Elsevier, 1985), and *Methods in Enzymology*, Vol. 112, at pp. 309-396, edited by K. Widder et al. (Academic Press, 1985); and *A Textbook of Drug Design and Development*, edited by Krosgaard-Larsen and H. Bundgaard, Chapter 5, "*Design and Application of Prodrugs*," by H. Bundgaard, at pp. 113-191 (1991).

As an illustrative example, compounds containing a hydroxyl group, such as rapamycin and its analogs, can form physiologically hydrolysable esters, carbonates, or carbomates that serve as prodrugs by being hydrolyzed in the body to yield the parent compounds. Thus, the present invention encompasses use of rapamycin and analogs or their corresponding ester, carbonate, or carbomate derivatives as anti-aging agents. These prodrugs can be synthesized by a person of ordinary skill in the art by using conventional synthetic methods known in the art. Just to illustrate, the esters include, but are not limited to, those derived from acylation of the hydroxyl group(s) with an acylating agent known to a person of ordinary skill in the art, for example, acetic anhydride, acetyl chloride, acetic acid, propionyl chloride, benzoyl chloride, butyryl chloride, succinic anhydride, and so on. The carbonates include, but are not limited to, those derived from reaction of the hydroxyl group(s) with a compound having a structure of formula X—C(O)OR, wherein X is a halide and R can be any group having a carbon attached to the oxygen atom, e.g., alkyl, aryl, arylalkyl, etc. Carbomates can also be synthesized in a similar manner.

In addition, prodrugs of rapamycin can also be in other forms as described in U.S. Pat. No. 4,650,803 and U.S. Pat. No. 5,151,413, or in any other literature published or yet to be published, which are herein incorporated by reference in their entirety. Most prodrugs described herein are preferably administered orally since hydrolysis in many instances occurs principally under the influence of the digestive enzymes. Parenteral administration may be used where a prodrug itself is active, or in those instances where hydrolysis occurs in the blood.

Formulations of the present invention may be administered in any suitable route known in the art, for example, by oral, topical, parenteral (including subcutaneous, intramuscular, intravenous and intradermal), and pulmonary route. In some embodiments, formulations are conveniently presented in unit dosage form and are prepared by any method known in the art of pharmacy. In general, the formulations are prepared by uniformly and intimately bringing into association of the active ingredient (e.g., rapamycin or analogs thereof) with liquid carriers or finely divided solid carriers or both.

Oral formulations containing the active compounds of this invention may comprise any conventionally used oral forms, including tablets, capsules, troches, buccal forms, lozenges and oral liquids, suspensions, or solutions, or as a powder or granules, a solution or suspension in an aqueous or non-aqueous liquid, an oil-in-water liquid emulsion, or a water-in-oil liquid emulsion. Capsules may contain mixtures of the active compound(s) with inert fillers and/or diluents. Useful tablet formulations may be made by conventional compression, wet or dry granulation methods, and may utilize pharmaceutically acceptable diluents, binding agents, disintegrants, lubricants, surface modifying agents (including surfactants), or suspending or stabilizing agents. Oral formulations may utilize standard delay or time release formulations to alter the absorption of the active compound(s).

In some cases it may be desirable to administer the compounds in the form of an aerosol directly to the airways, ears, skin, or throat.

Rapamycin at a low dose may also be administered topically. The topical forms include, but are not limited to, creams, ointments, emulsions, gels, lotions, and sprays. In one embodiment of the topical formulations of the invention, the topical formulation comprises inert materials (such as oil). In one embodiment of the topical formulations of the invention, the ingredients of the topical formulation are provided in a moisturizing cream base. Preservatives may also be provided in the topical formulations of the invention to increase the formulation's shelf life. Those skilled in the art would know how to modify the topical formulations of the invention by adding additional active ingredients or inert materials. The topical formulations of the invention may be used to prevent skin aging and to treat early stages of disorders such as cancers.

In some embodiments, tablets comprise at least one active ingredient and optionally one or more pharmaceutically acceptable carriers made by compressing or molding the respective agents. In preferred embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent.

The compounds or compositions of the present invention can be administered alone or in combination with one or more, preferably one to three, additional therapeutic agents. By "administered in combination" or "combination therapy" it is meant that the compound or composition of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that throughout the application data is provided in a number of different formats and that these data represent endpoints and starting points and ranges for any combination of the data points. For example, if a particular data point "2%" and a particular data point "4%" are disclosed, it is understood that greater than, greater than or equal to, less than, less than or equal to, and equal to 2% and 4% are considered disclosed as well as between 2% and 4%. It is also understood that each unit between two particular units are also disclosed. When the term "about" appears in front of a number denoting dosage, it means that the value can vary by at least ±30%, preferably by within ±20%, and more preferably by within ±10%; when the term appears in front of a number denoting temperature, it means that the value can vary by at least ±2° C., and more preferably by within ±1° C.; when denoting time, it means that the value can vary by at least 15%, preferably by within 10%, and more preferably by within 5%.

Methods of Identifying, Detecting and Purifying Anti-Aging Agents

This invention is based on various discoveries discussed below.

A. Inhibition of Nutrient Signals Prolongs the Cell Cycle-Arrested State Induced by Telomere Dysfunction in Yeast Via the AMPK and Subsequent Mitochondrial Pathway.

A-1. Inhibition of Nutrient Signals Maintains the Cell Cycle-Arrested State and Thus Prevents Subsequent Cell Death Induced by Telomere Dysfunction.

The budding yeast cdc13-1 is an important model of telomere dysfunction based on the various reasons. For example, first, the telomere dysfunction induced by inactivation of cdc13-1p leads to the same downstream pathway as that by inactivation of telomerase: Mec1 (ATM and ATR homologue)-dependent cell cycle arrest at G2/M followed by massive cell death, which is accompanied by enlarged cell size, dramatically increased ROS production, apoptotic markers, and more than 2N DNA content in haploid cells. Inhibition of TOR by rapamycin prevents the cell death induced by inactivation of cdc13-1p or by inactivation of telomerase. Interestingly, rapamycin does not affect the G2/M arrest triggered by inactivation of cdc13-1p, but maintains the G2/M-arrested state and thus prevents the appearance of >2N DNA content, an indicator of deterioration of senescence and cell death (Qi, H., et al., *PLoS ONE*, 3, e3520 (2008)). Second, telomere structure and function are conserved from yeast to human. In human cells, telomere dysfunction also leads to ATM-/ATR-dependent cell cycle arrest followed by massive cell death manifested by enlarged cell size, apoptotic markers and polyploidy (Denchi, E. L., et al, *Nature*, 448:1068-71 (2007); Shay, J. W., et al, *Carcinogenesis*, 26:867-74 (2005)), similar to that in cdc13-1. Thus, cdc13-1 can be used to study telomere dysfunction-induced downstream cascade.

Figure 1B:
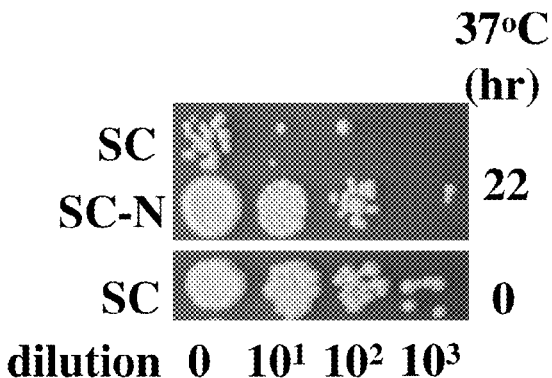
Figure 1C:
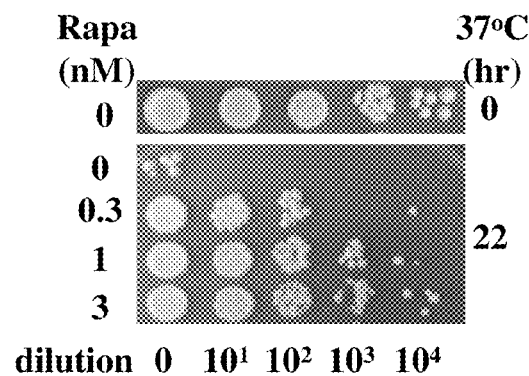
Figure 1D:
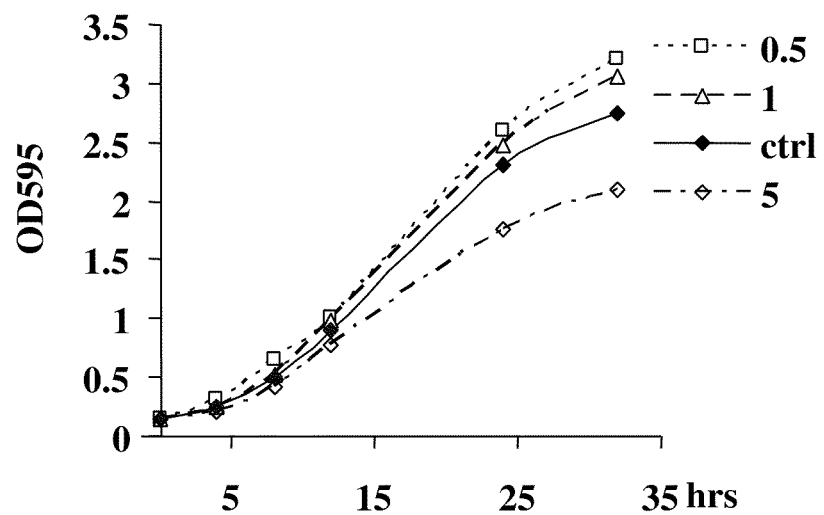
Figure 1E:
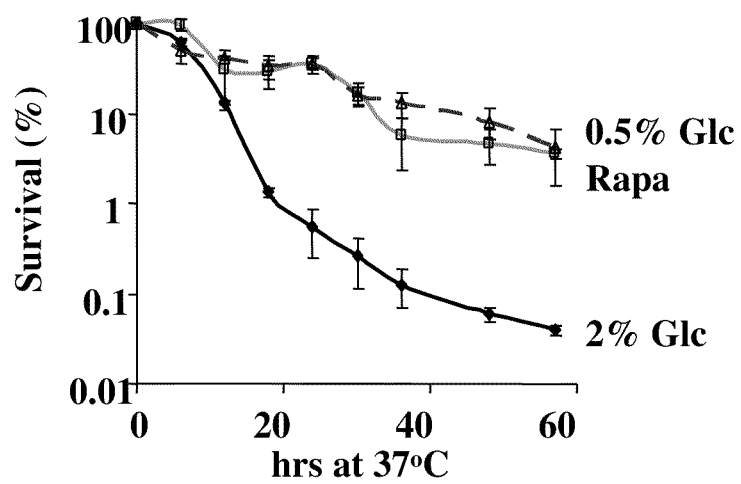

This invention discloses that, similar to a rapamycin treatment, the glucose restriction by reducing glucose in the yeast culture medium or by addition of 200 µM 2-deoxyglucose (an analogue of glucose) to the medium, and the nitrogen limitation also prevented cell death induced by inactivation of cdc13-1p as monitored by the colony formation assay. As shown in FIG. 1A, incubation of cdc13-1 cells (haploid) at the non-permissive temperature (37° C.) for 22 hrs in regular YEPD medium (1% peptone, 2% yeast extract, and 2% glucose) resulted in massive loss of viable cells as measured by the colony formation assay. However, reducing glucose in YEPD medium (from 2% to 1%, 0.5% and 0%) and addition of 200 µM 2-deoxy-glucose to YEPD with 2% glucose prevented cell death effectively: less glucose, more survived cells. In addition, limitation of nitrogen by SC-N medium (containing 0.67% yeast nitrogen base in absence of amino acids and $(NH_4)_2SO_4$, 2% glucose, plus a mixture of 100 mg/L each of histidine, leucine, tryptophan and uracil for this yeast strain) prevented the cell death (FIG. 1B). Furthermore, the cdc13-1 cell death was prevented by rapamycin in a dose-dependent manner when the concentrations were between 0.3 to 1 nM (FIG. 1C). 0.5 and 1 nM of rapamycin that prevented the cell death did not inhibit, but slightly promoted, cell growth consistently (FIG. 1D), indicating a novel function of rapamycin at a low dose. FIG. 1E shows that rapamycin and glucose restriction delay cdc13-1 cell death. In contrast to dramatic cell loss after 20 hrs at 37° C., low doses of rapamycin and glucose restriction resulted in a slow-loss of cells. After 60 hrs of incubation at 37° C., cell survival was at least 100-fold more than those without treatment.

Figure 2A:
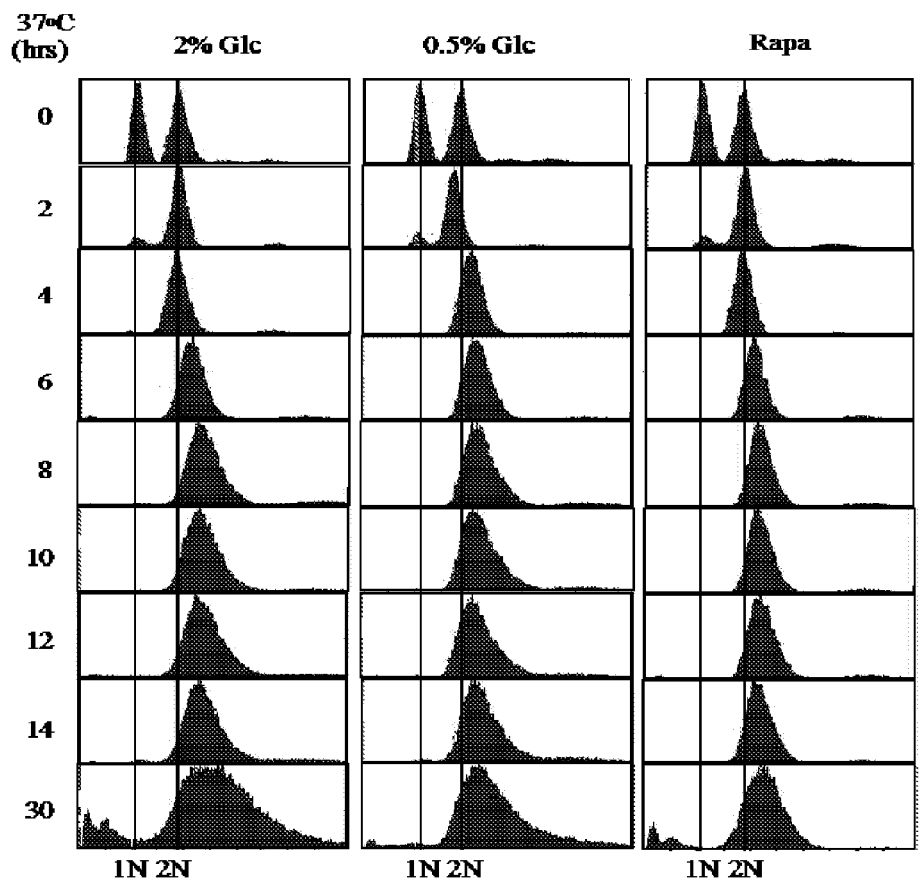
FIG. 2 shows that nutrient signaling does not interfere with the cell cycle arrest at G2/M, but maintains the G2/M-arrested state and prevents cell death induced by inactivation of cdc13-1p. (A) Cells were incubated at 37° C. to inactivated cdc13-1p, in YEPD medium, YEPD+1 nM rapamycin or YEPD with 0.5% glucose. At the indicated time points, an aliquot of cells was taken out and fixed with 50% ethanol at −20° C. for about 4 hrs, and then digested with 0.2 mg/mL RNase A in 50 mM Tris pH 7.6 at 37° C. overnight. The cells were next washed with 50 mM Tris pH 7.6 and treated with 40 µg/mL proteinase K at 55° C. for 2 hrs. After being washed again, cells were stained with 100 µg/mL propidium iodide for 20 min in the dark prior to FACS (Fluorescence activated cell sorter) analysis. (B) Cell survival assay shows that the death of G2/M cells induced by inactivation of cdc13-1p for 2 hrs can still be prevented by rapamycin and glucose restriction. Cells were incubated at 37° C. for 2 hours first, then diluted with a 37° C-YEPD medium, YEPD with rapamycin to make a final concentration of 1 nM, or with a 37° C-medium without glucose to make final 0.5% glucose. The cells were continuously incubated at 37° C. for 22 hrs. Surviving cells were counted using the colony formation assay.
Figure 2B:
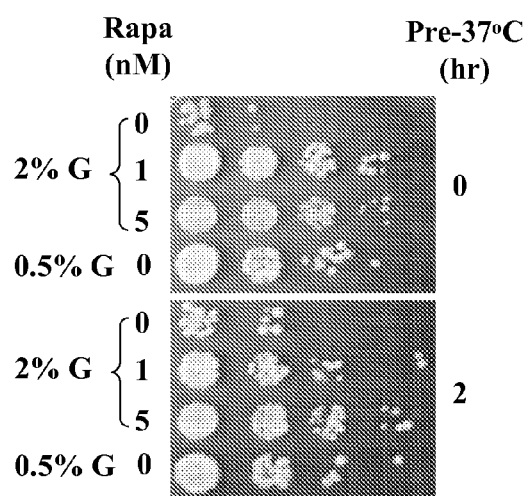

The results further demonstrate that glucose restriction, similar to rapamycin treatment, maintains the G2/M-arrested state and prevents subsequent cell death induced by inactivation of cdc13-1p. As shown in FIG. 2A, after incubating cdc13-1 cells at the non-permissive temperature (37° C.) for 2 hrs, more than 95% of cells entered the G2/M phase of cell cycle in glucose restriction (0.5% glucose) and rapamycin (1 nM) containing YEPD medium, similar to that in the control. Glucose reduction from 2% to 0.5% in YEPD medium inhibited the increase of >2N DNA content, suggesting maintenance of the cell cycle-arrested state, same as the rapamycin treatment (1 nM). As shown in FIG. 2B, pre-incubation of cdc13-1 cells at 37° C. for two hrs, which allows greater than 95% of cells to enter the G2/M phase of cell cycle, did not affect the preventive effect of glucose restriction and rapamycin on the cell survival. Thus, nutrient limitation, similar to TOR inhibition by rapamycin, maintains the cell cycle-arrested state (the senescent state), and thus prevents the deterioration of senescence and the resulting cell death upon telomere dysfunction.

A-2. Glucose Restriction, Same as TOR Inhibition by Rapamycin, Prevents the Induction of ROS and Inhibits the Appearance of Apoptotic Markers in cdc13-1 Cell Death.

Figure 3A:
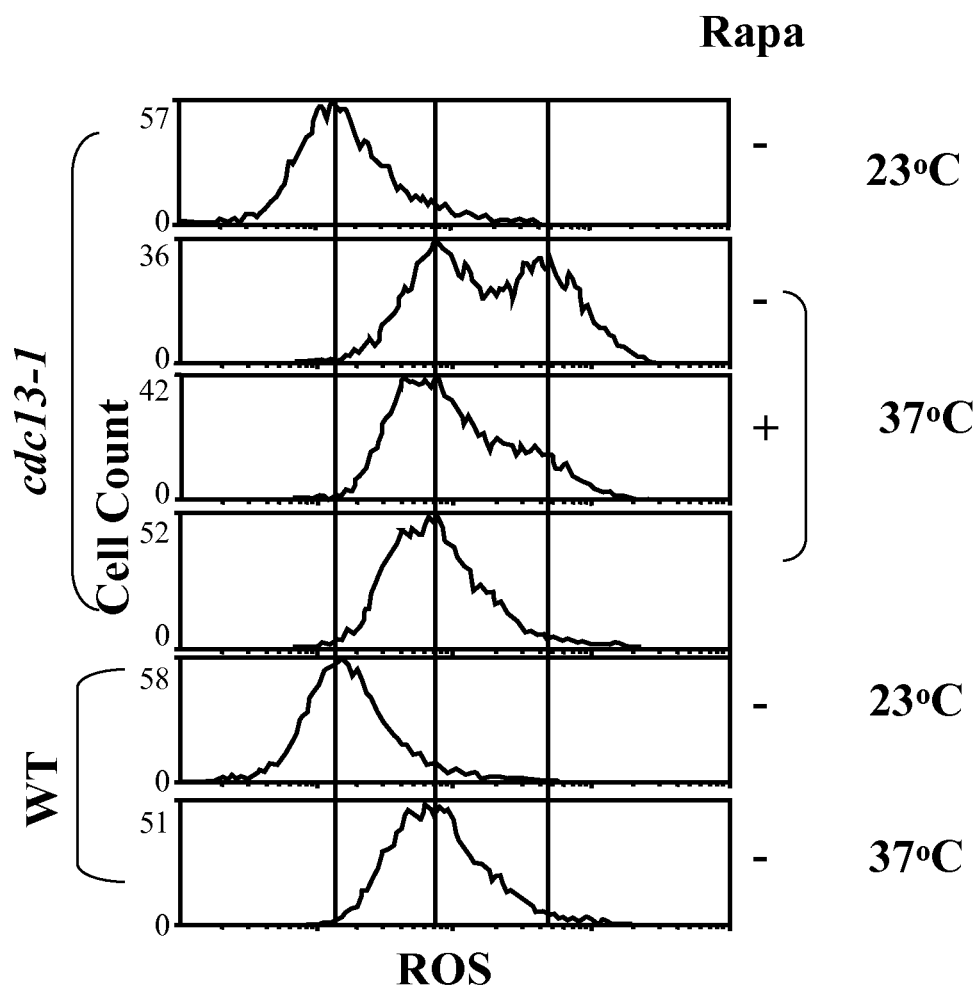
FIG. 3 shows that rapamycin (1 nM) and reduced glucose (0.5%) decrease ROS production by inactivation of cdc13-1p as measured by dihydrorhodamine 123 (Invitrogene) staining followed by FACS analysis (A) and decrease an apoptotic marker PS flipping as measured by annexin V-FITC binding followed by FACS analysis (B). Cells were treated under conditions as described in FIG. 1A and FIG. 1C. To measure ROS levels, the treated cells were incubated with 5 µg/mL dihydrorhodamine 123 in YEPD for 1 hr prior to FACS analysis. 10,000 cells were analyzed for each sample. To measure PS flipping, the treated cells were resuspended in a PBS buffer containing 1.1 M sorbitol and 2 mg/mL Zymolyase, and incubated at 37° C. for 20 min. The cells were then stained with annexin V-FITC and propidium iodide (PI) (BD Biosciences Pharmingen) in PBS (Phosphate Buffered Saline) containing 1.1 M sorbitol, followed by FACS analysis. 10,000 cells were analyzed for each sample. Under these conditions, the PI-negative population represents intact cells, the PI-negative-FITC-positive cells represent the apoptotic population, and the PI-positive-FITC positive cells represent the late apoptotic or necrosis population.
Figure 3B:
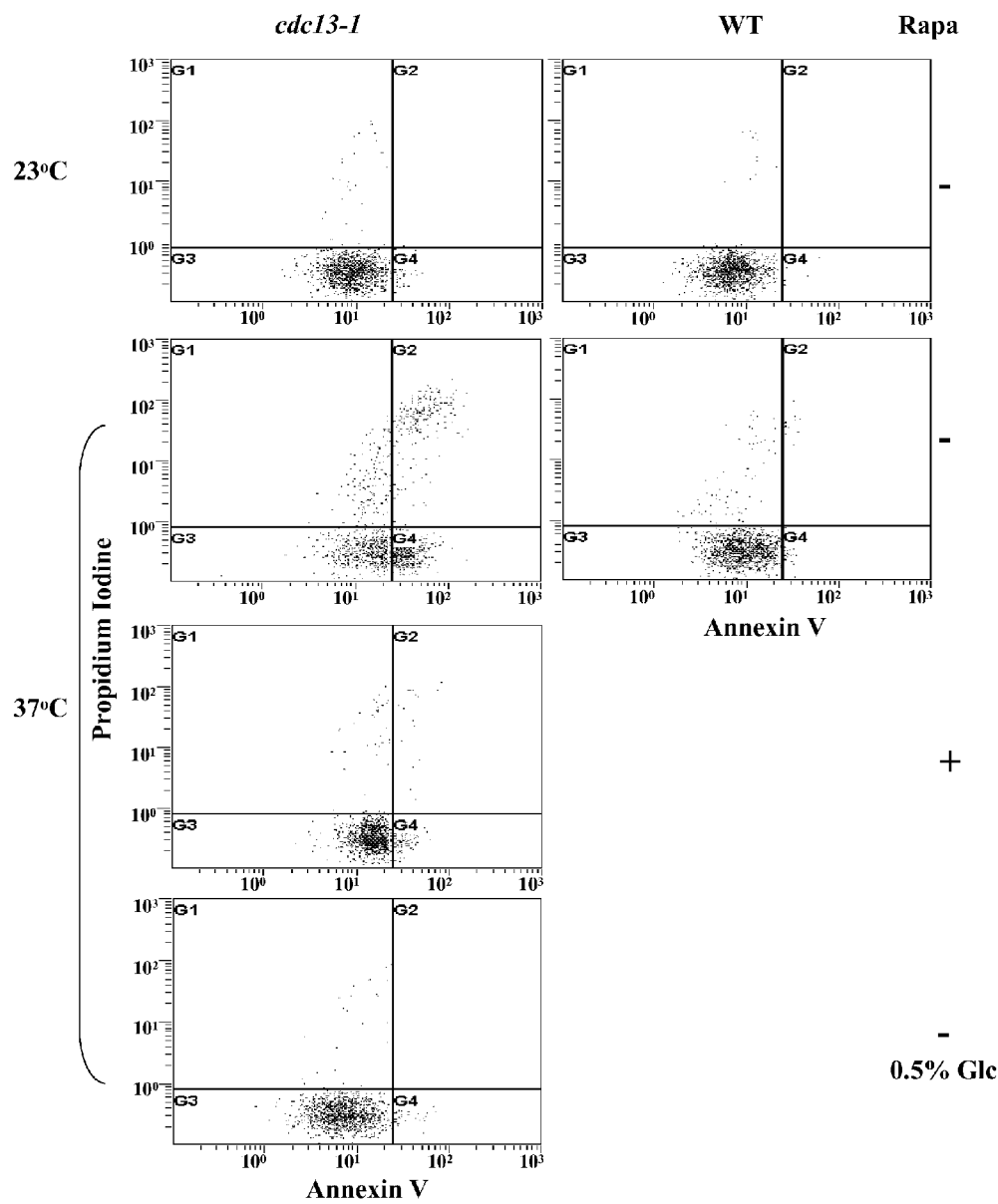

FIG. 3A shows that cdc13-1 cell death is associated with a dramatic increase in ROS release. Similar to rapamycin (1 nM) treatment, reduction of glucose from 2% to 0.5% (0.5% Glc), effectively reduced ROS increase to a level comparable to that of wild type (WT) at the same temperature. FIG. 3B shows that cell death induced by inactivation of cdc13-1p is also associated with increased apoptosis as monitored by phosphatidylserine (PS) flipping and glucose reduction (0.5% Glc) or rapamycin (1 nM) effectively inhibits this apoptotic death.

A-3. AMPK and Mitochondrial Function Play Important Roles in the Preventive Effects of Rapamycin and Glucose Restriction on the cdc13-1 Cell Death.

Figure 4A:
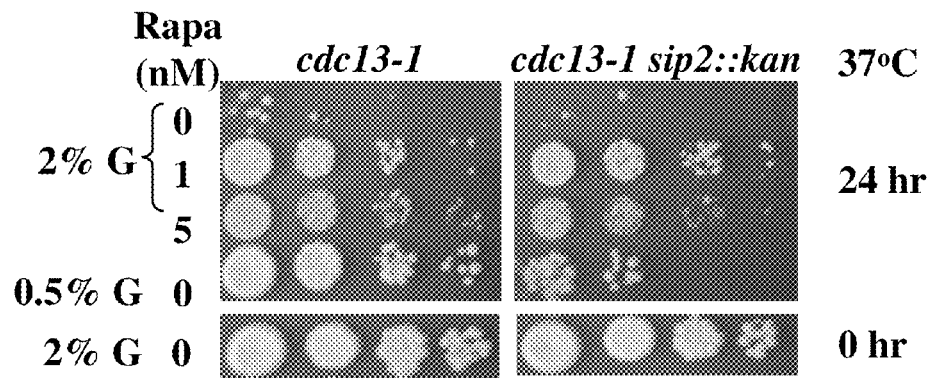
FIG. 4 shows that rapamycin and glucose restriction prevent cell death induced by inactivation of cdc13-1p through AMPK. (A) Deletion of the AMPK regulatory subunit Sip2p abolishes the preventive effect of glucose restriction. (B) Deletion of the AMPK catalytic subunit Snf1p and the regulatory subunit Snf4p significantly decreases the preventive effect of rapamycin (1 nM). The cdc13-1sip2::Kan, cdc13-1snf1::Kan and cdc13-1snf4::Kan double mutant strains were generated by mating the single deletion mutant from the deletion library (from Invitrogen, Carlsbad, Calif.) with cdc13-1, followed by sporulating the diploid and selecting for temperature-sensitive and G418 (200 µg/mL)-resistant colonies. Cells were treated as in FIG. 1A and FIG. 1C. Surviving cells were monitored by the colony formation assay.
Figure 4B:
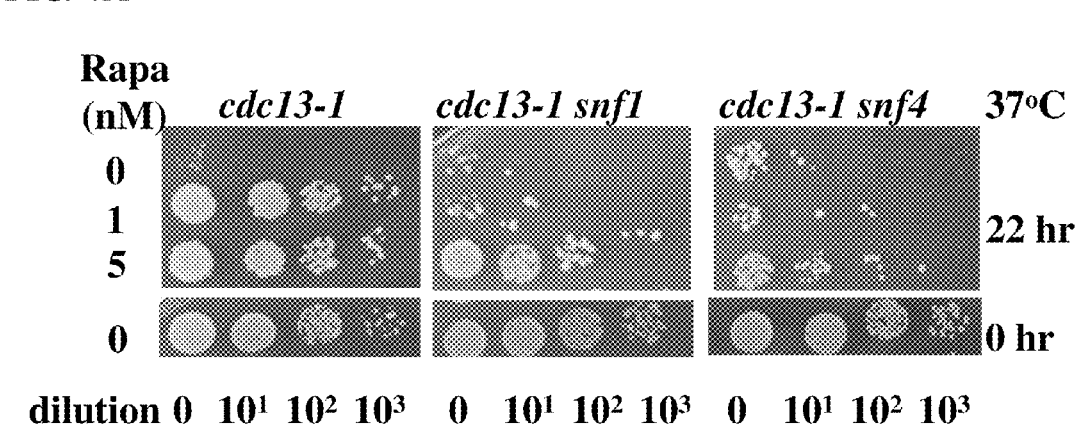

This invention also discloses the important role of AMPK for the preventive effects on the cdc13-1 cell death. FIG. 4A shows that deletion of Sip2p, the regulatory beta subunit of yeast AMPK, significantly inhibited the prevention effect of glucose restriction. Furthermore, deletion of Snf1p and Snf4p, the catalytic alpha subunit and the regulatory gamma subunit respectively, greatly reduced the preventive effect of rapamycin (FIG. 4B).

Figure 5A:
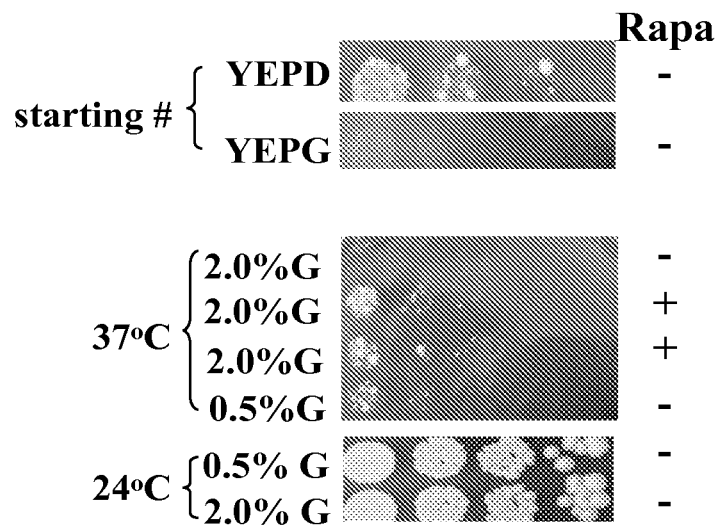
FIG. 5 shows that mitochondria play an important role in the preventive effect of nutrient limitation on cdc13-1 cell death. (A) Mitochondria deficiency significantly inhibits the preventive effect of rapamycin and glucose restriction. Mitochondria deficient mutant ρ° was generated in cdc13-1 by growing cells in an ethidium containing YC medium to log phase for two days as described (Qi, H., et al, *J. Biol. Chem.*, 278: 15136-15141 (2003)). The cells were treated as indicated and as described in FIG. 1A and FIG. 1C. Surviving cells were monitored by colony formation assay. (B-C) Glucose restriction and rapamycin treatment increase mitochondrial mass. Fresh diluted overnight cultures in YEPD, YEPD+ rapamycin (B) or YEPD, 0.5% glucose YEPD (C) were incubated at 24° C. to for 4 hrs to log phase. Mitochondrial mass was measured by staining the 60%-ethanol fixed cells using MitoTracker Green FM, followed by FACS analysis.
Figure 5B:
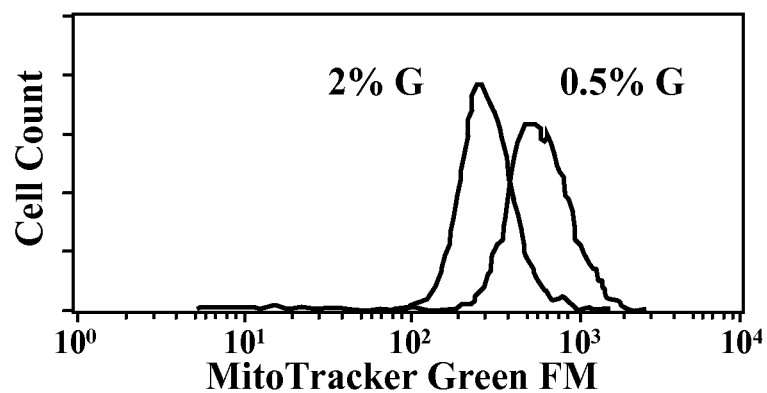
Figure 5C:
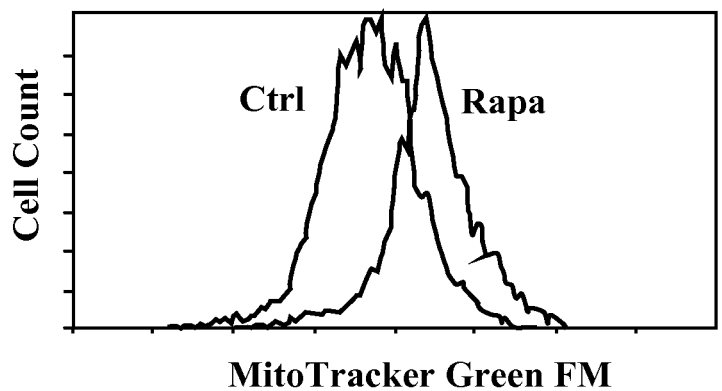

This invention further discloses that mitochondria, whose function can be improved by AMPK activation and the downstream mitochondrial biogenesis, play an important role in the preventive effects on the cdc13-1 cell death. The mitochondrial deficient mutation was made in cdc13-1 cells by incubating cells in ethidium bromide containing medium as described in a previous published paper (Qi, H., *J. Biol. Chem.*, 278:15136-15141 (2003)). FIG. 5 shows that the mitochondria deficiency significantly abolished the preventive effect by glucose reduction and rapamycin (at 1 nM and 5 nM). Up-regulation of mitochondrial biogenesis by glucose reduction (0.5% glucose) and rapamycin (1 nM) was also demonstrated by measuring the increase of mitochondrial mass (FIG. 5B and FIG. 5C).

Figure 6:
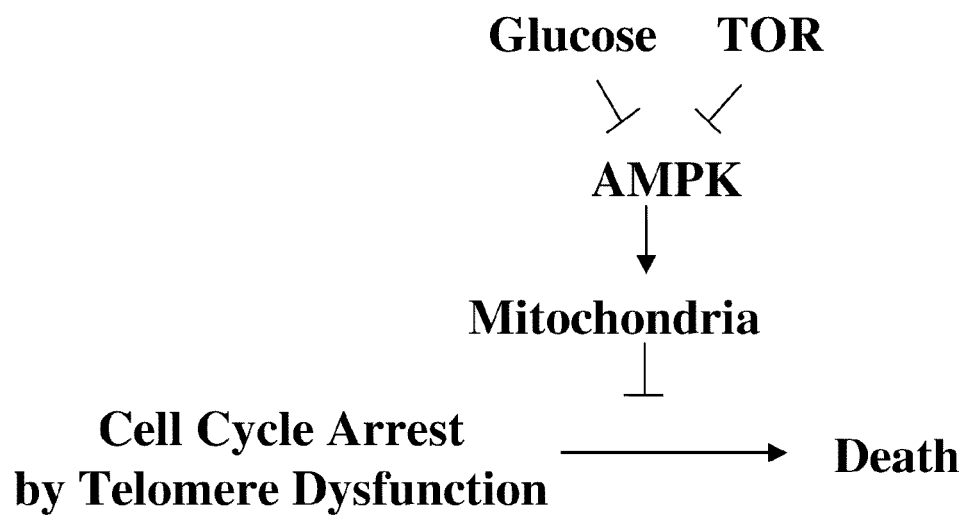
FIG. 6 shows the mechanism of nutrient signaling through TOR, AMPK, and mitochondria in maintaining the cell cycle-arrested state and preventing cell death induced by telomere dysfunction in the cdc13-1 model.

FIG. 6 shows the summary of above results. Mitochondria play an important role in maintaining the growth-arrested state induced by telomere dysfunction, and glucose restriction and TOR inhibition by rapamycin stimulate mitochondrial function through AMPK activation, thus prevent deterioration of senescence and subsequent cell death.

B. Low Doses of Rapamycin, Glucose Restriction, and an AMPK Activator, in a Similar Manner, Stimulate Mitochondrial Function and Prolong Senescence in Primary Human Fibroblasts.

Figure 7:
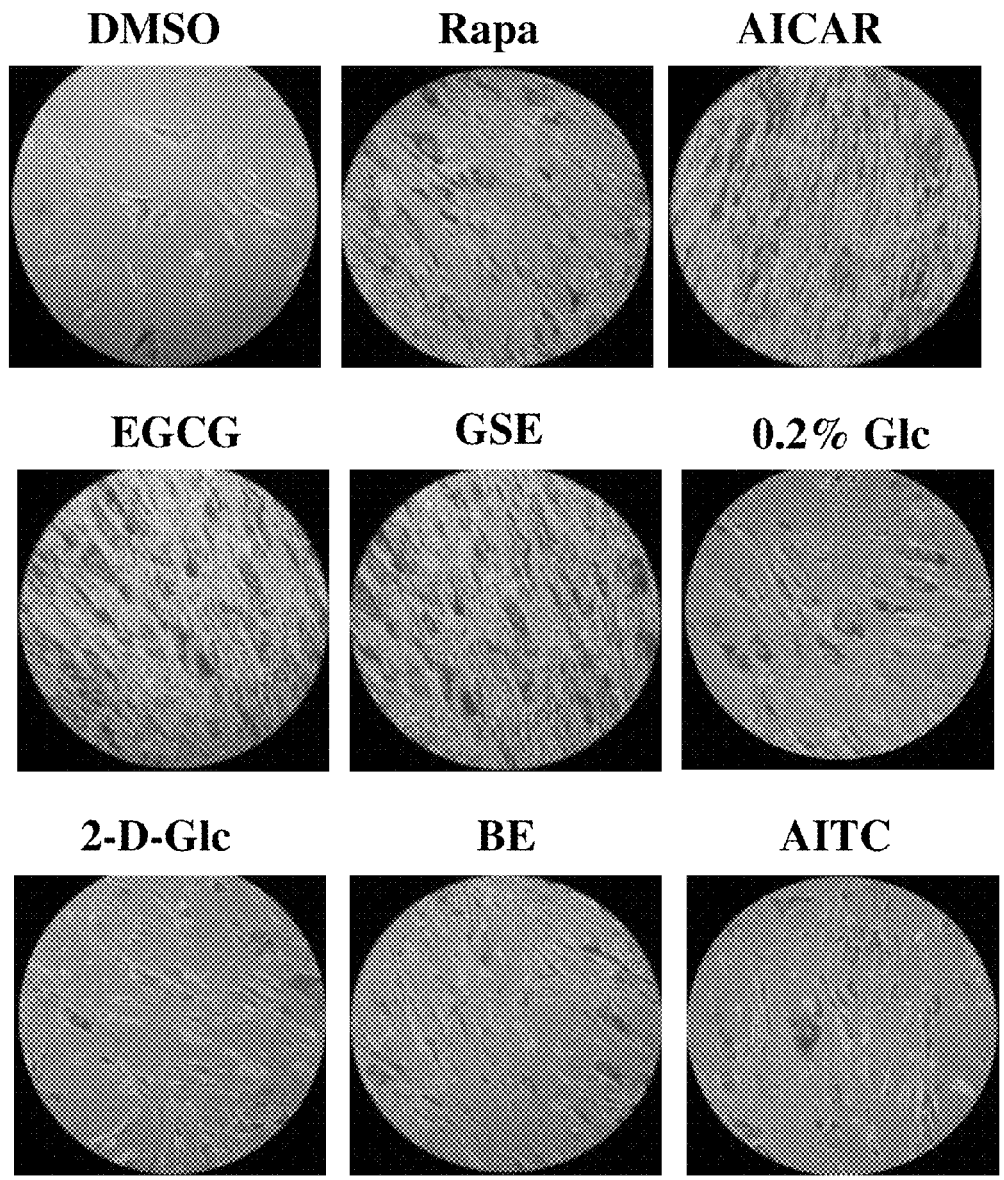
FIG. 7 shows that the loss of the senescent WI-38 cells (human primary fibroblast) is prevented by the treatment of 50 pM rapamycin, 250 µM AICAR, 20 µg/mL EGCG, 1.6 µg/mL GSE, reduced glucose (from 0.4% to 0.2%), 20 µg/mL bilberry extract (BE), 1 µM AITC, and 12.5 µM 2-deoxyglucose. AICAR and reduced glucose treatment were incubated with cells in a 2-day-on/8-day-off cycle, while the rest of agents were in a 3-day-on/7-day-off cycle. The treatment started at passage 29. The medium was refreshed every 3 days. After 56-days from passage 31 (senescence), the cells were briefly fixed in 2% formaldehyde/0.2% glutaraldehyde and stained with 1 mg/mL 5-bromo-4-chloro-3-indolyl β-D-galactoside (X-gal) (in buffer containing 40 mM citric acid/sodium phosphate, pH 6.0, 5 mM potassium ferrocyanide, 5 mM potassium ferricyanide, 150 mM NaCl, and 2 mM $MgCl_2$) at 37° C. for 18 hrs for the senescence marker, cellular β-galactosidase activity (blue in color picture and dark grey in black/white picture). Surviving senescent cells were viewed under a microscope.

This invention discloses that CR or rapamycin also prolongs senescence and prevents cell death induced by telomere dysfunction in human cells. Primary human embryonic lung fibroblasts WI-38 were used. These cells lack telomerase activity and exhibit telomere dysfunction upon reaching replication potential, usually at passage 31 under routine culture conditions. Cells at passage 29 were treated with 50 pM rapamycin. The treatment was on a 10-day cycle of 3-day with and 7-day without rapamycin (also termed as 3-day-on/7-day-off cycle). Cells ceased dividing at passage 31 (examined under a microscope) and exhibited senescence in the presence or absence of rapamycin by measuring the cytosol β-galactosidase activity using 5-Bromo-4-chloro-3-indolyl β-D-galactoside (X-gal) in buffer containing 1 mg/mL X-gal, 40 mM citric acid/sodium phosphate, pH 6.0, 5 mM potassium ferrocyanide, 5 mM potassium ferricyanide, 150 mM NaCl, and 2 mM $MgCl_2$. Due to increased cytosol β-galactosidase activity, senescent cells are stained a blue color (shown as dark grey in black/white picture). FIG. 7 shows that after 56-days in senescence, massive cell loss occurred in the DMSO control. Cell loss was strongly inhibited by 50 pM rapamycin. Rapamycin didn't transform cells since the senescence marker was still present and cell growth was not observed. In addition, reduced glucose in the culture medium (from 0.4% to 0.2%) or addition of 2-deoxyglucose (12.5 µM) also prevented loss of senescent cells (FIG. 7).

Figure 8A:
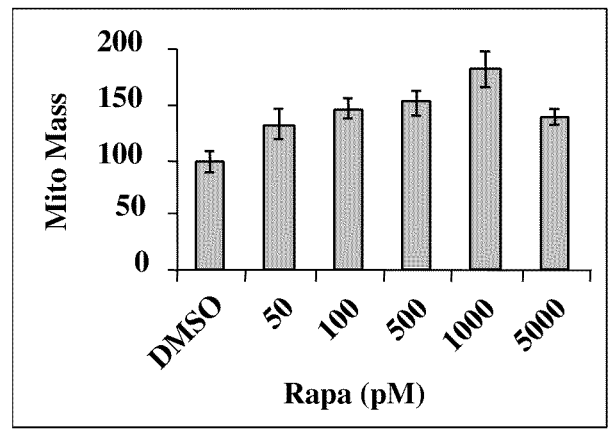
FIG. 8 shows that low doses of rapamycin increase mitochondrial mass, improve mitochondrial membrane potential and decrease ROS levels in human fibroblasts. (A) WI-38 cells at passage 24 were treated with various doses of rapamycin in culture medium for 2 days. For mitochondrial mass measurements, the cells were fixed with 60% ethanol at −20° C., and then stained with MitoTracker Green FM (Invitrogene) for 30 min prior to FACS analysis. (B) Human lymphoblastoid L40 cells were treated with various doses of rapamycin for two days. For mitochondrial membrane potential measurement, the treated cells were stained with 5 µg/mL JC-1 (Invitrogen) in the dark for 15 min. Cells were then washed with PBS once, followed by FACS analysis. Photomultiplier settings were adjusted to detect green fluorescence ($\lambda_{em}$=525 nm) of JC-1 monomer using filter 1 (FL-1 detector) and the red fluorescence ($\lambda_{em}$=590 nm) of JC-1 aggregates using filter 2 (FL2 detector). The ratio of JC-1 aggregate/monomer (red/green or FL2/FL1) is indicative of the membrane potential. Data was collected from normal cell populations for each sample, which was gated according to the non-treatment controls based on forward and side scatters. (C) For ROS measurement, L40 treated cells were stained with 2 µg/mL of dehydrorhodamine 123 for 30 min before FACS analysis. In each experiment above, at least 10,000 events were analyzed. The data represents the average of a duplica-experiment.
Figure 8B:
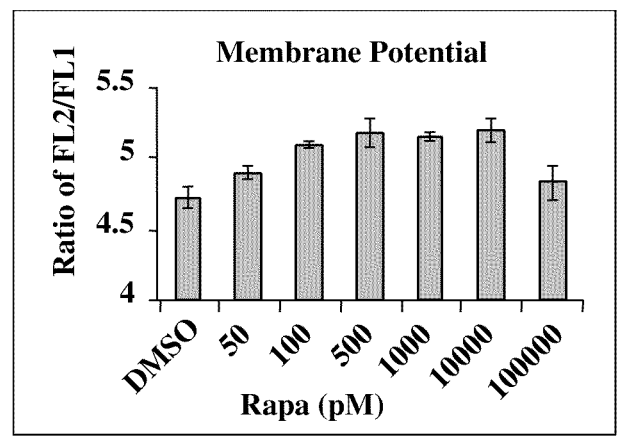
Figure 8C:
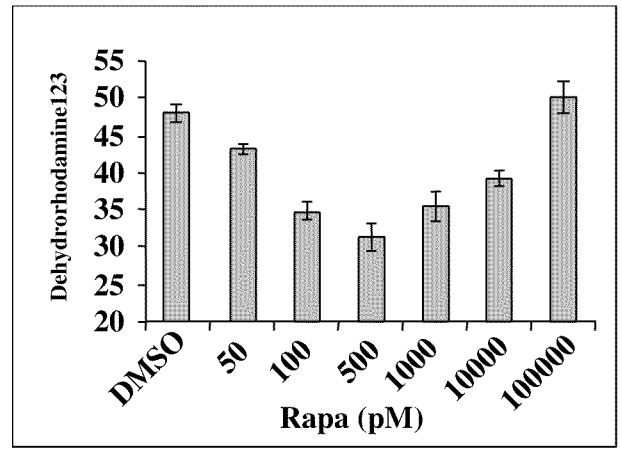
Figure 10A:
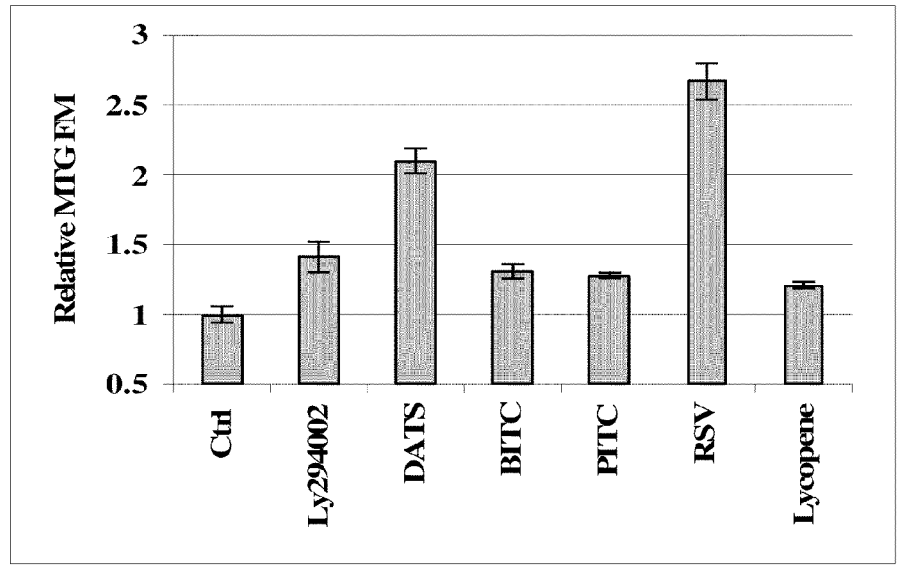
FIG. 10 shows that mitochondrial mass is increased in human lymphoblastoid L40 by a 2-day treatment with (A) 10 μM LY294002 (a PI3K inhibitor), 2 μM diallyl trisulfide (DATS), 1 μM benzyl isothiocyanate (BITC), 1 μM phenyl isothiocyanate (PITC), 2 μg/mL resveratrol (RSV) and 0.03 μM lycopene, and (B) with 6.7 μM PEITC, 5 mM silibinin, 1.25 mM selenite, 2.5 mM genistein, 250 μg/mL grape seed extract (GSE), 50 μg/mL EGCG, 3 mg/mL bilberry extract (BE), 1 μM AITC 50 pM rapamycin 250 μM AICAR, and reduced glucose (from 0.4% to 0.2%). Mitochondrial mass was monitored by staining the 60% Ethanol-fixed cells with MitoTracker Green FM prior to FACS analysis.
Figure 10B:
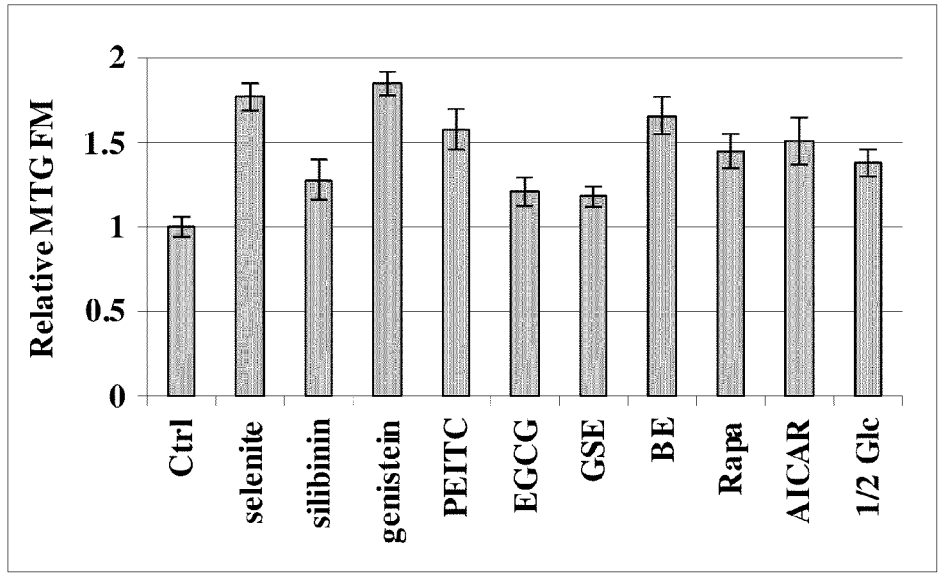

Similar to the observation in yeast, AMPK also plays an important role in rapamycin- or glucose restriction-mediated prevention of telomere-death in human cells. As shown in FIG. 7, treatment with AMPK specific activator 5-aminoimidazole-4-carboxamide-1-beta-D-ribofuranoside (AICAR, 250 µM) (in a 10-day cycle of 2-day with and 8-day without AICAR to avoid toxicity) prevented the loss of senescent WI-38 cells. In addition, Rapamycin (50 pM) activated AMPK kinase activity as monitored by Western blotting, which was used to detect the phosphorylated AMPK at Thr172 (data not shown). Furthermore, rapamycin, reduced glucose, 2-deoxyglucose, and AICAR increased mitochondrial mass and stimulated mitochondrial function in humans (FIG. 8 and FIG. 10). Low doses of rapamycin increased mitochondrial mass in human fibroblasts (FIG. 8A) as well as in lymphoblastoid L40 cells (data not shown). Rapamycin at low doses also increased mitochondrial membrane potential and reduced ROS in fibroblasts and in L40 cells (FIG. 8B, FIG. 8C, and data not shown).

Figure 9A:
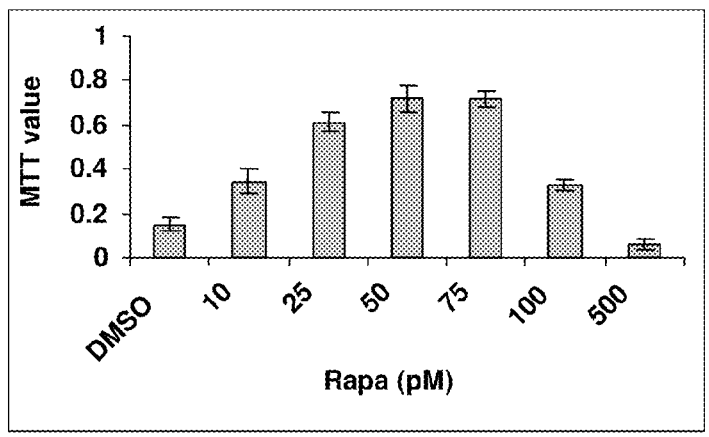
FIG. 9 shows that only low doses of rapamycin (below the growth inhibition doses) prevent the loss of senescent WI-38 cells. (A) WI-38 cells were treated with the indicated concentrations of rapamycin as in FIG. 7. The treatment started at passage 29. Cells entered senescence at passage 31. After 65-days in senescence, surviving cells were measured by MTT (3-(4,5-dimethylthiazol-2-yl)-2,5-diphenyltetrazolium bromide, a tetrazole) staining. The purple color of MTT generated by mitochondrial reductase was read in 570 nm by a microplate reader. The data is a representative of three independent duplica-experiments. (B) The effect of rapamycin on growth of WI-38 cells. Cells were cultured as in FIG. 7. Arrows indicate the time point when rapamycin was added. 25 pM rapamycin has little effect on growth rate, but increases the population doubling (PD) from 5.18 to 6.82. Population doublings were calculated using the following formula: PD=log($N_f/N_0$)/log2, where $N_f$ is the final cell number and $N_0$ is the number of initially seeded cells. Data is a representative of two independent duplica-experiments. (C) The low doses of rapamycin increase protein levels of p53, p21 and pRB. WI-38 cells on the $20^{th}$ day after the last split (senescence) were treated with rapamycin for 18 hrs. Cell lysates were then analyzed by Western blotting using antibodies specifically against p53, p21 or pRB.
Figure 9B:
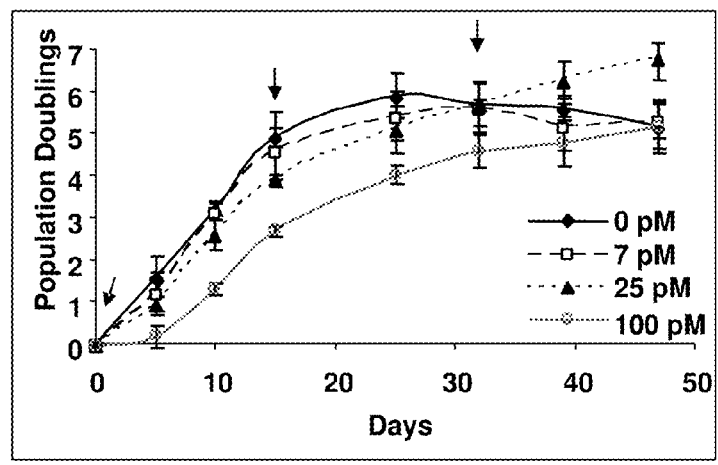
Figure 9C:
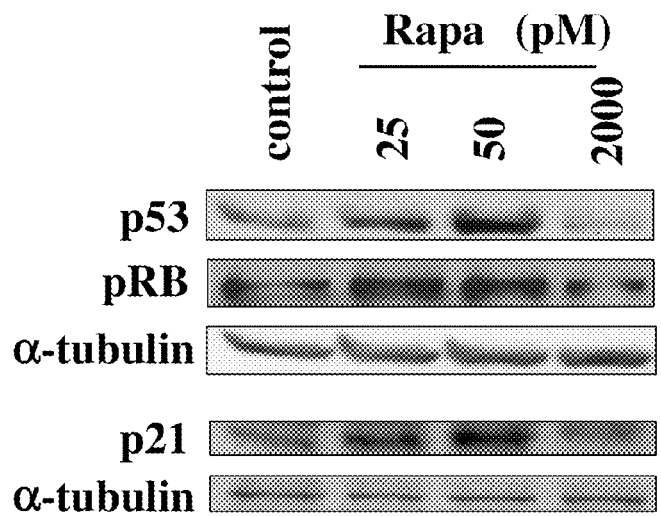

Surprisingly, only low doses of rapamycin (from 10 to 100 pM) prevented the loss of senescent WI-38 cells as shown in FIG. 9A. Rather, rapamycin at a concentration higher than 500 pM promoted cell loss. For example, 25 pM rapamycin prevented cell loss (FIG. 9A), but did not inhibit cell growth (FIG. 9B). Instead, it increased the replication potential as measured by population doubling from 5.12 to 6.8. In addition, rapamycin at low doses (50 pM and 100 pM) increased the levels of the key senescence proteins p53, p21 and pRB, but not at a high dose (2000 pM) (FIG. 9C). Furthermore, only low doses of rapamycin increased mitochondrial mass and membrane potential and reduced ROS levels in human cells, whereas an amount greater than 10 nM of rapamycin appears to lose this effect (FIG. 8). Thus, rapamycin at low doses functions differently from that of therapeutic doses, it stimulates mitochondrial function and prevents deterioration of senescence, rather than inhibiting protein translation and cell growth at cell cycle G1 phase.

In summary, 1) the maintenance of the cell cycle-arrested state in senescent cells is conserved from yeast to human; 2) CR, glucose restriction or a low dose of rapamycin stimulates mitochondrial function via AMPK, prolongs senescence and thus inhibits the subsequent cell death; and 3) only low doses of rapamycin mimic caloric restriction in terms of maintaining the senescent state in human cells.

C. Several Anti-Aging and Cancer Chemopreventive Agents Stimulate Mitochondrial Function and Inhibit Loss of Senescent Cells in Both Yeast and Human Cells.

This invention discloses that two agents known to prevent a number of age-related diseases, EGCG from Green tea extract (GTE) and Grape seed extract (GSE), can increase mitochondrial mass and prolong senescence.

GTE has been reported to prevent various cancers (U.S. Pat. Nos. 7,192,612 and 7,384,655, and US Application Publication Nos. 20040142048 and 20040047921, and Shimizu, M., et al., *Cancer Epidemiol. Biomarkers Prev.*, 17:3020-3025 (2008); Nakachi, K., et al., *Jpn. J. Cancer Res.*, 89:254-261 (1998)). Epigallocatechin gallate (EGCG) is the most effective components of GTE. EGCG has been reported to extend life span in *C. elegans* (Abbas, S. and Wink, M., *Planta. Med.*, 75:216-221 (2009)). It has also been reported to modulates amyloid precursor protein cleavage and reduces cerebral amyloidosis in Alzheimer transgenic mice (Rezai-Zadeh, K., et al., *J. Neurosci.*, 25(38):8807-8814 (2005)), prevent brain damage after transient middle cerebral artery occlusion in rats (Choi, Y. B., et al, *Brain Res.*, 1019:47-54 (2003)), protect cardiac myocytes from ischemia/reperfusion-induced apoptosis and limit infarction size via mitochondrial K(ATP) channel activation in isolated rat hearts (Townsend, P. A., et al., *FASEB J.*, 18:1621-1623 (2004); Song, D. K., et al, *J. Korean Med. Sci.*, 25(3):380-386 (2010)). Furthermore, it has been demonstrated to prevent apoptosis in isolated islets (Hara, Y., et al., *J. Hepatobiliary Pancreat. Surg.*, 14:493-497 (2007)), prevent autoimmune diabetes induced by multiple low doses of streptozotocin in mice (Song, E. K, et al, *Arch. Pharm. Res.*, 26:559-563 (2003)), reduce autoimmune symptoms in a murine model of human Sjogren's syndrome (Hsu, S. D., et al., *Autoimmunity*, 40:138-147 (2007)), and prevent cataractogenesis induced by selenite in a rat model (Gupta, S. K., et al., *Ophthalmic Res.*, 34:258-263 (2002)). Interestingly, EGCG also activates AMPK (Huang, C. H., et al., *Mol. Nutr. Food Res.*, 53(9):1156-1165 (2009)).

GSE has also been shown to have cancer prevention activities (US Patent Application Publication Nos. 20040047921 and 20050013880). For example, gallic acid, a major constituent of GSE, reduces progression of prostate cancer to advanced stages in the TRAMP mouse model (Raina, K., et al., *Cancer Res.*, 67:5976-5982 (2007)) and GSE also prevents the carcinogenesis of precancerous human breast epithelial cell MCF10A induced by NNK (Siriwardhana, N, et al., *Breast Cancer Res. Treat.*, 109:427-441 (2008)). In addition, GSE has been shown to reduce arterial pressure and salt-sensitive hypertension in estrogen depleted animal models (see review by Carlson, S., et al., *Gend. Med.*, 5 Suppl. A, S76-90 (2008)). It can also effectively prevent UVB-induced skin damage in a three-dimensional tissue culture model of human epidermis (Tomaino, A., et al., *Toxicol. In Vitro.*, 20:1395-1402 (2006)), prevent Aβ oligomerization and attenuate cognitive deterioration in a mouse model of Alzheimer's disease (Wang, J., et al, *J. Neurosci.*, 28:6388-6392 (2008)), prevent high-fat diet-induced obesity in mice and hamsters (Park, S. H., et al, *Nutr. Res. Pract.*, 2:227-233 (2008); Décordé, K., et al, Mol. Nutr. Food Res., 53:659-666 (2009)), inhibit the accumulation of oxidatively damaged DNA due to aging in the spinal cord and brain in a rat model (Balu, M., et al., *Brain Res. Bull.*, 68:469-473 (2006)), and maintain the integrity of the erythrocyte membrane during aging (Sangeetha, P., et al., *Exp. Gerontol.*, 40:820-828 (2005)).

Figure 11:
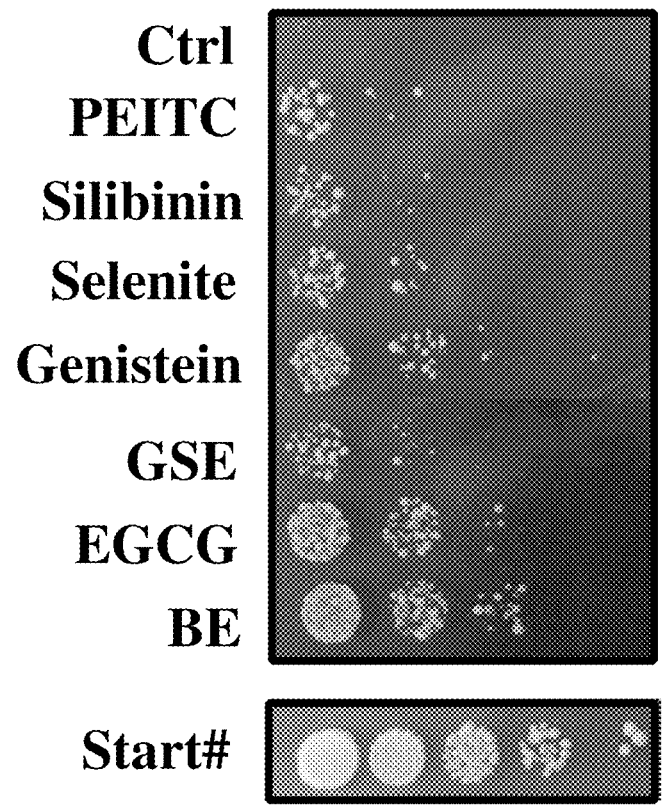
FIG. 11 shows that a number of chemopreventive agents or anti-aging agents inhibited cell death triggered by inactivation of cdc13-1p. The 6.7 μM PEITC, 5 mM silibinin, 1.25 mM selenite, 2.5 mM genistein, 250 μg/mL grape seed extract (GSE), 50 μg/mL EGCG, and 3 mg/mL bilberry extract (BE) were incubated with cells at 37° C. for about 30 hrs. The cell survival was measured by the colony formation assay at a permissive temperature 24° C.

As shown in FIG. 10, both 250 µg/mL GSE and 50 µg/mL EGCG from GTE increased mitochondrial mass in human cells, for example, in lymphoblastoid L40 cells. They also prevented telomere-death in yeast and human primary fibroblasts WI-38 (FIG. 11 and FIG. 7)

FIG. 10 shows that a number of cancer chemopreventive agents increase mitochondrial mass in human lymphoblastoid cells, for example, 10 µM LY294002 (a PI3K inhibitor), 2 µM diallyl trisulfide (DATS), 1 µM benzyl isothiocyanate (BITC), 1 µM phenyl isothiocyanate (PITC), 2 µg/mL resveratrol (RSV) and 0.03 µM lycopene, 6.7 µM phenethyl isothiocyanate (PEITC), 1 µM allyl isothiocyanate, 5 mM silibinin, 1.25 mM selenite ($Na_2SeO_3$), 2.5 mM genistein, and 3 mg/mL bilberry extract. FIGS. 7 and 11 show that a number of cancer chemopreventive agents, including phenethyl isothiocyanate (PEITC), silibinin, selenite ($Na_2SeO_3$), genistein, and bilberry extract, exhibited various degrees of the protective effects on telomere-death in yeast and/or in human cells.

D. A number of Age-Related Diseases or Disorders are Associated with Dysfunction of Mitochondria or/and Telomeres, and Low Doses of Rapamycin Prevent Several Age-Related Diseases or Disorders in Animal Models or Tissue Culture Models.

Cancers. Almost all cancer cells exhibit compromised mitochondrial function. This phenomenon is termed as Warburg effect, which means that as much as 60% of ATP is produced through glycolysis under aerobic conditions in cancer cells, whereas in normal cells, most of the ATP is generated through the mitochondrial oxidative phosphorylation. Oncogenic transformation has been shown to result in suppression of oxidative phosphorylation and an increase in glycolysis, whereas the tumor suppression protein p53 upregulates respiration and suppresses glycolysis. However, it is not clear whether compromised mitochondrial function is the cause or the result of cancers.

It is known that telomere dysfunction is age-dependent due to progressively shortening of telomeres, and maintaining senescence induced by telomere dysfunction is a key mechanism for preventing age-related cancer development. As senescence induced by oncogene activation and mutagens is also via DNA damage response, same as that by telomere dysfunction, senescence maintenance may be an intrinsic mechanism for preventing various cancers.

This invention discloses that mitochondrial function plays a key role in maintaining senescence. Thus, mitochondrial function is important in cancer prevention via maintaining senescence and compromised mitochondrial function is an early step in promoting senescence deterioration and cancer development. Therefore, the telomere dysfunction model can be used to identify candidates for stimulating mitochondrial function, prolonging senescence and preventing cancers. Indeed, a number of known cancer chemoprevention agents were shown to prolong senescence and increase mitochondrial mass (FIGS. 7, 10 and 11). Furthermore, the low dose of rapamycin and AICAR, which prolonged senescence as shown in FIG. 7, reversed the decrease in mitochondrial mass and prevented tumorigenesis induced by mutagen TPA (12-O-tetradecanoylphorbol 13-acetate) (FIG. 12 and FIG. 13) in NIH3T3 cells (see Example 15).

Neuron Degenerative Diseases. In spite of extensive studies, the mechanisms of neuron degenerative diseases are not clear. Mitochondrial dysfunction may play a role in the diseases, since Pakin (linked to Parkinson's disease), Huntintin (linked to Huntington's disease and amyloid-β(causes senile plaques in Alzheimer's disease) are involved in mitochondrial function. Recent studies also suggest that autophagy (protein degradation) plays a role in these diseases.

Figure 15A:
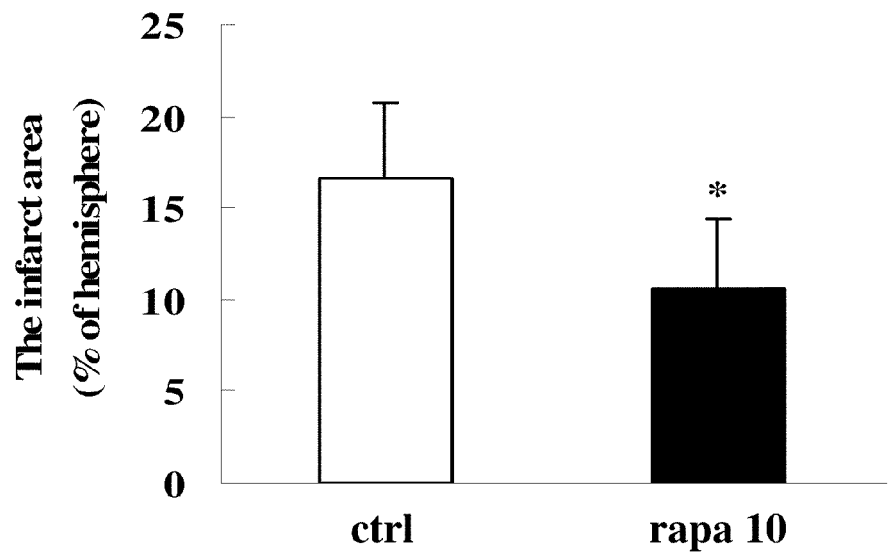
FIG. 15 shows that the low doses of rapamycin reduce the brain infarction volume in a rat model of stroke. (A) Rapamycin (10 μg/kg) reduced the brain damage. Middle cerebral artery (MCA) occlusion model of ischemic stroke was used. SHR-SP rats were randomly divided into two groups (n=8 in each group): a matched control DMSO group and rapamycin group. Rapamycin and the control DMSO were administrated 10 minutes after MCA occlusion. Brain samples were harvested 24 h after MCA occlusion. The coronal sections (2 mm in thickness) were immediately stained with 2% 2,3,5-triphenyltetrazolium chloride (TTC). The infarction region containing dead cells can not be stained as pale, while the normal region with living cells as red. The infarction area and hemisphere areas of each section (both sides) were traced and quantified by an image analysis system (Microsystems Type DM LB2, Leica, Germany). The possible interference of a brain edema in assessing the infarction volume was corrected for with a standard method of subtracting the volume of the nonischemic ipsilateral hemisphere from the contralateral hemisphere volume. The infarction area was expressed as a percentage of the contralateral hemisphere. (B) The low doses of rapamycin prevent brain damages induced by ischemic infarction. Rapamycin at 0, 0.3, 1, 3 and 10 μg/kg was administrated to SHR-SP rats (n=8 in each group) for 20 days prior to MCA occlusion.
Figure 15B:
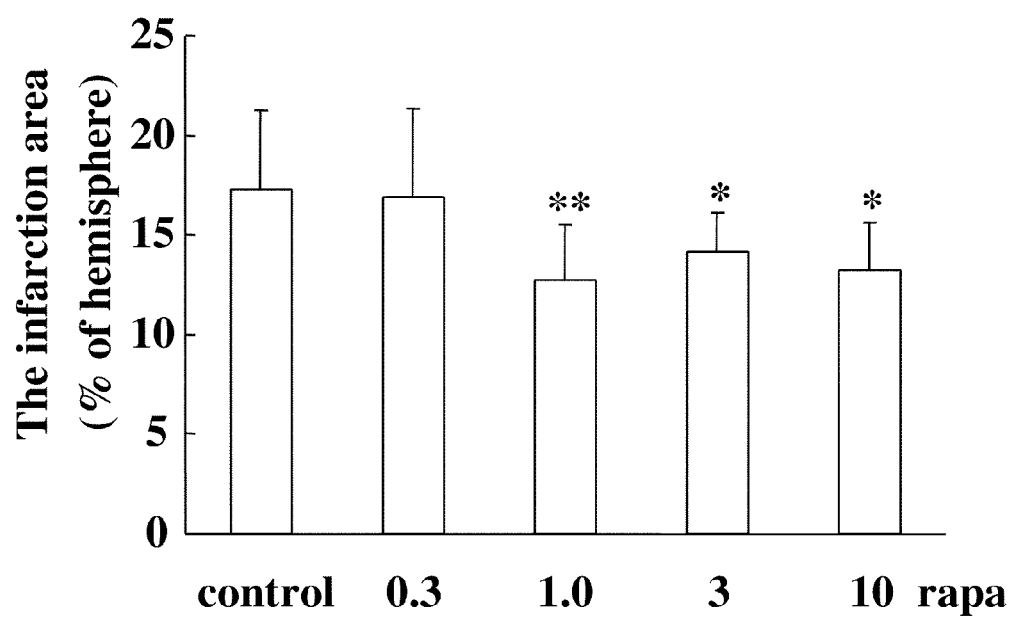
Figure 16:
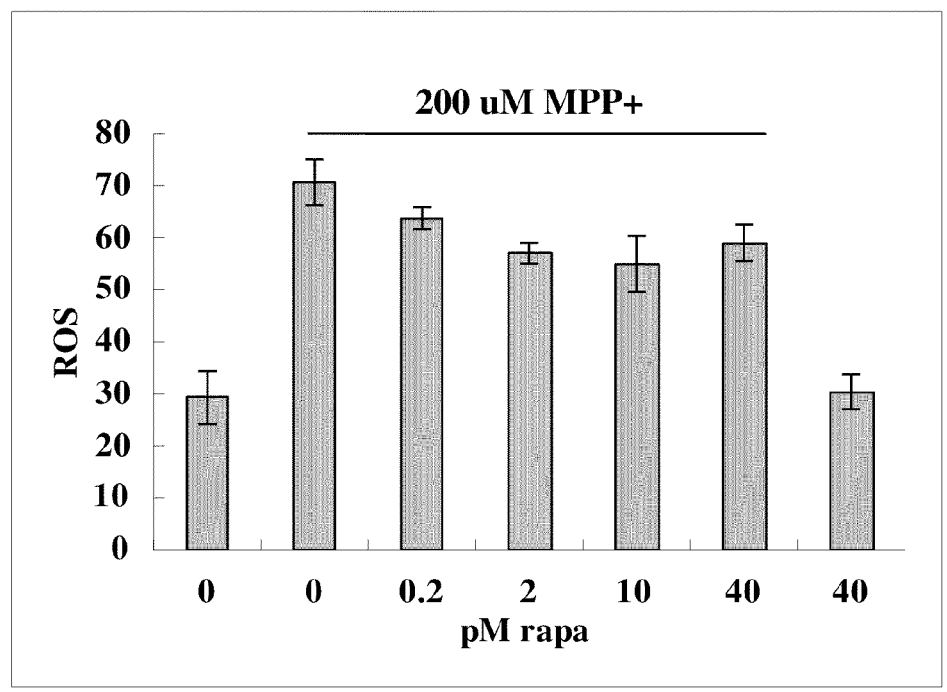
FIG. 16 shows that low doses of rapamycin decrease ROS levels induced by $MPP^+$ in human primary fibroblast WI-38 cells (200 μM $MPP^+$ was used). MPP+ with various concentrations of rapamycin was incubated with WI-38 cells for 3 days. Cells were stained with dehydrorhodamine 123 in the dark for 30 min prior to FACS analysis.

This invention discloses that the low doses of rapamycin, but not higher doses of rapamycin, reduce ROS levels, increase the life span of rat cerebellar granule neuron (CGN) cells in culture (FIG. 14A and FIG. 14B) and prevent brain damage due to cerebellar infarction in a rat stroke model (FIG. 15A and FIG. 15B) (see Examples 16-18). Rapamycin at low doses also reduces ROS levels induced by 200 μM MPP$^+$, the dorpaneuric toxin used to induce Parkinson's in marine models (FIG. 16). Furthermore, EGCG, which has been reported to prevent or treat neuron degenerative diseases, can also prolong senescence (FIG. 7 and FIG. 11). Thus, the low doses of rapamycin and EGCG can prolong the life span of both post-mitotic and senescent cells, suggesting that maintenance of the G0 phased post-mitotic neuron cells share similar mechanisms to those of the G0 phased senescent cells. Therefore, in one aspect, the present invention is based on the discovery that the senescent model can be used to identify and detect drug candidates that prevent neuron degenerative diseases or disorders, including but not limited to stroke, Parkinson's, Alzheimer's, and Huntington's diseases.

Heart Failure, Atherosclerosis and Myocardial Infarction. Telomere dysfunction has been shown to play an important role in chronic heart failure. It has been shown that in cultured cardiomyocytes, interference with TRF2 function triggered telomere erosion and apoptosis. Conversely, exogenous TRF2 conferred protection from oxidative stress, indicating that cell death can occur via telomere dysfunction even in post-mitotic, noncycling cells (Oh, H., et al., *Proc. Natl. Acad. Sci. USA,* 100:5378-5383 (2003)). In vivo, the aged 5th-generation TERC-deficient mice (G5TERC-KO) (a telomerase mutant model due to deficiency in telomerase RNA encoded by TERC gene) exhibited significantly shorter telomeres in cardiomyocytes, ventricular dilation, thinning of the myocardium, cardiac dysfunction, and sudden death. Heart sections from the G5TERC-KO mice revealed an increased expression of DNA damage response protein p53 and increased apoptosis, as well as a 50% reduction in the number of left ventricular myocytes as compared with wild-type mice (Leri, A., et al., *EMBO J.,* 22:131-139 (2003)).

Atherosclerosis is commonly referred to as a hardening or furring of the arteries. It is caused by the formation of multiple plaques within the artery. The dysfunction of vascular endothelial cells (ECs) triggered by atherogenic stimuli is of central importance in the pathogenesis of atherosclerosis. Accelerated telomere erosion and premature senescence have been observed in human atherosclerotic lesions (Ogami, M., et al., *Arterioscler. Thromb. Vasc. Biol.,* 24:546-550 (2004); Minamino, T., et al., *Circulation,* 105:1541-1544 (2002)), suggesting that dysfunction or loss of EC due to age-dependent telomere erosion may be an early step of plaque formation.

Coronary atherosclerosis leads to the blockage of coronary circulation that causes myocardial infarction (MI, commonly known as heart attack). MI leads to the loss of the post-mitotic cardiomyocytes, maladaptive remodeling, cardiac contractile dysfunction and eventually congestive heart failure.

Figure 17:
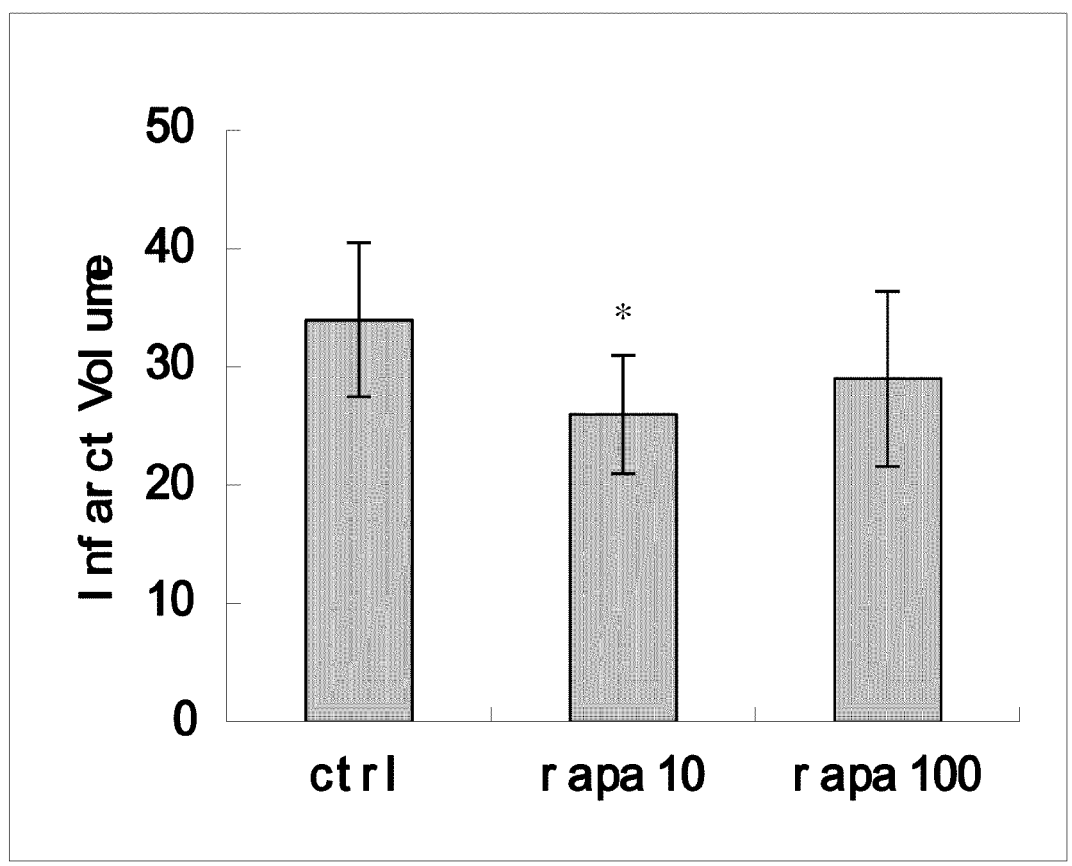
FIG. 17 shows that the low dose of rapamycin at 10 μg/kg, but not at 100 μg/kg, reduces the myocardial infarction (MI) volume in a rat model. Male Sprague-Dawley (SD) rats of 200 to 250 g were used (n=10-12 for each group). Rapamycin at doses of 0, 10, and 100 μg/kg/day was administrated for 3 days prior to the MI experiment. Under ether anesthesia, the heart was exteriorized, and the left anterior descending arteries were ligatured between the pulmonary outflow tract and the left atrium. Then the beating heart was quickly returned to its normal position, the thorax was closed, and the air was removed. The rats were returned to the cages. Five hours after the coronary artery ligature, the rats were sacrificed. The left ventricle was isolated and cut into 4 to 5 slices perpendicular to the cardiac long axis. The slices were stained in nitro blue tetrazolium phosphate buffer. The normal tissue was stained in blue, while necrotic tissue remained unstained. The stained and unstained tissues were isolated and weighed separately. The MI size was expressed as a fraction of the total left ventricular weight.

This invention discloses that the low dose of rapamycin at 10 μg/kg, but not at 100 μg/kg, significantly reduced the myocardial ischemic infarction in a rat model (FIG. 17 and Example 19). Furthermore, it has been reported that AMPK activator metformin also can reduce myocardial infarction in marine models and protect myocardial cells from mitochondria-mediated cell death (Calvert, J. W., *Diabetes,* 57:696-705 (2008)). These results demonstrate the importance of the TOR/AMPK/mitochondria pathway in maintaining the post-mitotic myocardial cells, similar to that in senescent cells. Thus, the senescence model induced by telomere dysfunction can be used to select drug candidates for myocardial infarction prevention or treatment.

Age-related Macular Degeneration. Age-related macular degeneration (AMD) is a major cause of blindness in the elderly (>50 years). It is initiated from degeneration of retinal pigment epithelial (RPE) cells and results in a loss of vision in the center of the visual field (the macula). It has been reported that telomere erosion, mitochondrial function loss and cell loss are associated with this disease (Matsunaga, H., *Invest. Ophthalmol. Vis. Sci.,* 40:197-202 (1999); Liang, F. Q., et al., *Exp. Eye Res.,* 76:397-403 (2003)). Therefore, improving mitochondrial function to prevent cell loss induced by telomere erosion can prevent or stabilize the early stages of disease. Interestingly, a low dose of rapamycin at 50 pM has been patented for treating this disease (U.S. Pat. No. 7,083,802). Thus, the senescence model induced by telomere dysfunction can be used to select drug candidates for preventing or treating AMD.

Osteoarthritis. Osteoarthritis (OA), a progressive loss of articular cartilage, is the most common chronic joint disease in the elderly population, which causes significant pain and disability. The function of the chondrocytes is essential to the maintenance of a proper cartilage matrix. It has been shown that telomere dysfunction, mitochondrial mutations and apoptotic cell death in chondrocytes are associated with OA (Martin, J. A., et al., *J. Bone Joint Surg. Am.,* 85-A Suppl. 2:106-110 (2003); Ruiz-Romero, C., et al., *Mol. Cell Proteomics.,* 8:172-189 (2009); Dave, M., et al., *Arthritis Rheum.,* 58:2786-2797 (2008)), suggesting that the telomere dysfunction-induced cell loss in chondrocytes is an underlying mechanism for the disease initiation. Therefore, improving mitochondrial function to prevent cell loss induced by telomere dysfunction may prevent or stabilize the early stages of the disease. Thus, the senescence model induced by telomere dysfunction can be used to select drug candidates for preventing or treating OA.

Idiopathic Pulmonary Fibrosis. Idiopathic pulmonary fibrosis (IPF) is a chronic, progressive interstitial lung disease, characterized as an abnormal and excessive deposition of fibrotic tissue in the pulmonary interstitium. It usually occurs in patients of greater than 50 years of age. Recently, it has been shown that mutations in telomerase can lead to adult-onset pulmonary fibrosis (Tsakiri, K. D., et al., *Proc. Natl. Acad. Sci. USA,* 104:7552-7557 (2007)) and short telomeres are associated with IPF (Alder, J. K., et al., *Proc. Natl. Acad. Sci. USA,* 105:13051-13056 (2008); Armanios, M. Y., et al., *N. Engl. J. Med.,* 356:1317-1326 (2007)). The involvement of mitochondria and apoptosis in lung epithelial cells has also been demonstrated in IPF (Kuwano, P., *Intern. Med.,* 47:345-353 (2008)). These results suggest that telomere dysfunction-induced loss of lung epithelial cells may be an initial trigger of the age-related IPF. Therefore, improving mitochondrial function for preventing cell loss induced by telomere erosion in lung epithelial cells may prevent or stabilize the early stages of disease. Thus, the senescence model induced by telomere dysfunction can be used to select drug candidates for preventing or treating AMD.

Skin Aging. Fibroblast aging plays an important role in signs of skin aging such as wrinkles. Progressive shortening of telomeres and accumulation of DNA damages by ROS or UV lead to fibroblast aging, including fibroblast senescence and subsequent cell loss. Fibroblast aging then results in functional loss, including loss of proliferative potential (Mine, S., et al., *PLoS ONE*, 3(12):e4066 (2008); Hayflick, L., *J. Invest. Dermatol.*, 73:8-14 (1979)), changes in cell morphology and metabolism, decline in the production of extracellular matrix proteins such as type I and III collagens (Varani, J., et al., *Am. J. Pathol.*, 168:1861-1868 (2006)), and overexpression of proteases involved in the degradation of the extracellular matrix (West, M. D., et al., *Exp. Cell Res.*, 184: 138-147 (1989)). These changes in vitro may all more or less participate in the in vivo age-related changes of the skin. Maintaining functional mitochondrial population not only slows telomere shortening (FIG. 9B), but also prevents loss of the senescent fibroblasts that are still functional (FIG. 7 and FIG. 9A), and consequently, delays skin aging and prevents skin cancers.

Rheumatoid arthritis (RA). Dysfunctional telomeres and mitochondrial mutations are potential pathogenic factor in RA. It has been shown that hematopoietic precursor cells (HPCs) and bone marrow mesenchymal stem cells (MSCs) from RA patients display premature telomere shortening and reduced replication potential (Colmegna, I., et al., *Arthritis Rheum.*, 58:990-1000 (2008); Kastrinaki, M. C., et al., *Ann. Rheum. Dis.*, 67:741-749 (2008)). Furthermore, HLA-DRB1*04 alleles, the major susceptible genes for this disease, has been shown to regulate the process of telomere shortening (Schonland, S. O., et al., *Proc. Natl. Acad. Sci. USA*, 100:13471-13476 (2003)). Several studies have also shown that some characteristic changes in the composition and structure of the inflamed synovial membrane in RA are linked to an altered apoptotic response of synovial cells (Korb, A., et al., *Apoptosis*, 14:447-454 (2009)). Furthermore, mutations of mtDNA of synoviocyte from RA are greatly increased as compared to controls (Da Sylva, T. R., et al., *Arthritis Res. Ther.*, 7:R844-851 (2005)). Thus, drug candidates that improve mitochondrial function and prevent cell death induced by telomere shortening may be developed to treat this disease.

Diabetes Mellitus. Diabetes mellitus refers to a group of diseases that lead to high blood glucose levels due to a diminished production of insulin (in type 1) or resistance to its effects (in type 2 and gestational). Premature loss of β-cell function due to telomere dysfunction or mitochondrial dysfunction may be an initial step in diabetes mellitus. It is well accepted that mtDNA defects are a common factor in the etiology of diabetes, and mtDNA rearrangement (Ballinger, S. W., et al., *Nat. Genet.*, 7:458-459 (2004); Ballinger, S. W., et al., *Nat. Genet.*, 1:11-15 (1992)) and tRNA mutations (van den Ouweland, J. M., et al., *Diabetes*, 43:746-751 (1994)) are linked to diabetes. Furthermore, inactivation of the mitochondrial transcription factor TFAM, one of the key proteins in mitochondrial biogenesis, in the pancreatic β-cells in mice, leads to progressive decline in β-cell mass by apoptosis, resulting in a severe reduction in serum insulin and increased blood glucose in both fasting and nonfasting states (Koster, J. C., et al., *Cell*, 100:645-654 (2000); Wallace, D. C., *Am. J. Med. Genet.*, 106:71-93 (2001)). It has also been shown that β-cell in human pancreatic islet undergoes telomere erosion and telomere-induced senescence in vitro (Halvorsen, T. L., *J. Endocrinol.*, 166:103-109 (2000)). Therefore, drug candidates that improve mitochondrial function and prevent cell loss induced by telomere erosion may prevent the disease.

The age-related diseases mentioned above are a few examples that are associated with mitochondrial deterioration and/or telomere dysfunction. There are many other diseases that would fall into this category, including, but not limited to, obesity, osteoporosis, hypertension, sarcopenia, cataract, multiple sclerosis, Sjogren syndrome, age-related hearing loss, graying, age-related immune dysregulation, and disorders caused by the decline in testosterone, estrogen, growth hormone, IGF-I, or energy production. Thus, the present invention also encompasses any age-related diseases or disorders uncovered in the future.

In summary, this invention discloses that mitochondria play a vital role in maintaining the growth-arrested state in senescent and post-mitotic cells such as neurons and cardiamyocytes and are associated with a number of age-related diseases. In addition, mitochondria dysfunction and telomere dysfunction have also been linked to age-related diseases. These principles are the basis to use the senescent cells to search for drug candidates against age-related disease.

Figure 18:
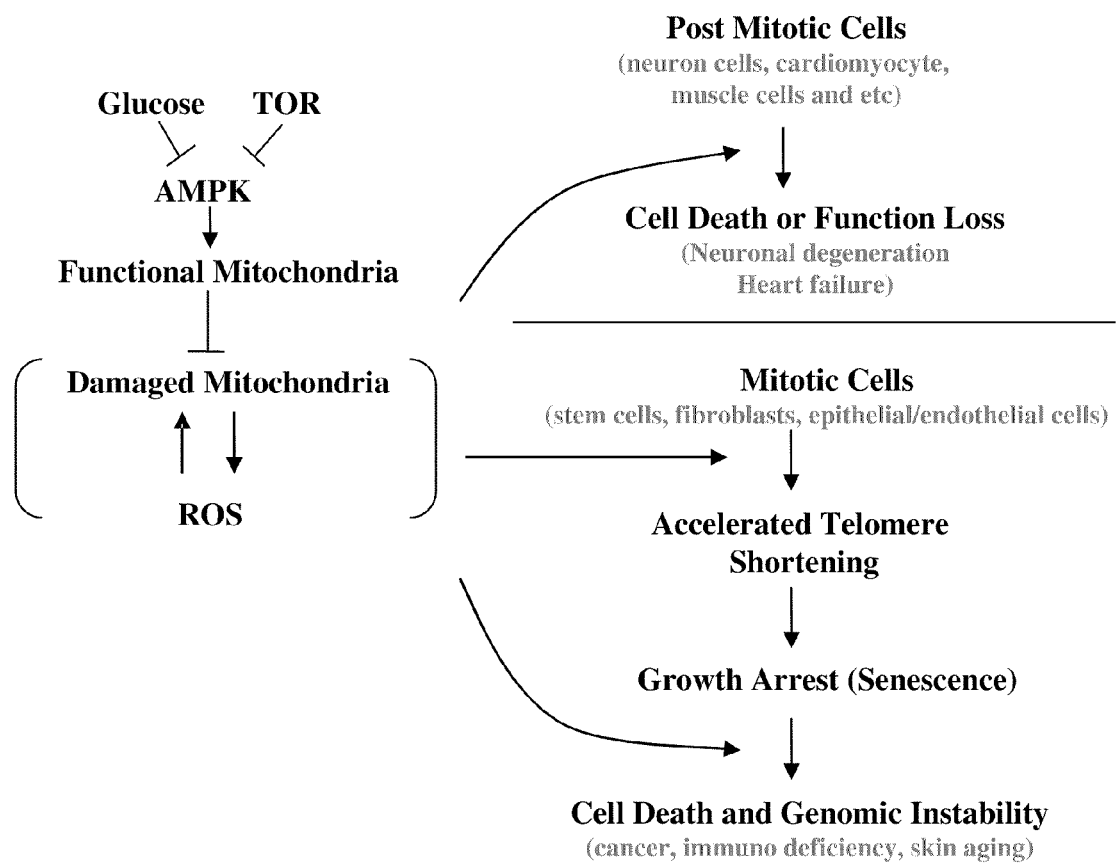
FIG. 18 shows a model of glucose or TOR regulates aging processes through the AMPK/ROS/mitochondria pathway in various tissues, which lead to age-related disorders.

FIG. 18 summarizes the mechanism of age-related diseases and illustrates how inhibition of the nutrient/TOR pathway prevents age-related diseases. In brief, mitochondria play a vital role in age-related diseases in various cells and tissues. In post-mitotic cells such as neuron cells, muscle cells and cardiomyocytes, mitochondria serve to maintain the post-mitotic state, thus prevent cells from re-entering the cell cycle and the subsequent cell death. In proliferative tissues, improving mitochondrial function can result in a reduction of oxidative stress and increase their replication potential. Upon entering senescence, mitochondria also maintain the senescent state and prevent subsequent cell loss, as in post-mitotic cells. Cell loss could trigger repairing cascades, such as inflammation response in RA and fibrosis in IPF disease. Cell loss could also lead to functional loss of the tissues and degenerative diseases, such as bone marrow failure, neuron degeneration and heart failure. In another situation, senescence deterioration could lead to tumorigenesis and cancer progression. Caloric restriction, including glucose restriction, and the low doses of rapamycin stimulate mitochondrial function and prevent various age-related disease or disorders.

In summary, this invention has disclosed, inter alia: (i) that senescent state is maintained by mitochondrial function; (ii) maintenance of the post-mitotic state is similar to that of senescence; (iii) CR through mitochondrial function maintains senescent and post-mitotic cells, and thus senescence models can be used to identify candidates that stimulate mitochondrial function and prevent various age-related disorders; (iv) a number of cancer chemoprevention agents, inhibitors of glucose intake and AMPK activators are able to prolong senescence and thus can be developed into drug candidates for age-related diseases; and (v) a low dose of rapamycin, as a CR mimic, is able to maintain senescent and post mitotic cells and prevent cancer, brain damage in stroke, myocardial ischemic infarction and other age-related diseases or phenotypes.

Very recently, after the provisional applications to which this application claims priority were filed, several researchers reported that the therapeutic doses of rapamycin may also have some effect on aging and age-related diseases via protein translation inhibition and degradation (autophagy) stimulation. For example, a therapeutic dose of rapamycin (7.5 mg/kg) is reported to be effective for Parkinson's disease in a mice model via protein translation inhibition particularly on RTP801/REDD1/Ddit4, a protein that is induced in affected neurons of Parkinson patients and causes neuron death (Malagelada, C., et al., *J. Neurosci.*, 30(3):1166-1175 (2010)). Another report demonstrated that a therapeutic dose of rapamycin (2.24 mg/kg) rescues cognitive deficits and ameliorates Aβ and tau pathology in a mouse model of Alzheimer disease by increasing autophagy (Caccamo, A., et al., *J. Biol. Chem.*, Feb. 23, 2010). Furthermore, a modest effect on life-span extension (~10%) in the mouse and fruit fly was shown to be induced by rapamycin at the therapeutic dose (Harrison, D. E., et al., *Nature*, 460(7253):392-395 (2009)), as compared to the effect on life span extended by CR (~30-40%). Interestingly, such a life span extension by rapamycin in fruit fly is not via the AMPK/mitochondrial pathway, but via protein translation inhibition and/or autophagy stimulation (Bejdov, I., et al., *Cell Metab.*, 11(1):35-46 (2010)).

These results suggest that therapeutic doses of rapamycin could have some modest effect on some age-related diseases and life span extension via protein translation/growth inhibition and autophagy stimulation. However, because of various adverse effects, the therapeutic doses of rapamycin are not suitable for long-term use to prevent age-related diseases or disorders. On the other hand, low doses of rapamycin, as a mimic of CR (in fact, better than CR due to its minimum adverse effect) as disclosed herein, can be used for preventing aging and age-related diseases via the AMPK/mitochondrial pathway, which has various apparent advantages over the use of therapeutic doses of rapamycin discussed above, for example, higher effectiveness and lesser adverse effects.

EXAMPLES

A. The Use of Telomere Dysfunction Model for High-Throughput Screening to Identify and Detect Anti-Aging Candidates for Preventing or Treating Age-Related Diseases or Disorders In one aspect of the present invention, the yeast telomere dysfunction model cdc13-1 is used for the high-throughput screening for discovery of useful anti-aging agents for the prevention or treatment of age-related diseases or disorders. The cdc13-1 model has been well studied and the cell cycle arrest occurs at the G2/M phase immediately after cdc13-1p inactivation, followed by cell death. By using this model, the present invention provides a rapid way to identify candidates that can prevent telomere dysfunction-induced cell death. Other models associated with telomere dysfunction that exhibit this type of quick growth arrest and subsequent cell death can also be used, for example, stn1-1, cdc17-1 and cdc17-2 temperature sensitive mutants in Stn1p (capping telomeres in yeast) and Cdc17p (the yeast catalytic subunit of the DNA polymerase I alpha-primase complex) respectively. In addition, yeast cells that exhibit telomere dysfunction and apoptosis can be used, which include, but are not limited to, mutations in Est1p, Est2p, Est3p, Hdf1p, Hdf2p, or cdc13-2 mutant. WI38 human primary fibroblasts then can be used as the human telomere dysfunction model to confirm or detect drug candidates. The followings (Examples 1-6) use the cdc13-1 model.

Example 1

Figure 19:
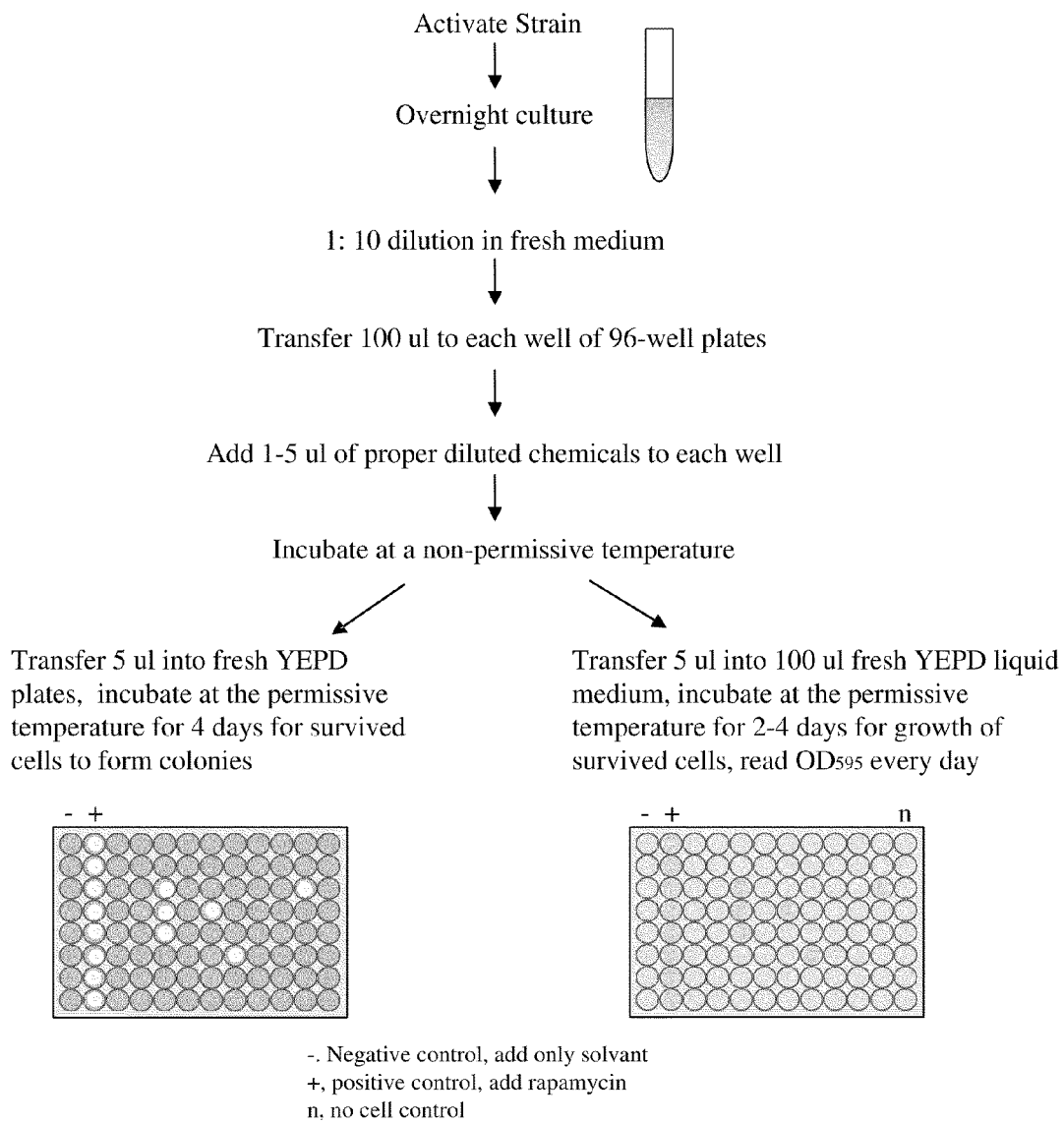
FIG. 19 illustrates a method for high-throughput screening to identify and to detect anti-aging candidates using cell surviving assays in yeast.

Identification of Agents that Prevent Cell Death in cdc13-1 Model Using Cell Surviving Assays (as Shown in FIG. 19)

For high-throughput screening of compounds or compositions that improve mitochondrial function, prolong the cell cycle arrested state and prevent cell death in cdc13-1 model, cdc13-1 cells are activated from −80° C. stock first by streaking them on a fresh YEPD or yeast complete medium (YC) plate and then incubating at the permissive temperature (about 24° C.) for 3 to 5 days until single colonies formed. A few yeast colonies are picked and cultured overnight in the same liquid medium at a permissive temperature 24° C. The overnight cultures are diluted into fresh medium from 1:2 to 1:20 (optimized at about 1:10 for cdc13-1 strain).

Yeast cells are transferred into 96-well plates or any suitable formats of plates. Prospective compounds or compositions, for example, serially diluted drugs, compounds, peptide libraries or other libraries by $H_2O$, DMSO (dimethyl sulfoxide) or other organic solvents, are added into the cells with a volume less than 5% of total volume of the cell mixture. In the mixtures, the corresponding solvent is included as a negative control, and a 1 nM rapamycin solution in the same solvent is included as a positive control. Yeast cells are then incubated at a non-permissive temperature (about 37° C.) for two days, or until no surviving cells in the negative control are detected.

A small volume of cells (e.g., 5 μl) is transferred to YEPD agar plates pre-made in another 96-well or any other format of plates (Cells can also be diluted first before transferring). Plates are incubated at a permissive temperature (about 24° C.) for at least 3 days or until colonies form in positive control. Chemicals that promote colony formation will be considered as primary candidates. Alternatively, a few microliters (μl) of cells are transferred into YEPD liquid medium in another 96-well plate or any suitable format of plates. The plates are incubated at a permissive temperature (about 24° C.), and $OD_{595}$ (optical density at 595 nm) is read periodically, e.g., once a day. Chemicals that increase cell density more than the negative control are considered to be primary candidates. This method is illustrated in FIG. 19.

The primary candidates are confirmed by an apoptotic assay and a ROS assay as described in Examples 2 and 3 respectively. Primary candidates can be further tested to see whether they inhibit cell growth at G1 by monitoring growth curve at a permissive temperature as in FIG. 1D and by measuring DNA content distribution using FACS analysis as in FIG. 2A. To eliminate the possibility that a mutant cell is generated by the candidate and thus forms colonies at the non-permissive temperature, cdc13-1 cells can be incubated with the candidate at about 37° C. for colony formation. In one important aspect, the candidates will be tested for whether they can improve mitochondrial function and inhibit cell loss in senescent mammalian cells such as WI38 fibroblasts. Whether they are effective in preventing a particular age-related disease will then be further investigated in specific disease models. For example, they can be tested for inhibiting tumorigenesis and/or decreasing brain infarction sizes in animal models.

Other types of suitable plates for the high-throughput screen include, but are not limited to, 384-well plates. In addition, this method can be adapted to other types of plates for detecting and confirming the candidates, such as 6-well, 12-well plates and etc.

Example 2

Identification of Agents that Prevent cdc13-1 Cell Death Using an Apoptotic Assay Cell death in cdc13-1 exhibits apoptotic markers. This characteristic can be employed for high-throughput screening since it takes less time than the cell surviving assay mentioned in Example 1. It can also be used for confirming positives identified from the high-throughput screening in Example 1. In addition, this assay can also be used to screen for agents that inhibit apoptosis.

After incubating at a non-permissive temperature (about 37° C.) for a day (about 18-24 hrs), the cdc13-1 cells with compounds are stained with FITC-conjugated z-VAD-FMK (a suicide substrate that only binds to activated caspase), or other suitable apoptotic detecting agents, for 20 min in the dark. Cells may be washed once with Phosphate Buffered Saline (PBS). Plates are read by a fluorescent microplate reader. The negative control (cells in the absence of the compounds or compositions screened) would have a high FITC signal due to cell death. The compounds or compositions that reduce the FITC signals are considered as positives or primary candidates. They are confirmed by assay the surviving cells as in Example 1, and further tested for their ability to reduce ROS and improve mitochondrial function. These activities will also be tested in human telomere dysfunction models such as WI-38 senescent cells. Their activity in preventing cancer and other age-related diseases or disorders are further tested in proper models.

The annexin V binding assay to measure phosphotidylserine flipping has been described in FIG. 3B as an apoptotic marker. It can also be used for high-throughput screening.

Example 3

Figure 20:
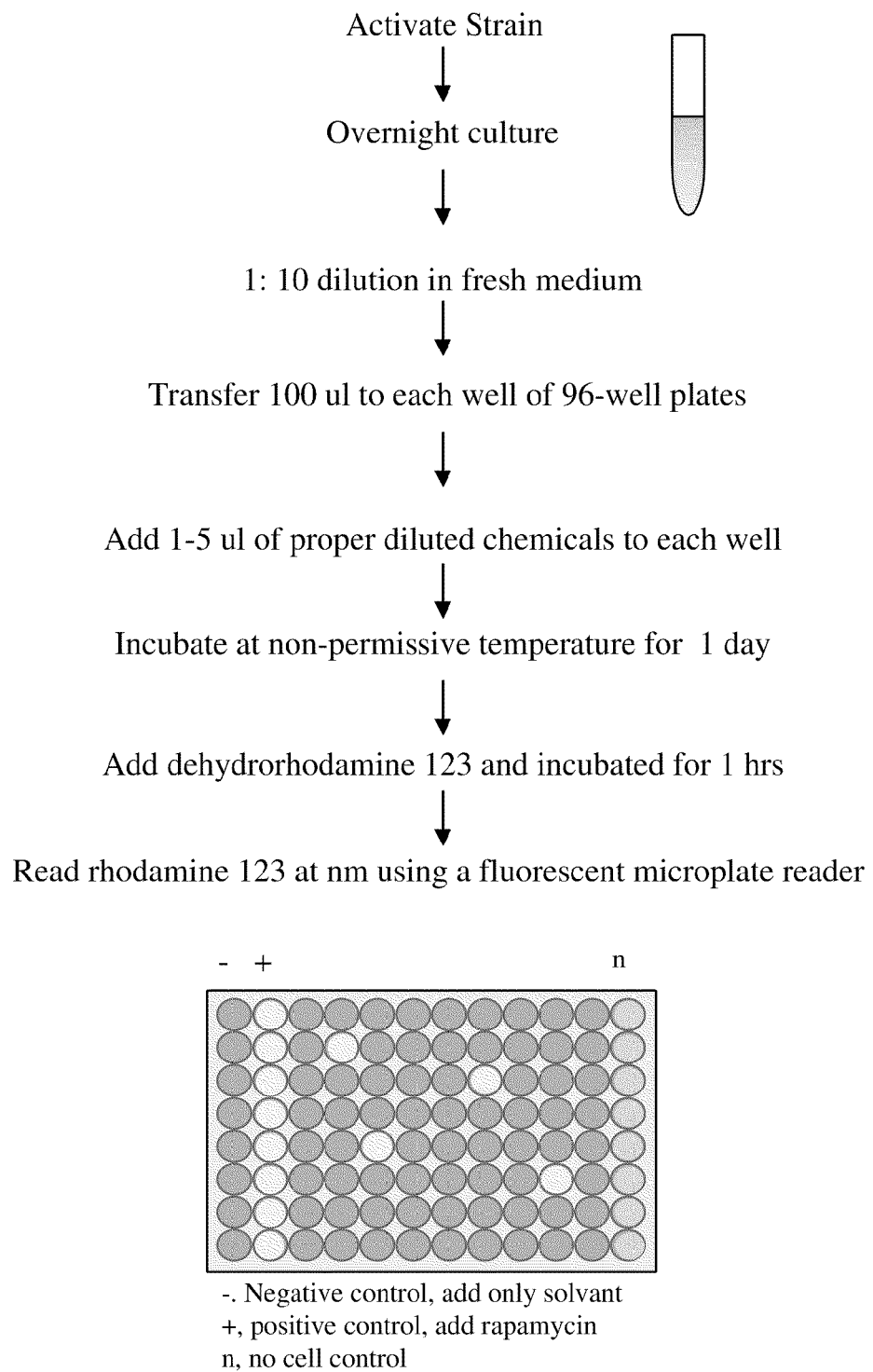
FIG. 20 illustrates a method for high-throughput screening to identify and to detect anti-aging candidates using the ROS assay in yeast.

Identification of Agents that Prevent cdc13-1 Cell Death by Measuring ROS (as Shown in FIG. 20)

Cell death in cdc13-1 exhibits dramatically elevated ROS levels. This characteristic can be used to search molecules that inhibit cdc13-1 cell death. The ROS assay takes less time than the cell surviving assay described in Example 1, and can be used in the high-throughput screening, as well as in confirming the primary candidates identified from high-throughput screening of Examples 1 and 2. In addition, this assay can also be used to screen for antioxidants.

FIG. 20 illustrates the procedure. After incubating at a non-permissive temperature (37° C.) for a day, the treated cells are stained with dehydrorhodamine 123 (or other suitable ROS detection agents) for about one hour in the dark. Plates are read by a fluorescent microplate reader. The negative control (i.e., cells in the absence of the compounds or compositions screened) should have high levels of ROS released during cell death. The compounds or compositions that reduce the ROS are considered to be primary candidates, which are further tested for cell death prevention and mitochondrial function improvement in both yeast and human models. Their activity in preventing cancer, neuron degeneration and other age-related diseases or disorders are then further tested in proper models.

Example 4

Identification of Agents that Prevent Deterioration of Senescent Cells in Telomere Dysfunction Models by Measuring Mitochondrial Mass Cell death in cdc13-1 is accompanied with a dramatic increase in mitochondrial mass ("mito mass"). This characteristic can be used to search for molecules that inhibit cdc13-1 cell death. The mitochondrial mass assay takes less time than the cell surviving assay described in Example 1, and can be used in the high-throughput screening, as well as in confirming positives from high-throughput screen described in Examples 1, 2 and 3.

After incubating at a non-permissive temperature (about 37° C.) for a day, the treated cdc13-1 cells are stained with MitoTracker Green (or any suitable mitochondrial mass staining agents) for 20 min in the dark. Plates are read by a fluorescent microplate reader. Since dead cells contain more deteriorated mitochondria which have lost membrane potential, they would show dramatic increases in mitochondria mass staining. The compounds or compositions that improve mitochondrial function and prevent cell death would reduce mitochondrial deterioration, decrease mitochondrial mass signals, and thus are considered as positives. The positives will be further tested for their ability to prolong senescence in yeast and human models.

Example 5

Identification of Biological Molecules from DNA and Nucleic Acid Libraries that Prevent Death of Senescent Cells A Li-PEG transfection method is described as an example. However, other transfection methods can also be used. Fresh yeast cells (cdc13-1) in log phase are washed by distilled $H_2O$ extensively. Cells are then incubated with a transfection buffer (2 mM tris pH7.5, 100 mM LiAC, 0.5 mM $MgAC_2$, 0.1 mM $CaAC_2$, 15% glycerol, 40% PEG-4000, 24 ug/mL ss DNA) and a DNA library at 24° C. for 1-4 hours. The mixtures are heat-shocked at about 42° C. for 15 min. Three volumes of rich medium YEPD are then added to the mixture and incubated for an hour at a room temperature (about 24° C.). After centrifugation to remove liquid, cells are re-suspended in distilled $H_2O$ and plated on the selecting medium plates for the particular library. After incubation at the permissive temperature 24° C. for at least 4 days, transformants are harvested and cultured in a liquid selecting medium at a permissive temperature (about 24° C.). Cells in log phase are shifted to a non-permissive temperature (about 37° C.) and incubated for 2 days to allow cell death induced by inactivation of cdc13-1p. The cells are then properly diluted, plated on the YEPD medium and incubated at about 24° C. for more than 4 days, or until surviving cells form colonies. The colonies are picked, and DNA is individually isolated from each colony, amplified by PCR (DNA polymerase chain reaction) and sequenced to identify the DNA sequence. The DNA that can prevent cell death induced by inactivation of cdc13-1p is then confirmed by the introduction of the purified DNA into cdc13-1 cells again. The positives are then tested for prevention of deterioration of senescent human fibroblasts and regulation of mitochondrial function and oxidative stress.

Example 6

Identification of Proteins that can Promote Cell Death from Disruption or Gene Deletion Libraries To screen or identify proteins whose function is to promote telomere dysfunction-induced cell death, the gene disruption libraries, e.g., yeast transposon insertion libraries can be introduced into cdc13-1 strain. Alternatively, cdc13-1 can be introduced into yeast deletion strain libraries, in which each strain has a specific gene deletion. A protein whose deletion or disruption can prevent cell death induced by inactivation of cdc13-1p is considered to be a candidate.

Example 7

Identification of Agents that Stimulate Mitochondrial Biogenesis in Mammalian Cells This experiment can be performed in human cells directly. Cell lines are chosen according to a particular age-related disease or disorder studied. Cells in 96-well plates are treated for about a day and fixed by ethanol (final about 60%) to eliminate the effect of mitochondrial membrane potential, and stained with a MitoTracker dye (Invitrogen). The fluorescent signals are read in a fluorescent plate reader. Greater than 20% increase in mitochondria fluorescent signal as compared to non-treatment cells are considered as positives which are further tested for their effects on preventing cell loss induced by telomere dysfunction in cdc13-1 and WI-38 models, and then on mitochondrial membrane potential and ROS levels.

An alternative method to screen for candidates that stimulate mitochondrial biogenesis is using real-time-quantitative-reverse-transcription polymerase chain reaction (often donated as qRT-PCR) to test whether the mRNAs of transcription factors for mitochondrial biogenesis are up-regulated. The transcription factors for mitochondrial biogenesis comprise TFAM, NRF-1, NRF-2, PGC-1α, PGC-1β, TFB1M, TFB2M, ERRs (ERRα, ERRβ, ERRγ), PRC, POL-RMT, PPAPs (PPAPα, PPAPγ, PPAPδ), and RIP140. Here TFAM is used as an example and primary human cells are used preferably. WI-38 cells seeded in 96-well plates (or other plate formats) are incubated with a compound library for a desired period (e.g., about 18 hrs). Cells are washed with PBS and lysed in plates by the TaqMan Gene Expression Cells-to-CT Kit from Applied Biosystems, which removes DNA and makes cell lysates ready for RT-PCR. Cell lysates are diluted in a new set of 96-well plates with reagents from the Qiagene's one-step qRT-PCR kits and QuantiFast Multiplex RT-PCR Kits. Primer sets ACAGCTAACTCCAAGTCA-GATTATGTC-3' and 5'-GTAGACACTTGAGACTAA-CAACCGT-3' for TFAM, and 5'CAAAGACCTGTACGC-CAACACAGT3' and 5'-TTGCTGATCCACATCTGCTGGAAG-3' for β-Actin (control), that have been successfully used to detect TFAM mRNA increase by 50 pM rapamycin and other agents (data not shown, and as described in Fu X, et al, PLoS ONE, 3(4): e2009, 2008), can also be used. The compounds or compositions that increase TFAM mRNA greater than about 2-fold would be considers as positives, which are further tested for senescence maintenance in the cdc13-1 or WI-38 telomere dysfunction model.

Example 8

Testing of the Activity of a Compound or Composition in Preventing Senescence Loss in WI-38 Fibroblasts There are situations in which a compound or composition such as a known drug, a nature extract or a nature product, a known peptide, or a candidate obtained from a library screening in a yeast model, needs to be tested for whether it has an anti-aging effect in human cells. The desired testing can be done as described in FIG. 7 using WI-38 fibroblasts.

Example 9

Determination of the Anti-Aging-Biological Concentrations of Rapamycin and its Derivatives Using cdc13-1 Yeast Cells There are situations that the amount or concentration of anti-aging-biologically active rapamycin needs to be determined, for example, in different batches of purified rapamycin, samples during the purification process, crude extracts, blood plasma after administration of rapamycin, or in a chemically modified rapamycin derivative, etc. To determine the anti-aging-biologically active rapamycin from various sources, the rapamycin containing materials are first diluted in a proper solvent with the desired serial dilutions (e.g., 3-fold or 10-fold serial dilutions). About 5% (in volume, or less) of such diluted materials are then added to freshly 10-fold diluted cdc13-1 cells in YEPD medium. After about 24 to 36 hrs incubation at the non-permissive temperature (about 37° C.) to induce cell death, the number of surviving cells is measured by the colony formation assay as described in FIG. 1. To make a standard concentrations of active rapamycin, purified rapamycin is diluted with DMSO to 1 μM. Fresh cdc13-1 overnight culture is 10-fold diluted in the YEPD medium. The 1 μM rapamycin is serially diluted 3-fold or 2-fold with the cell-containing medium to about 10 pM. The mixture is then incubated at about 37° C. for about 24-36 hrs for cell death induced by inactivated cdc13-1p. The numbers of surviving cells in the presence of various concentrations of standard rapamycin solutions are determined by colony formation and the numbers are plotted against the concentrations to obtain a standard curve. The numbers of surviving cells in the presence of various rapamycin sources are then compared to the standard curve, and the concentration of active rapamycin thus is determined. For a rapamycin derivative, the standard curve would be first created for the same derivative. In addition to colony formation, apoptotic assays and ROS release by cdc13-1 cell death can also be used to determine the anti-aging-biological concentrations of rapamycin.

This method can also be used to determine the anti-aging-biological concentrations of other anti-aging compounds or compositions, for example, EGCG. In addition, this method can be used as an assay to detect the anti-aging activity of a biological sample.

Example 10

Figure 21:
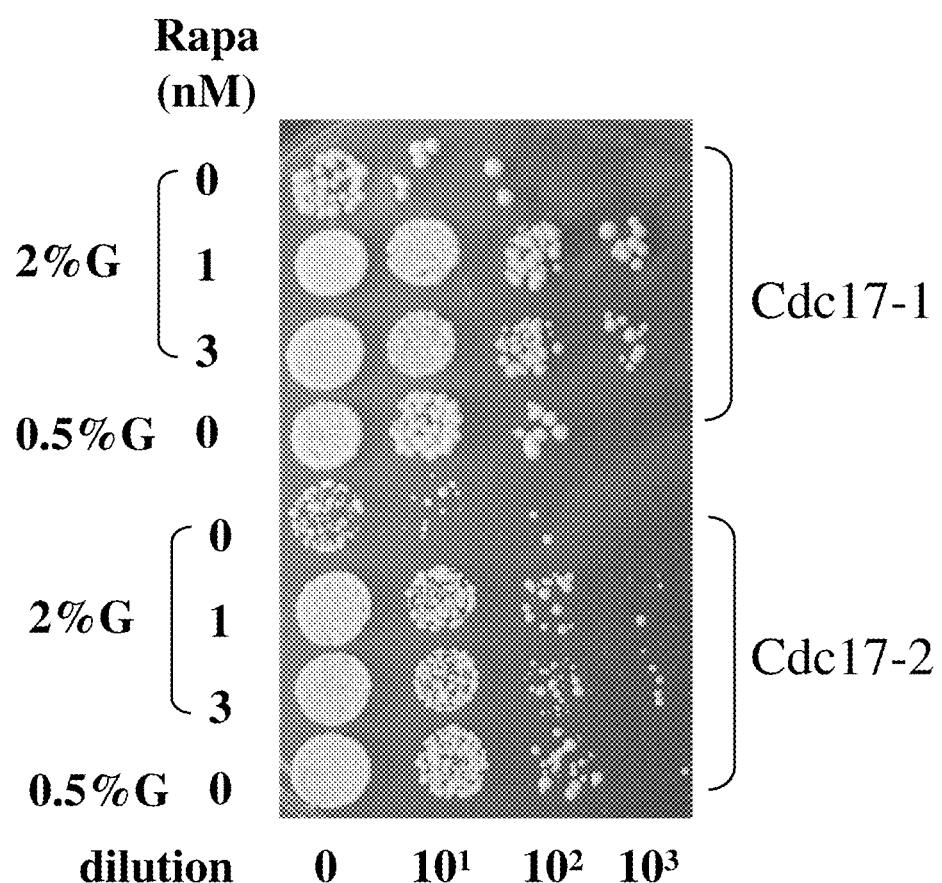
FIG. 21 shows examples of detection of an anti-aging agent using the yeast mutant cdc17-1, or cdc17-2. The mutant cells were diluted into a fresh YEPD medium containing rapamycin of 0, 1 and 3 nM, or 0.5% glucose YEPD medium and incubated at about 37° C. for 22 hrs. Cells were then serially diluted 10-fold and spotted on a YEPD plate. The plate was incubated at a permissive temperature 24° C. for colony forming from surviving cells.

Detection of an Anti-Aging Agent Using the cdc17-1 and cdc17-2 Yeast Mutant Rapamycin (1 and 3 nM) and reduced glucose are used as examples of anti-aging agents. The cdc17-1 and cdc17-2 yeast cells was activated from −80° C. stock first by streaking them on a fresh YEPD plate and then incubating at a permissive temperature (about 24° C.) for 5 days until single colonies formed. A few yeast colonies were picked and cultured overnight in the YEPD liquid medium at a permissive temperature about 24° C. The overnight cultures were diluted (10-fold dilution) into fresh YEPD medium containing rapamycin of 0, 1 and 3 nM, or 0.5% glucose YEPD. The mixtures were then incubated at a non-permissive temperature (about 37° C.) for 22 hrs to induce cell death following the growth arrest triggered by to inactivate the DNA polymerase-alpha. The number of surviving cells was measured by the colony formation assay. In brief, the mixtures were then serially diluted (10-fold), and a small amount of cells (5 μl) was spotted on a YEPD plate. The plate was incubated at the permissive temperature (about 24° C.) for at least 4 days to allow colonies forming from surviving cells. As shown in FIG. 21A, rapamycin prevented cell induced by inactivation of DNA polymerase-alpha in cdc17-1 and cdc17-2 mutant yeast.

Example 11

Detection of an Anti-Aging Agent Using the est1$^{-ts}$ Yeast Mutant

Rapamycin is used as an example of anti-aging agents in this model. Rapamycin can prevent ROS induction and apoptotic-like cell death induced by inactivation of telomerase in the est1$^{-ts}$ yeast cells (est1$^{-ts}$ rad52::URA3) as described in my previous paper (Qi, H., et al., *PlosOne*, 2008). The assay was done by growing cells on the rapamycin-containing plates. This assay can be modified by growing cell in the liquid medium to facilitate adoption of high throughput screen. In brief, est/$^{-ts}$ cells are activated from the −80° C. stock first by streaking them on a fresh YEPD plate and then incubating at a permissive temperature (about 24° C.) for 5 days until single colonies formed. A few yeast colonies are picked and cultured overnight in the YEPD liquid medium at a permissive temperature about 24° C. The overnight cultures are diluted about 100- to 300-fold into fresh YEPD medium containing 0, or 1 nM of rapamycin. The mixtures are incubated at the non-permissive temperature about 37° C. for about two days. Cells are diluted about 100-300-fold again into fresh YEPD medium containing 1 nM rapamycin or the control solvent and then incubated at the non-permissive temperature about 37° C. for about two days. The inactivation of telomerase at the nonpermissive temperature results in progressively shortening of telomeres and eventually telomere dysfunction, which lead to ROS induction and apoptosis-like cell death. Cell death can be measured using an apoptotic assay or a ROS assay. The ROS induction is measured by incubating the cells with a dehydrorhodamine 123 solution (about 5 μg/mL in a PBS buffer) in dark followed by FACS analysis. Cell death is measured by caspase activity as in Example 2.

B. Targeting the Nutrient/TOR/AMPK/Mitochondria/Senescence Pathway for Preventing and Treating Age-Related Diseases or Disorders

Example 12

Measuring the Components of the Senescence Pathway in a Mammalian Model System This example used Western blotting to determine the increases of key proteins in the senescence pathway in mammalian cells induced by an anti-aging agent. Rapamycin was used as an example. WI-38 cells on the 20th day after the last split (senescence) were treated with rapamycin of indicated doses for 18 hrs. Cell lysates were then analyzed by Western blotting. The key proteins in the senescence pathway, p53, p21 and pRB, were increase by the low doses of rapamycin (50 and 100 pM), but not by the higher dose 2000 pM (FIG. 9C).

Example 13

Agents that Exhibit Activities Against Age-Related Diseases or in Cancer Chemoprevention Stimulate Mitochondrial Function and Prolong Senescence Experiments were done as described in FIGS. 7, 10 and 11. As shown in FIG. 10, 50 pM rapamycin, 250 μM AICAR, 20 μg/ml EGCG, 1.6 μg/ml GSE, reduced glucose (from 0.4% to 0.2%), 20 μg/ml bilberry extract (BE), 1 μM AITC, and 12.5 μM 2-deoxyglucose increased mitochondria mass, an indicator of increased mitochondrial biogenesis, also prevented cell loss in senescent WI-38 fibroblasts (FIG. 7). Furthermore, phenethyl isothiocyanate (PEITC), silibinin, selenite ($Na_2SeO_3$), and genistein that increased mitochondrial mass, also exhibited various degrees of the protective effects on telomere-death in yeast cells (FIG. 10 and FIG. 11).

Example 14

AMPK Activator Inhibits TPA-Induced Transformation of NIH3T3 Cells

Figure 12:
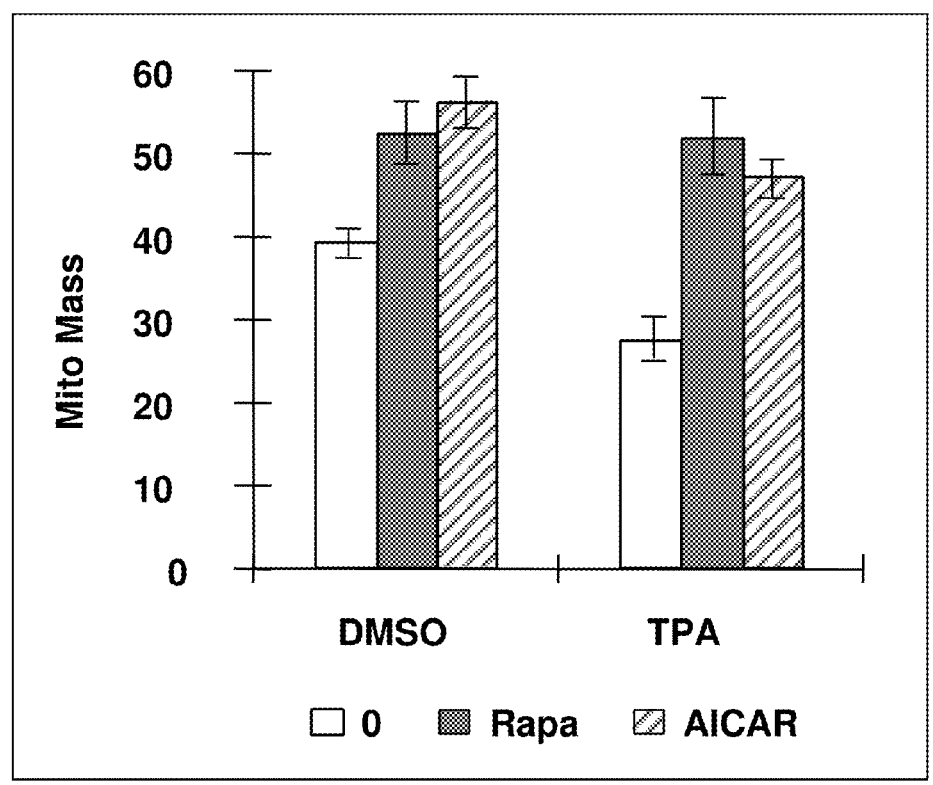
FIG. 12 shows that the low doses of rapamycin and AICAR reverse the mitochondrial mass decrease induced by 12-O-tetradecanoylphorbol 13-acetate (TPA). NIH3T3 cells were incubated in DMEM medium (DMEM with 10% FCS, 100 units/mL penicillin, 100 μg/mL streptomycin and 2 mM glutamine) in the presence of control DMSO, 10 μM TPA, 1 nM rapamycin, 10 μM TPA+ 1 nM rapamycin, 40 μM AICAR, or 10 μM TPA+ 40 μM AICAR at 37° C. in a humidified atmosphere consisting of 95% air and 5% $CO_2$ for two days. Cells were then harvested by trypsin and fixed by 60% ethanol. The cells were stained with MitoTracker Greeen FM in darkness for 30 min prior to FACS analysis. The data represents the average of a triplica-experiment.
Figure 13A:
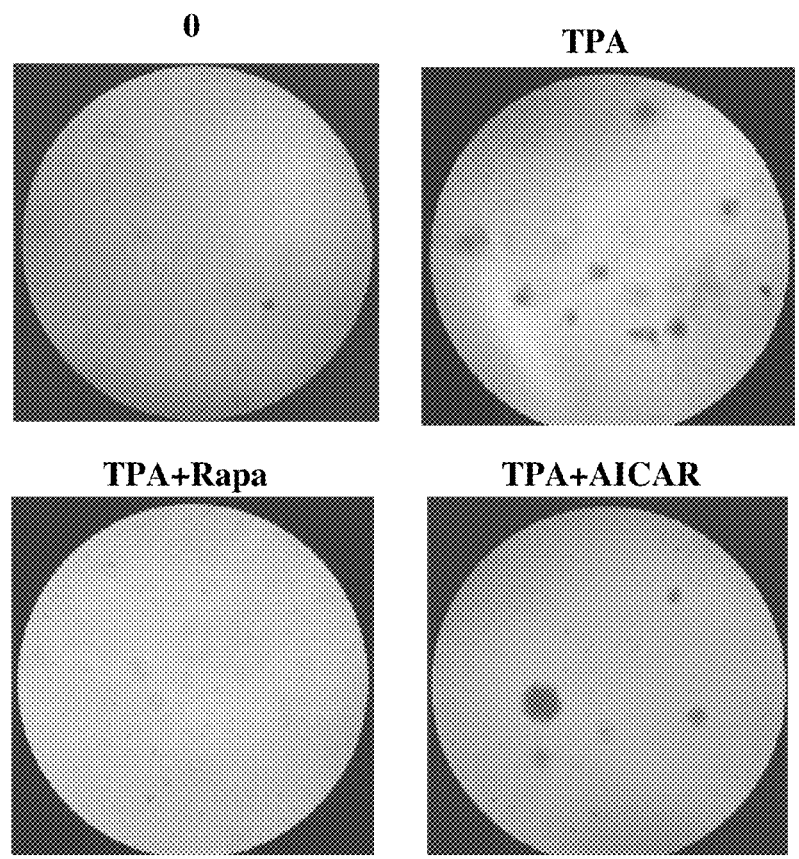
FIG. 13 shows that the low doses of rapamycin and AICAR prevent NIH3T3 tumor transformation induced by TPA. (A) TPA (10 μM) was incubated with NIH3T3 cells in 0.39% soft agar in the presence of DMSO, 1 nM rapamycin, or 250 nM AICAR, and cultured for 7 days prior to counting colonies under a microscope. (B) The data represents the average of four experiments.
Figure 13B:
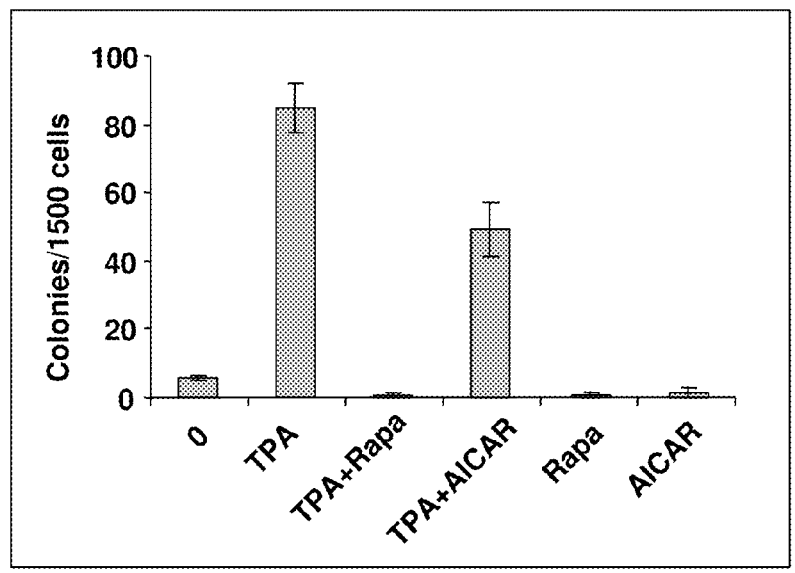

The experiment was done as in Example 19. In brief, 1500 NIH3T3 cells were mixed with 50 μL of 0.4% agarose in culture medium (basal medium with 10% bovine fetal serum), layered on 96-well plates pre-covered with 50 μL of 0.8% agarose in culture medium. 100 μL of culture medium containing drugs to make final DMSO, 10 μM TPA, 40 μM AICAR, or 10 μM TPA+40 μM AICAR was then added into the wells. The cells were incubated in a 37° C. incubator with 5% CO2 for more than 7 days. 50 μL of fresh medium was added every 5 days. Colonies were then counted under a microscope. As shown in FIG. 12, TPA dramatically decreased the mitochondrial mass in NIH 3T3 cells. The AMPK activator AICAR reversed this decrease (FIG. 12). Furthermore, AICAR also reduced the transformation of NIH 3T3 cells induced by TPA (FIG. 13A and FIG. 13B).

C. Use of a TOR Inhibitor as the Mimic of CR for Preventing and Treating Age-Related Diseases or Disorders TOR Inhibitors and Rapamycin. The specific TOR inhibitor rapamycin (Sirolimus) is the original member of a class of macrocyclic triene molecules, comprising CCI779 (Temsirolimus), RAD-001 (Everolimus), AP-23573 (Deforolimus), AP-23675, AP-23841, ABT-578 (Zotarolimus), 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, and 42-O-(2-hydroxy)ethyl rapamycin. Rapamycin was found originally to have antifungal activity (Vezina, C., et al., *J. Antibiot.*, 28:721 (1975); Sehgal, S. N., et al., *J. Antibiot.*, 28:727 (1975); Baker, H. A., et al., *J. Antibiot.*, 31:539 (1978); U.S. Pat. Nos. 3,929,992, and 3,993, 749).

Rapamycin is used as an immunosuppressant (Santos, E. and Nebreda, A. R., *FASEB*, 3:2151-2163 (1989)): preventing or treating systemic lupus erythematosus (U.S. Pat. No. 5,078,999), pulmonary inflammation (U.S. Pat. No. 5,080, 899), rejection in organ transplanting, arthritis (Carlson, et al., *J. Pharmacol. Exp. Ther.*, 266:1125-1138 (1993); Foroncewicz et al, *Transpl. Int.*, 18:366-368 (2005)), ocular inflammation (U.S. Pat. No. 5,387,589), and cardiac inflammatory disease (U.S. Pat. No. 5,496,832), preventing smooth muscle cell proliferation and intimal thickening following vascular injury (U.S. Pat. Nos. 5,288,711 and 5,516,781) and is used on stent for preventing restenosis (U.S. Pat. No. 6,585,764). It is also patented for treating ocular conditions (U.S. Pat. No. 7,083,802), including age-related macular degeneration (AMD) (U.S. Patent Application Publication Nos. 20060182771, 20060247265, 20060263409, and 20070105761, 20060264453), choroidal neovascularization (CNV), and wet AMD (U.S. Patent Application Publication No. 20050187241).

Rapamycin has been shown to have anti-proliferative and antitumor activity. Rapamycin alone, or in combination with other drugs, has been shown to have antitumor activity against adult T-cell leukemia/lymphoma (U.S. Pat. Nos. 4,885,171 and 4,401,653; European Patent Application 525, 960 A1), malignant carcinomas (U.S. Pat. No. 5,206,018), and anemia (U.S. Pat. No. 5,561,138). It can be used to treat metastatic breast cancer (U.S. Patent Application Publication No. 20070104721), neoplasms (U.S. Patent Application Publication Nos. 20040176339 and 20060035904), and early B cell derived acute lymphoblastic leukemia (U.S. Pat. No. 7,026,330). It was also patented for treating tuberous sclerosis (U.S. Patent Application Publication No. 20050070567) and inhibiting abnormal cell growth in mammals (U.S. Patent Application Publication No. 20060035907), reducing the proliferation and enhancing the apoptosis of neoplastic cells (U.S. Patent Application Publication No. 20060094674), and treating proliferative and inflammatory disorders (U.S. Patent Application Publication No. 20060135549), and chronic viral infection (U.S. Patent Application Publication No. 20070099844).

Use of rapamycin/mTOR inhibitors alone or in combination with other agents has also been reported for treating various other diseases or conditions, such as diabetes mellitus (U.S. Pat. No. 5,321,009), skin disorders (U.S. Pat. No. 5,286,730), bowel disorders (U.S. Pat. No. 5,286,731), neurological disorders, neurodegenerating diseases (U.S. Pat. No. 6,187,756), bone loss (U.S. Patent Application Publication No. 20060173033), anti-angiogenic sustained release intraocular implants (U.S. Patent Application Publication No. 20070059336), and protein conformational disorders by induction of autophagy (U.S. Patent Application Publication No. 20070155771).

It was found to form complexes between TOR and FKBP12 and inhibit the complex formation between TOR and its normal substrate proteins such as the TOR-raptor complex (TORC1). Inhibition of TORC1 formation results in inhibiting protein translation and ribosomal biogenesis, thus inhibiting cell cycle at G1 phase. TORC1 inhibition also leads to increased autophagy for degradation of proteins and organelle for nutrients. Up to date, the reported uses of rapamycin at the therapeutic doses on various diseases are primarily based on TORC1 disruption and the subsequent cell cycle G1 inhibition and autophagy. In contrast, in the present invention, rapamycin and its analogs are used at low doses as a mimic of calorie restriction for the prevention or treatment of age-related diseases via the AMPK/Mitochondria/Senescence pathway.

Example 15

Low Doses of Rapamycin Inhibit TPA-Induced Transformation of NIH3T3 Cells

Transformation of NIH 3T3 cells is a good in vitro tumorigenesis assay, which measures colony formation in soft agar (termed as anchorage-independent growth). The mutagen TPA (12-O-Tetradecanoylphorbol 13-acetate) is known to stimulate protein kinase C (PKC), activate oncogenes and transform mouse embryonic fibroblast NIH3T3 cells. The TPA-induced anchorage-independent growth of NIH3T3 cell was employed as a tumorigenesis assay. Interestingly, 10 µM TPA dramatically decreased the mitochondrial mass in NIH 3T3 cells, and 1 nM rapamycin reversed this decrease as shown in FIG. 12. Furthermore, 1 nM rapamycin also eliminated transformation of NIH 3T3 cells induced by 10 µM TPA (FIG. 13). 1500 NIH3T3 cells were mixed with 50 µL of 0.4% agarose in culture medium (basal medium with 10% bovine fetal serum), layered on 96-well plates pre-covered with 50 µL of 0.8% agarose in culture medium. 100 µL of culture medium containing drugs to make final DMSO, 10 µM TPA, 1 nM rapamycin, or 10 µM TPA+1 nM rapamycin was then added into the wells. The cells were incubated in a 37° C. incubator with 5% CO2 for more than 7 days. 50 µL of fresh medium was added every 5 days. Colonies were then counted under a microscope. As shown in FIG. 13A and FIG. 13B, 1 nM rapamycin totally blocked this process. As 1 nM rapamycin slightly slowed down the growth rate of NIH3T3, colonies were also counted after 21-day's incubation to wait for the slowing growth colonies. However, the same results were obtained. Therefore, the slow growth by 1 nM rapamycin is not the cause for elimination of colony formation. It rather supports the role mitochondrial function in preventing anchorage-independent growth or tumorigenesis via senescence maintaining. In contrast, therapeutic doses of rapamycin have been reported to promote tumorigenesis and thus increase the risk of lymphoma, skin cancer and other cancers in human. The antiproliferation activity of rapamycin at therapeutic doses discovered recently is to limit the growth of existing tumors, assumed by its inhibition in G1 cell cycle and in protein synthesis Furthermore, AICAR (40 µM) that activates AMPK and prolongs the life span of senescent primary fibroblasts of human (FIG. 7) also reverses the decrease in mitochondrial mass triggered by TPA (FIG. 12), as well as inhibits the anchorage-independent growth (FIG. 13A and FIG. 13B). These data further support the role of mitochondrial function in preventing anchorage-independent growth or tumorigenesis. In conclusion, low doses of rapamycin and AICAR prevent tumorigenesis, at least in the case induced by a mutagen TPA.

Example 16

Figure 14A:
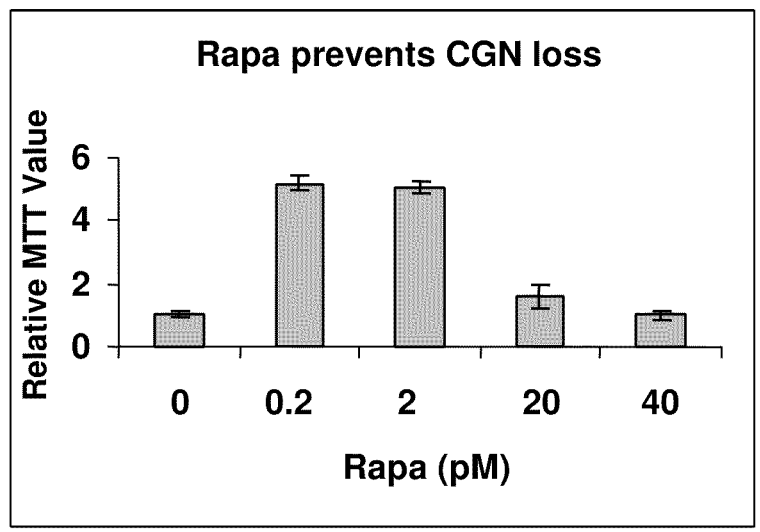
FIG. 14 shows that rapamycin at low doses, 0.2 and 2 pM, extends the life span of cultured CGN cells (A) and reduces ROS levels in CGN cells (B). Cerebellar granule neuron (CGN) cultures were prepared from 7-day-old rat pups. Briefly, the cerebellum was removed from the brain, minced into fine pieces, trypsinized at 37° C. for 15 min, filtered through a 40-μM mesh, and pelleted by centrifugation. The pellets containing cerebellar granule neurons were resuspended in B27 supplemented neurobasal medium containing 25 mM KCl. For their life span in culture, cells were then seeded into a 24-well plate (1 plate/cerebellum) and cultured in Neurobasal medium (Invitrogen) supplemented with B27, 20 mM KCl, 0.5 mM Glutamine, 100 units/mL penicillin, 100 μg/mL streptomycin). Rapamycin was added 7 days after in plate. 31 days later, survival of neuron cells was determined using a MTT assay (A). For ROS analysis, fresh isolated CGN cells in suspension culture in Neurobal complete medium were seeded in 12×75 mm tubes at a density of 1 million cells/mL/tube. The cells were treated with rapamycin for 20 hrs and then stained with 2 μg/mL dehydrorhodamine 123 for 30 min prior to FACS analysis (B).
Figure 14B:
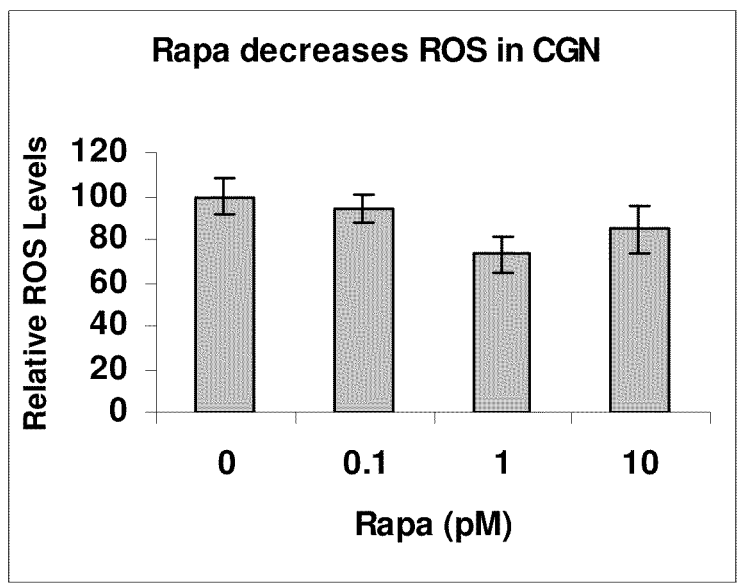

Low Doses of Rapamycin Reduce ROS and Extend Life Span of Cultured GCN Neuron Cells Cerebellar granule neuron (CGN) cultures were prepared from 7-day-old rat pups. Briefly, the cerebellum was removed from the brain and placed in a Petri dish containing BMEM in 20 mM HEPES buffer (BMEM-HEPES). Cerebella were meninges and blood vessels were discarded to ensure minimal contamination from endothelial cells. Cerebella/cerebral cortices were then minced into fine pieces with dissecting knives and trypsinized at 37° C. for 15 min. Trypsinization was inhibited by adding 1 mL of BME containing 0.025% soybean trypsin inhibitor and 0.05% DNase I. The tissue was gently triturated through a fire-polished Pasteur pipette until it was dispersed into a homogeneous suspension. The suspension was filtered through an ethanol-sterilized 40-µM mesh and pelleted by centrifugation. The pellets containing cerebellar granule neurons were resuspended in B27 supplemented neurobasal medium containing 25 mM KCl (Invitrogen, Carlsbad, Calif.). Cells were then seeded into a 24-well plate (1 plate/cerebellum) and cultured in Neurobasal medium (Invitrogen) supplemented with B27, 20 mM KCl, 0.5 mM Glutamine, 100 units/mL penicillin, 100 µg/mL streptomycin. Rapamycin was added to the culture 7 days. 31 days later, the MTT assay was performed to determine survival of neuron cells. As shown in FIG. 14A, the majority of CGN cells had already been lost after 31 days in culture. However, low doses of rapamycin prevented such a loss and extended the life span of the GCN cells in culture, but higher doses of rapamycin did not have such as effect.

For ROS analysis, fresh isolated CGN cells in suspension culture in Neurobal complete medium were seeded in 12×75 mm tubes at a density of one (1) million cells/mL/tube. Cells were treated with rapamycin for 20 hrs and then stained with 2 µg/mL dehydrorhodamine 123 for 30 min prior to FACS analysis. As show FIG. 14B, rapamycin reduced the regular ROS level of CGN cells in suspension Example 17

Low Doses of Rapamycin Reduce the Cerebellar Infarction Size in a Rat Stroke Model The middle cerebral artery (MCA) occlusion model of ischemic stroke was used in this example. Spontaneously Hypertensive Stroke Prone (SHR-SP) rats were randomly divided into two groups (n=8 in each group): a matched control DMSO group and rapamycin group. They were anesthetized with 15% chloral hydrate (300 mg/kg, i.p.). Permanent focal cerebral ischemia was induced by electrocoagulation of the distal portion of the MCA using a modified method described by Tamura and McGill (Tamura, A., et al., *J. Cerebral. Blood Flow Metab.*, 1:53-60 (1981). McGill, J. K., et al., *Stroke*, 36:135-141 (2005)). Briefly, a segment of right MCA between the olfactory bundle and the inferior cerebral vein was electro-coagulated. The coagulated artery was severed with microscissors to ensure complete stop of blood supply.

Rapamycin and the control DMSO were administrated 10 minutes after MCA occlusion. Brain samples were harvested 24 h after MCA occlusion. Coronal sections of 2 mm in thickness were immediately stained with 2% 2,3,5-triphenyltetrazolium chloride (TTC). The infarction region looked pale, while the normal region looked red. The infarction area and hemisphere areas of each section (both sides) were traced and quantified by an image analysis system (Microsystems Type DM LB2, Leica, Germany). The possible interference of a brain edema in assessing the infarction volume was corrected for with a standard method of subtracting the volume of the nonischemic ipsilateral hemisphere from the contralateral hemisphere volume. The infarction volume was expressed as a percentage of the contralateral hemisphere. The weights of the infarction tissue and the hemisphere were measured in a similar manner. As shown in FIG. 15A, rapamycin at a low dose 10 μg/kg significantly reduced the infarction volume induced by MCA occlusion. In contrast, rapamycin at a normal dose of 1 mg/kg did not have this effect, as reported in the literature (Sharkey, J. J. and Butcher, S. P., *Nature*, 371:336-339 (1994)). Furthermore, administration of rapamycin at doses of 0, 0.3, 1, 3 and 10 μg/kg for 20 days prior to MCA occlusion also prevented the brain damage (FIG. 15B).

Example 18

Low Doses of Rapamycin Reduce MPP+ Induced ROS

MPP$^+$, an inhibitor of complex I (NADH CoQ1 reductase) in the mitochondrial respiratory chain, is a dopaminergic neurotoxin. It is commonly used to induce Parkinson's disease in marine models. Human primary fibroblast WI-38 cells were treated with 200 μM MPP for 3 days. Various concentrations of rapamycin were also incubated with cells for 3 days as indicated in FIG. 14. Cells were then stained with dehydrorhodamine 123 in the dark for 30 min. Cells were then analyzed by FACS. Dehydrorhodamine 123 can be oxidized to rhodamine (that shows fluorescence) in proportion to ROS levels. As shown in FIG. 16, MPP$^+$ greatly increased ROS level. Low doses of rapamycin in picomolar (pM) ranges significantly reduced this increase.

Example 19

Low Doses of Rapamycin Reduce Myocardial Infarction Size in a Rat Model

To determine Myocardial Infarction (MI) in Rats, Male Sprague-Dawley (SD) rats of 200 to 250 g by weight were used (n=10-12 for each group). Rapamycin at doses of 0, 10, or 100 μg/kg/day was administrated for 3 days prior to the MI experiment. Under ether anesthesia conditions, the heart was exteriorized via a left thoracotomy, and the left anterior descending arteries were ligatured with 6-0 polypropylene suture between the pulmonary outflow tract and left atrium. Then the beating heart was quickly returned to its normal position, the thorax was closed, and the air was removed. Rats were returned to the cages with the previously mentioned conditions. Five hours after the coronary artery ligature, the rats were killed by an overdose of pentobarbital. The left ventricle was isolated and cut into 4 to 5 slices perpendicular to the cardiac long axis. The slices were stained for 30 min at 37° C. in a 0.1% solution of nitro blue tetrazolium phosphate buffer and the MI size was measured as described (Lin, L. L., et al, *J. Cardiovasc. Pharmaco.*, 50:327-332 (2007)). The normal tissue was stained in blue, while the necrotic tissue remained unstained. The stained and unstained tissues were isolated and weighed separately. The MI size was expressed as a fraction of the total left ventricular weight. As shown in FIG. 16, the low dose of rapamycin at 10 μg/kg/day significantly reduced the myocardial infarction size, but not the higher dose 100 μg/kg/day.

Every patent and non-patent publication cited in the instant disclosure is incorporated into the disclosure by reference to the same effect as if every publication is individually incorporated by reference. Citation or identification of any document in this application is not an admission that such document is available as prior art to the present invention.

It is understood that the foregoing detailed descriptions and accompanying examples are merely illustrative and are not to be taken as limitations upon the scope of the invention. Many variations of the invention will become apparent to those skilled in the art upon review of this specification. The full scope of the invention should be determined by reference to the claims, along with their full scope of equivalents, and the specification, along with such variations.

What is claimed is:

1. A method of preventing cell aging by extending the G0 phase in a cell in a subject in need thereof, the method comprising administering a low dose of a target-of-rapamycin (TOR) inhibitor to a subject, wherein:
    (a) said TOR inhibitor is rapamycin or an analog thereof selected from the group consisting of Deforolimus, AP-23675, AP-23841, Zotarolimus, CCI779/Temsirolimus, RAD-001/Everolimus, 7-epi-rapamycin, 7-thiomethyl-rapamycin, 7-epi-trimethoxy-rapamycin, 2-desmethyl-rapamycin, and 42-O-(2-hydroxy)ethyl-rapamycin, or a pharmaceutically acceptable salt thereof; and
    (b) said low dose of TOR inhibitor does not inhibit protein translation and cell growth at G1 phase of cell cycle.

2. The method of claim 1, wherein said TOR inhibitor is rapamycin, or a pharmaceutically acceptable salt thereof.

3. The method of claim 2, wherein the low dose of rapamycin is below about 1% of a therapeutic dose, wherein said therapeutic dose is in the range of 1 mg/day to 5mg/day.

4. The method of claim 3, wherein the low dose of rapamycin is below about 0.1% of the therapeutic dose.

5. The method of claim 3, wherein the low dose of rapamycin is below about 0.01% of the therapeutic dose.

6. The method of claim 3, wherein the low dose of rapamycin is below about 0.001% of the therapeutic dose.

7. The method of claim 1, wherein said subject is a human.

8. The method of claim 7, wherein the low dose of rapamycin is in the range from about 0.01 μg/day to about 50 μg/day.

9. A method of preventing cell aging by extending the G0 phase in a cell in a subject in need thereof, the method comprising administering a low dose of a target-of-rapamycin (TOR) inhibitor in conjunction with administration of a second agent to a subject, wherein:
(a) said TOR inhibitor is rapamycin or an analog thereof selected from the group consisting of Deforolimus, AP-23675, AP-23841, Zotarolimus, CCI779/Temsirolimus, RAD-001/Everolimus, 7-epi-rapamycin, 7-thiomethyl-rapamycin, 7-epi-trimethoxy-rapamycin, 2-desmethyl-rapamycin, and 42-O-(2-hydroxy)ethyl-rapamycin, or a pharmaceutically acceptable salt thereof;
(b) said second agent is independently selected from antioxidants, antihypertensive agents, lipid-lowering agents, anti-stroke agents, anti-cancer agents, and different anti-aging agents; and
(c) said low dose of TOR inhibitor does not inhibit protein translation and cell growth at G1 phase of cell cycle.

10. The method of claim 9, wherein the TOR inhibitor is rapamycin, or a pharmaceutically acceptable salt thereof.

11. The method of claim 9, wherein said second agent is an antioxidant selected from vitamin C, vitamin E, beta carotene and other carotenoids, selenium, lipoic acid, lycopene, lutein, zeaxanthin, coenzyme Q10, glutathione, N-acetyl cysteine, melatonin, genistein, estrodiol, tea extract, and grape seed extract.

12. The method of claim 9, wherein said second agent is another anti-aging agent selected from the group consisting of AICAR, EGCG, grape seed extract, bilberry extract, selenite, genistein, diallyl trisulfide, benzyl isothiocyanate, phenyl isothiocyanate, phenethyl isothiocyanate, resveratrol, lycopene, and allyl isothiocyanate.

13. The method of claim 10, wherein the low dose of rapamycin is below about 1% of a therapeutic dose, wherein said therapeutic dose is in the range of 1 mg/day to 5mg/day.

14. The method of claim 13, wherein the low dose of rapamycin is below about 0.1% of the therapeutic dose.

15. The method of claim 13, wherein the low dose of rapamycin is below about 0.01% of the therapeutic dose.

16. The method of claim 13, wherein the low dose of rapamycin is below about 0.001% of the therapeutic dose.

17. The method of claim 9, wherein said subject is a human.

18. The method of claim 17, wherein the low dose of rapamycin is in the range from about 0.01 μg/day to about 50 μg/day.

* * * * *